(12) United States Patent
Fike et al.

(10) Patent No.: US 6,383,810 B2
(45) Date of Patent: *May 7, 2002

(54) DRY POWDER CELLS AND CELL CULTURE REAGENTS AND METHODS OF PRODUCTION THEREOF

(75) Inventors: Richard Fike, Clarence, NY (US); William Whitford, Santa Fe, NM (US); William Biddle, Buffalo, NY (US)

(73) Assignee: Invitrogen Corporation, Carlsbad, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/023,790

(22) Filed: Feb. 13, 1998

Related U.S. Application Data
(60) Provisional application No. 60/062,192, filed on Oct. 16, 1997, provisional application No. 60/058,716, filed on Sep. 12, 1997, and provisional application No. 60/040,314, filed on Feb. 14, 1997.

(51) Int. Cl.[7] ............................ C12N 5/00; C12N 1/20; C12N 1/14; C12N 1/16; C12N 1/18
(52) U.S. Cl. ................. 435/384; 435/243; 435/253.6; 435/255.21; 435/256.8; 435/325; 435/404; 435/410; 435/431
(58) Field of Search .......................... 34/372; 435/243, 435/325, 4, 384; 436/18; 426/443, 453, 455, 471, 588, 285, 289, 240, 242, 392, 394, 384

(56) References Cited

U.S. PATENT DOCUMENTS

| | | |
|---|---|---|
| 3,771,237 A | 11/1973 | Hansen et al. |
| 4,071,412 A | 1/1978 | Eisenberg et al. |
| 4,490,403 A | * 12/1984 | Pisecky et al. |
| 4,511,592 A | 4/1985 | Percel et al. |
| 4,544,637 A | 10/1985 | Keggins et al. |
| 4,615,978 A | 10/1986 | Sandine et al. |
| 4,620,908 A | 11/1986 | Van Duzer |

(List continued on next page.)

FOREIGN PATENT DOCUMENTS

| | | | |
|---|---|---|---|
| CS | 169007 | * | 6/1976 |
| DK | 167090 B1 | | 8/1993 |
| EP | 0 356 071 A2 | | 2/1990 |
| SU | 1097253 | | 6/1984 |
| WO | WO 9427645 | * | 6/1976 |
| WO | WO 95/13867 | | 5/1995 |

OTHER PUBLICATIONS

Camire, J.C.F., et al., "Efficient Cultivation of Cells Using Powdered Serum," In Vitro 34:Abstract No. V–1008 (Mar. 1998).

Robey, T.E., and Ryan, J.M, "A Comparison of the Effects of Powdered and Liquid Fetal Bovine Serum on Normal Human Cell Growth, Metabolism and Urokinase Formation," In Vitro 34:Abstract No. V–1007 (Mar. 1998).

"Granulated Media," in Microbiology Catalog, EM Science, Cincinnati, Ohio (1999).

Product and Corporate Information, American Protein Corporation, <http://www.AmericanProtein.com/index.html> (Jul. 1999).

Freshney, R.I., "The Culture Environment: II. Media and Supplements," In: *Culture of Animal Cells: A Manual of Basic Technique*, Alan R. Liss, Inc., New York, NY, pp. 74–78 (1983).

GEA Process Technology Division, Aeromatic–Fielder Division, technical brochure entitled "Batch fluid beds: Customized fluid bed systems for solids processing," Columbia, MD.

GEA Pharmaceutical Processing, Marketing brochure entitled "Plant and Process Technology by the GEA Companies."

(List continued on next page.)

*Primary Examiner*—Christopher R. Tate
*Assistant Examiner*—Michele C. Flood
(74) *Attorney, Agent, or Firm*—Sterne, Kessler, Goldstein & Fox P.L.L.C.

(57) ABSTRACT

The present invention relates generally to nutritive medium, medium supplement, media subgroup and buffer formulations. Specifically, the present invention provides powder nutritive medium, medium supplement and medium subgroup formulations, particularly cell culture medium supplements (including powdered sera such as powdered fetal bovine serum (FBS)), medium subgroup formulations and cell culture media comprising all of the necessary nutritive factors that facilitate the in vitro cultivation of cells. The invention further provides powder buffer formulations that produce particular ionic and pH conditions upon reconstitution with a solvent. The invention is particularly directed to methods of production of these media, media supplement, media subgroup and buffer formulations, and also provides kits and methods for cultivation of prokaryotic and eukaryotic cells, particularly bacterial cells, yeast cells, plant cells and animal cells (including human cells) using these dry powder nutritive media, media supplement, media subgroup and buffer formulations. The invention also relates to methods of producing sterile powdered media, media supplement (particularly powdered sera such as powdered FBS, powdered transferrin, powdered insulin, powdered organ extracts (such as bovine brain or pituitary extracts), powdered growth factors (such as EGF, FGF, etc.) and the like), media subgroup and buffer formulations. In a particularly preferred aspect, the invention relates to such methods wherein the sterilization is accomplished by gamma irradiation. The invention also relates to methods for producing dry cell powders, comprising spray-drying a cell suspension. The invention also relates to cell, media, media supplement, media subgroup and buffer powders produced by these methods.

24 Claims, 25 Drawing Sheets

U.S. PATENT DOCUMENTS

| | | | |
|---|---|---|---|
| 4,621,058 A | | 11/1986 | Reddy |
| 4,689,297 A | | 8/1987 | Good et al. |
| 4,820,627 A | * | 4/1989 | McGeehan |
| 4,885,848 A | | 12/1989 | Christensen et al. |
| 4,999,301 A | | 3/1991 | Bryan-Jones |
| 5,006,204 A | | 4/1991 | Jensen |
| 5,133,137 A | | 7/1992 | Petersen |
| 5,325,606 A | | 7/1994 | Liborius |
| 5,357,688 A | | 10/1994 | Christensen |
| 5,392,531 A | | 2/1995 | Christensen et al. |
| 5,474,931 A | | 12/1995 | DiSorbo et al. |
| 5,580,856 A | | 12/1996 | Prestrelski et al. |
| 5,756,046 A | | 5/1998 | Winks et al. |
| 5,773,061 A | * | 6/1998 | Getler et al. |
| 5,811,406 A | | 9/1998 | Szoka, Jr. et al. |

OTHER PUBLICATIONS

GIBCO BRL 1995–1996 Product Catalogue and Reference Guide, Life Technologies, Inc., Gaithersburg, MD (Jan. 1995).

Harlow, E., and Lane, D., "Sampling Serum," In: *Antibodies: A Laboratory Manual*, Cold Spring Harbor Laboratory (1988).

Niro, Inc., Technical Bulletin No. 95001 entitled "Fluid Bed Multi–Processor," Aeromatic–Fielder Division, Columbia, MD (1995).

Marketing brochure for EZMix Fermentation Media, Sigma, St. Louis, MO, publication date before Oct. 1, 1996.

Dialog File 351, Derwent WPI, Accession No. 76–44200X/197624, English language abstract for Denmark Patent Publication No. DK 167090.

WIPDS Database on STN, Accession No. 85–005539, English language abstract for Soviet Union Patent Publication No. SU 1097253.

Davis, B et al. Microbiology: Including Immunology and Molecular Genetics, Chapter 67, 3rd Edition, Harper & Row, Philadelphia, pp. 1264–1274, 1980.*

Hay et al., American Type Culture Collection Catalogue of Cell Lines and Hybridomas, 6th Edition, ATCC, Rockville, MD, p 347, 1988.*

Hana et al., Chemical Abstracts, vol. 88, 17, 118717. Preservation of sera, protein fractions, and tissue cultures media by spray drying, Apr. 24, 1978.*

Downes et al., Suid Afrikaanse Tydskrif Vir Veekunde (S. Afr. J. Anim. Sci.), vol. 17, 2, pp 55–58. The relative value of irradiated spray–dried blood powder and heat–sterilized blood meal as measured in combination with whey protein, 1987.*

* cited by examiner

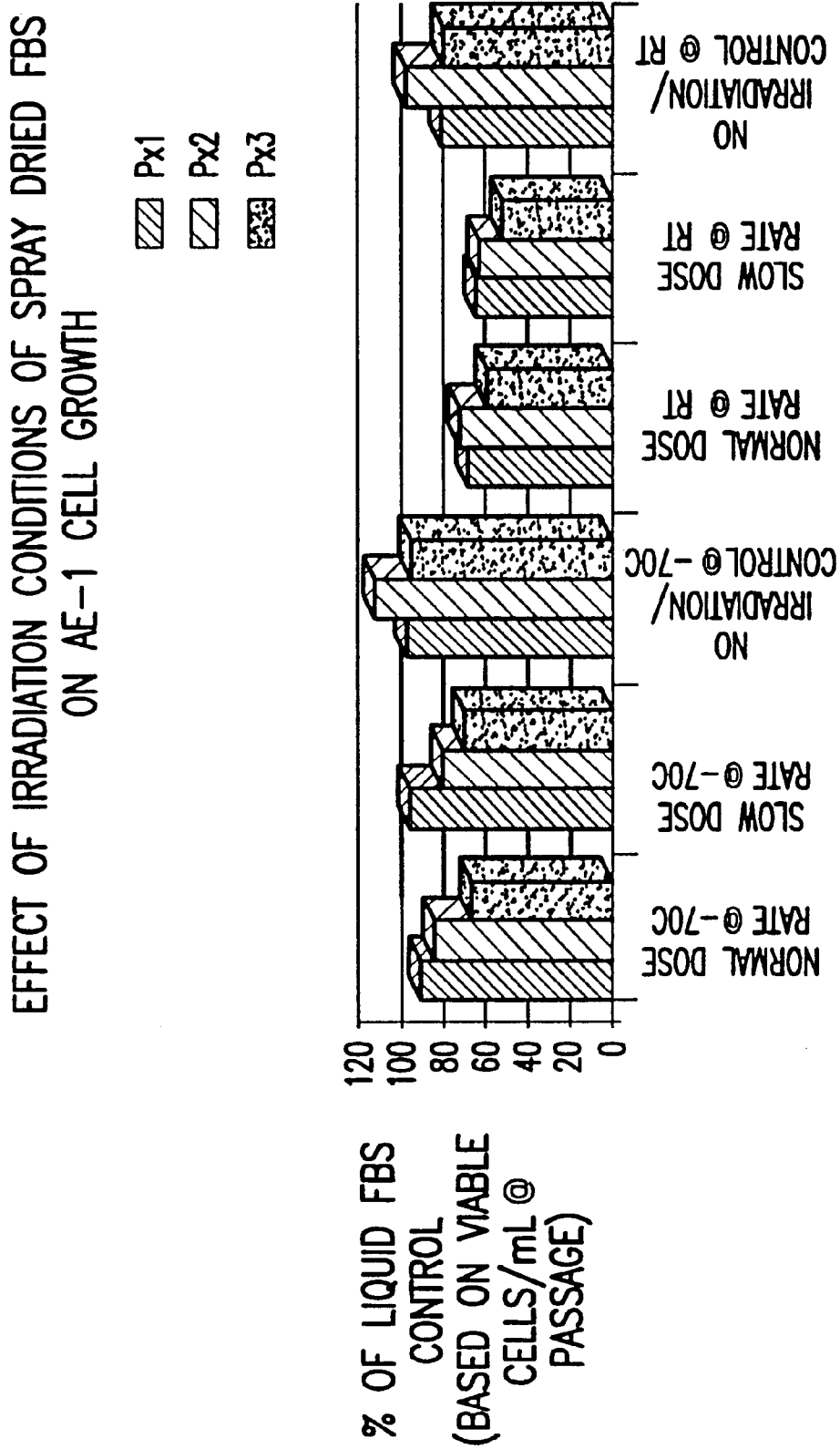

FIG. 17C

DRY POWDER CELLS AND CELL CULTURE REAGENTS AND METHODS OF PRODUCTION THEREOF

CROSS REFERENCE TO RELATED APPLICATIONS

This application claims priority to U.S. Provisional Application Nos. 60/040,314, filed Feb. 14, 1997, 60/058,716, filed Sep. 12, 1997, and 60/062,192, filed Oct. 16, 1997, the disclosures of which are entirely incorporated herein by reference.

FIELD OF THE INVENTION

The present invention relates generally to cells, nutritive media, media supplements, media subgroups and buffer formulations. Specifically, the present invention provides dry powder nutritive medium formulations, particularly cell culture medium formulations, comprising all of the necessary nutritive factors that facilitate the in vitro cultivation of cells, and methods of production of these media formulations. The invention also relates to methods of producing dry powder media supplements, such as dry powder sera (e.g., fetal bovine serum). The invention also relates to dry powder buffer formulations that produce particular ionic and pH conditions upon rehydration. The invention also relates to methods of producing dry powder cells, such as prokaryotic (e.g., bacterial) and eukaryotic (e.g., fungal (especially yeast), animal (especially mammalian) and plant cells). The invention also relates to methods of preparing sterile dry powder nutritive media, media supplements (particularly dry powder sera), media subgroups and buffer formulations. The invention also relates to dry powder nutritive media, media supplements, media subgroups, buffer formulations and cells prepared by these methods. The present invention also relates to kits and methods for cultivation of prokaryotic and eukaryotic cells using these dry powder nutritive media, media supplements, media subgroups and buffer formulations.

BACKGROUND OF THE INVENTION

Cell Culture Media

Cell culture media provide the nutrients necessary to maintain and grow cells in a controlled, artificial and in vitro environment. Characteristics and compositions of the cell culture media vary depending on the particular cellular requirements. Important parameters include osmolality, pH, and nutrient formulations.

Media formulations have been used to cultivate a number of cell types including animal, plant and bacterial cells. Cells cultivated in culture media catabolize available nutrients and produce useful biological substances such as monoclonal antibodies, hormones, growth factors, viruses and the like. Such products have therapeutic applications and, with the advent of recombinant DNA technology, cells can be engineered to produce large quantities of these products. Thus, the ability to cultivate cells in vitro is not only important for the study of cell physiology, but is also necessary for the production of useful substances which may not otherwise be obtained by cost-effective means.

Cell culture media formulations have been well documented in the literature and a number of media are commercially available. In early cell culture work, media formulations were based upon the chemical composition and physicochemical properties (e.g., osmolality, pH, etc.) of blood and were referred to as "physiological solutions" (Ringer, S., *J. Physiol.*. 3:380–393 (1880); Waymouth, C., In: *Cells and Tissues in Culture,* Vol. 1, Academic Press, London, pp. 99–142 (1965);Waymouth, C., *In Vitro* 6:109–127 (1970)). However, cells in different tissues of the mammalian body are exposed to different microenvironments with respect to oxygen/carbon dioxide partial pressure and concentrations of nutrients, vitamins, and trace elements; accordingly, successful in vitro culture of different cell types will often require the use of different media formulations. Typical components of cell culture media include amino acids, organic and inorganic salts, vitamins, trace metals, sugars, lipids and nucleic acids, the types and amounts of which may vary depending upon the particular requirements of a given cell or tissue type. Often, particularly in complex media compositions, stability problems result in toxic products and/or lower effective concentrations of required nutrients, thereby limiting the functional life-span of the culture media. For instance, glutamine is a constituent of almost all media that are used in culturing of mammalian cells in vitro. Glutamine decomposes spontaneously into pyrolidone carboxylic acid and ammonia. The rate of degradation can be influenced by pH and ionic conditions but in cell culture media, formation of these breakdown products often cannot be avoided (Tritsch et al., *Exp. Cell Res.* 28:360–364(1962)).

Wang et al. (*In Vitro* 14(8):715–722 (1978)) have shown that photoproducts such as hydrogen peroxide, which are lethal to cells, are produced in Dulbecco's Modified Eagle's Medium (DMEM). Riboflavin and tryptophan or tyrosine are components necessary for formation of hydrogen peroxide during light exposure. Since most mammalian culture media contain riboflavin, tyrosine and tryptophan, toxic photoproducts are likely produced in most cell culture media.

To avoid these problems, researchers make media on an "as needed" basis, and avoid long term storage of the culture media. Commercially available media, typically in dry power form, serves as a convenient alternative to making the media from scratch, i.e., adding each nutrient individually, and also avoids some of the stability problems associated with liquid media. However, only a limited number of commercial culture media are available, except for those custom formulations supplied by the manufacturer.

Although dry powder media formulations may increase the shelf-life of some media, there are a number of problems associated with dry powdered media, especially in large scale application. Production of large media volumes requires storage facilities for the dry powder media, not to mention the specialized media kitchens necessary to mix and weigh the nutrient components. Due to the corrosive nature of dry powder media, mixing tanks must be periodically replaced.

Typically, cell culture media formulations are supplemented with a range of additives, including undefined components such as fetal bovine serum (FBS) (10–20% v/v) or extracts from animal embryos, organs or glands (0.5–10% v/v). While FBS is the most commonly applied supplement in animal cell culture media, other serum sources are also routinely used, including newborn calf, horse and human. Organs or glands that have been used to prepare extracts for the supplementation of culture media include submaxillary gland (Cohen, S., *J. Biol. Chem.* 237:1555–1565 (1961)), pituitary (Peehl, D. M., and Ham, R. G., *In Vitro* 16:516–525 (1980); U.S. Pat. No. 4,673,649), hypothalarus (Maciag, T., et al., *Proc. Natl. Acad. Sci. U.S.A.* 76:5674–5678 (1979); Gilchrest, B. A., et al., *J. Cell. Physiol.* 120:377–383 (1984)), ocular retina (Barretault, D., et al., *Differentiation* 18:29–42 (1981)) and brain (Maciag, T., et al., *Science*

211:1452–1454 (1981)). These types of chemically undefined supplements serve several useful functions in cell culture media (Lambert, K. J. et al., In: *Animal Cell Biotechnology*, Vol. 1, Spier, R. E. et al., Eds., Academic Press New York, pp. 85–122 (1985)). For example, these supplements provide carriers or chelators for labile or water-insoluble nutrients; bind and neutralize toxic moieties; provide hormones and growth factors, protease inhibitors and essential, often unidentified or undefined low molecular weight nutrients; and protect cells from physical stress and damage. Thus, serum or organ/gland extracts are commonly used as relatively low-cost supplements to provide an optimal culture medium for the cultivation of animal cells.

Methods of Production of Culture Media

Culture media are typically produced in liquid form or in powdered form. Each of these forms has particular advantages and disadvantages.

For example, liquid culture medium has the advantage that it is provided ready-to-use (unless supplementation with nutrients or other components is necessary), and that the formulations have been optimized for particular cell types. Liquid media have the disadvantages, however, that they often do require the addition of supplements (e.g., L-glutamine, serum, extracts, cytokines, lipids, etc.) for optimal performance in cell cultivation. Furthermore, liquid medium is often difficult to sterilize economically, since many of the components are heat labile (thus obviating the use of autoclaving, for example) and bulk liquids are not particularly amenable to penetrating sterilization methods such as gamma or ultraviolet irradiation; thus, liquid culture media are most often sterilized by filtration, which can become a time-consuming and expensive process. Furthermore, production and storage of large batch sizes (e.g., 1000 liters or more) of liquid culture media are impractical, and the components of liquid culture media often have relatively short shelf lives.

To overcome some of these disadvantages, liquid culture medium can be formulated in concentrated form; these media components may then be diluted to working concentrations prior to use. This approach provides the capability of making larger and variable batch sizes than with standard culture media, and the concentrated media formulations or components thereof often have longer shelf-life (see U.S. Pat. No. 5,474,931, which is directed to culture media concentrate technology). Despite these advantages, however, concentrated liquid media still have the disadvantages of their need for the addition of supplements (e.g., FBS, L-glutamine or organ/gland extracts), and may be difficult to sterilize economically.

As an alternative to liquid media, powdered culture media are often used. Powdered media are typically produced by admixing the dried components of the culture medium via a mixing process, e.g., ball-milling, or by lyophilizing pre-made liquid culture medium. This approach has the advantages that even larger batch sizes may be produced, the powdered media typically have longer shelf lives than liquid media, and the media can be sterilized by irradiation (e.g., gamma or ultraviolet irradiation) or ethylene oxide permeation after formulation. However, powdered media have several distinct disadvantages. For example, some of the components of powdered media become insoluble or aggregate upon lyophilization such that resolubilization is difficult or impossible. Furthermore, powdered media typically comprise fine dust particles which can make them particularly difficult to reconstitute without some loss of material, and which may further make them impractical for use in many biotechnology production facilities operating under GMP/ GLP, USP or ISO 9000 settings. Additionally, many of the supplements used in culture media, e.g., L-glutamine and FBS, cannot be added to the culture medium prior to lyophilization or ball-milling due to their instability or propensity to aggregate upon concentration or due to their sensitivity to shearing by processes such as ball-milling. Finally, many of these supplements, particularly serum supplements such as FBS, show a substantial loss of activity or are rendered completely inactive if attempts are made to produce powdered supplements by processes such as lyophilization.

Thus, there exists a current need for rapidly dissolving nutritionally complex stable dry powder nutritive media, media supplements, media subgroups and buffers, which can be prepared in variable bulk quantities and which are amenable to sterilization particularly by ionizing or ultraviolet irradiation.

SUMMARY OF THE INVENTION

The present invention provides methods for the production of nutritive media, media supplement, media subgroup and buffer powders comprising agglomerating a dry powder nutritive media, media supplement, media subgroup or buffer with a solvent. The invention also relates to methods for the production of powdered nutritive media, media supplements, media subgroups, and buffers, comprising spray-drying a liquid nutritive medium, medium supplement, medium subgroup or buffer under conditions sufficient to produce their dry powder counterparts. Such conditions may, for example, comprise controlling heat and humidity until the powdered media, media supplement, media subgroup or buffer is formed. According to the invention, the method may further comprise sterilizing the nutritive media, media supplement, media subgroup or buffer powder, which may be accomplished prior to or after packaging the powder. In particularly preferred methods, the sterilization is accomplished after packaging of the powder by irradiation of the packaged powder with gamma rays.

Particularly preferred nutritive medium powders that may be produced according to the invention include culture medium powders selected from the group consisting of a bacterial culture medium powder, a yeast culture medium powder, a plant culture medium powder and an animal culture medium powder.

Particularly preferred media supplements that may be produced by the methods of the invention include: powdered animal sera, such as bovine sera (e.g., fetal bovine, newborn calf or normal calf sera), human sera, equine sera, porcine sera, monkey sera, ape sera, rat sera, murine sera, rabbit sera, ovine sera and the like; cytokines (including growth factors (such as EGF, aFGF, bFGF, HGF, IGF-1, IGF-2, NGF and the like), interleukins, colony-stimulating factors and interferons); attachment factors or extracellular matrix components (such as collagens, laminins, proteoglycans, glycosaminoglycans, fibronectin, vitronectin and the like); lipids (such as phospholipids, cholesterol, bovine cholesterol concentrate, fatty acids, sphingolipids and the like); and extracts of animal tissues, organs or glands (such as bovine pituitary extract, bovine brain extract, chick embryo extract, bovine embryo extract, chicken meat extract, achilles tendon and extracts thereof) and the like). Other media supplements that may be produced by the present methods include a variety of proteins (such as serum albumins, particularly bovine or human serum albumins; immunoglobulins and fragments or complexes thereof; aprotinin; hemoglobin; haemin or haematin; enzymes (such as trypsin, collagenases, pancreatinin or dispase); lipoproteins; ferritin;

etc.) which may be natural or recombinant; vitamins; amino acids and variants thereof (including, but not limited to, L-glutamine and cystine), enzyme co-factors and other components useful in cultivating cells in vitro that will be familiar to one of ordinary skill.

The nutritive media and media supplements prepared by the invention may also comprise subgroups such as serum (preferably those described above), L-glutamine, insulin, transferrin, one or more lipids (preferably one or more phospholipids, sphingolipids, fatty acids or cholesterol), one or more cytokines (preferably those described above), one or more neurotransmitters, one or more extracts of animal tissues, organs or glands (preferably those described above), one or more proteins (preferably those described above) or one or more buffers (preferably sodium bicarbonate), or any combination thereof Buffer powders particularly suitable for preparation according to the methods of the invention include buffered saline powders, most particularly phosphate-buffered saline powders or Tris-buffered saline powders.

The invention also provides nutritive medium powders, medium supplement powders (including powders of the above-described supplements) and buffer powders prepared according to these methods.

The invention also relates to methods of preparing dried cells, including prokaryotic (e.g., bacterial) and eukaryotic (e.g., fungal (especially yeast), animal (especially mammalian, including human) and plant) cells, comprising obtaining a cell to be dried, contacting the cell with one or more stabilizers (e.g., a polysaccharide such as trehalose), forming an aqueous suspension comprising the cell, and spray-drying the cell suspension under conditions favoring the production of a dried powder. The invention also relates to dried cell powders produced by these methods.

The invention further relates to methods of preparing sterile powdered culture media, media supplements, media subgroups and buffers. One such method comprises exposing the above-described powdered culture media, media supplements, media subgroups and buffers to γ irradiation such that bacteria, fungi, spores and viruses that may be resident in the powders are rendered incapable of replication. In a preferred such method, the powdered media, media supplements, media subgroups and buffers are γ irradiated at a total dosage of about 10–100 kilograys (kGy), preferably a total dosage of about 15–75 kGy, 15–50 kGy, 15–40 kGy or 20–40 kGy, more preferably a total dosage of about 20–30 kGy, and most preferably a total dosage of about 25 kGy, for about 1 hour to about 7 days, preferably for about 1 hour to about 5 days, more preferably for about 1 hour to about 3 days, about 1 hour to about 24 hours or about 1–5 hours, and most preferably about 1–3 hours. The invention also relates to sterile powdered culture media, media supplements, media subgroups and buffers produced by these methods.

The invention further provides methods of culturing a cell comprising reconstituting the nutritive media, media supplement, media subgroup or buffer of the invention with a solvent, which preferably comprises serum or water, and contacting the cell with the reconstituted nutritive media, media supplement, media subgroup or buffer under conditions favoring the cultivation of the cell. Any cell may be cultured according to the present methods, particularly bacterial cells, yeast cells, plant cells or animal cells. Preferable animal cells for culturing by the present methods include insect cells (most preferably Drosophila cells, Spodoptera cells and Trichoplusa cells), nematode cells (most preferably *C. elegans* cells) and mammalian cells (most preferably CHO cells, COS cells, VERO cells, BHK cells, AE-1 cells, SP2/0 cells, L5.1 cells, hybridoma cells or human cells). Cells cultured according to this aspect of the invention may be normal cells, diseased cells, transformed cells, mutant cells, somatic cells, germ cells, stem cells, precursor cells or embryonic cells, any of which may be established cell lines or obtained from natural sources.

The invention is further directed to kits for use in the cultivation of a cell. Kits according to the invention may comprise one or more containers containing one or more of the nutritive media powders, media supplement powders, media subgroup powders or buffer powders of the invention, or any combination thereof. The kits may also comprise one or more cells or cell types, including the dried cell powders of the invention.

Other preferred embodiments of the present invention will be apparent to one of ordinary skill in light of the following drawings and description of the invention, and of the claims.

BRIEF DESCRIPTION OF THE DRAWINGS

FIG. 16 is a series of line graphs indicating the effect of γ irradiation on the ability of transferrin to support the growth of 293 cells over four passages. In each graph, cells were cultured in standard serum-free 293 medium (♦), in medium without transferrin (■), in medium containing powdered transferrin that had been γ irradiated at −70° C. (▲) or room temperature (*), or in medium containing powdered transferrin that had not been γ irradiated but that had been stored at −70° C. (✻) or at room temperature (●). Results for each data point are the averages of duplicate flasks.

FIG. 17 is a series of bar graphs indicating the effect of γ irradiation, under different irradiation conditions, on the ability of FBS to support growth of anchorage-independent cells (FIGS. 17A and 17B) and anchorage-dependent cells (FIGS. 17C and 17D) at first (Px1), second (Px2) and third (Px3) passages.

FIG. 17B: AE-1 cells;

FIG. 17C: VERO cells;

DETAILED DESCRIPTION OF THE INVENTION

Definitions

Figure 1B:
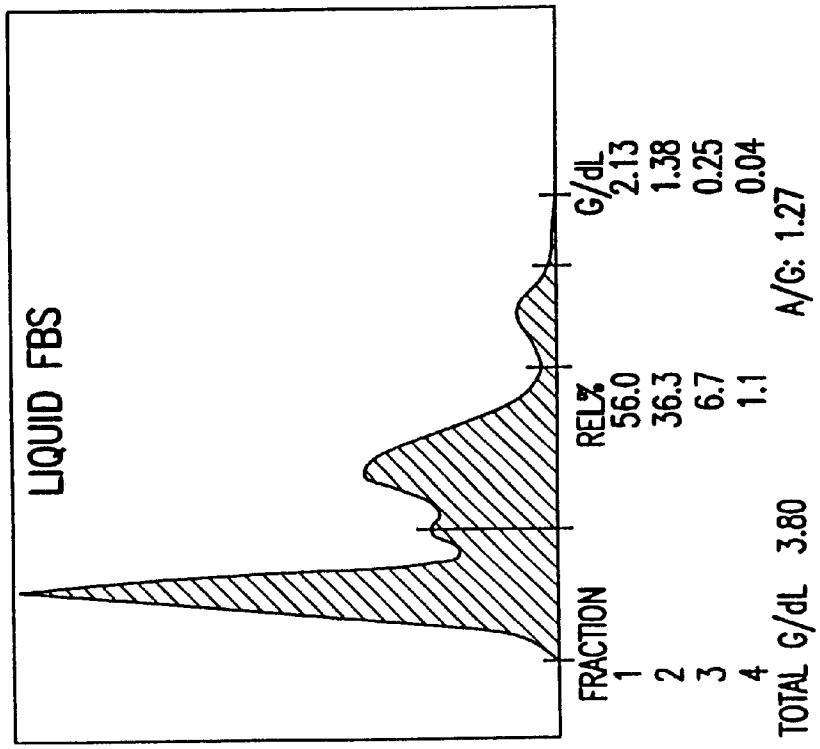
FIG. 1 is a histogram of a densitometric scan of SDS-PAGE of samples of fetal bovine serum (FBS) prepared in powdered form by the methods of the invention (FIG. 1A) and conventional liquid FBS (FIG. 1B).

In the description that follows, a number of terms conventionally used in the field of cell culture media are utilized extensively. In order to provide a clear and consistent understanding of the specification and claims, and the scope to be given such terms, the following definitions are provided.

The term "powder" as used herein refers to a composition that is present in granular form, which may or may not be complexed or agglomerated with a solvent such as water or serum. The term "dry powder" may be used interchangeably with the term "powder;" however, "dry powder" as used herein simply refers to the gross appearance of the granulated material and is not intended to mean that the material is completely free of complexed or agglomerated solvent unless otherwise indicated.

The term "ingredient" refers to any compound, whether of chemical or biological origin, that can be used in cell culture media to maintain or promote the growth of proliferation of cells. The terms "component," "nutrient" and ingredient" can be used interchangeably and are all meant to refer to such compounds. Typical ingredients that are used in cell culture media include amino acids, salts, metals, sugars, lipids, nucleic acids, hormones, vitamins, fatty acids, proteins and the like. Other ingredients that promote or maintain cultivation of cells ex vivo can be selected by those of skill in the art, in accordance with the particular need.

The term "cytokine" refers to a compound that induces a physiological response in a cell, such as growth, differentiation, senescence, apoptosis, cytotoxicity or antibody secretion. Included in this definition of "cytokine" are growth factors, interleukins, colony-stimulating factors, interferons and lymphokines.

By "cell culture" or "culture" is meant the maintenance of cells in an artificial, e.g., an in vitro environment. It is to be understood, however, that the term "cell culture" is a generic term and may be used to encompass the cultivation not only of individual prokaryotic (e.g., bacterial) or eukaryotic (e.g., animal, plant and fungal) cells, but also of tissues, organs, organ systems or whole organisms, for which the terms "tissue culture," "organ culture," "organ system culture" or "organotypic culture" may occasionally be used interchangeably with the term "cell culture."

By "cultivation" is meant the maintenance of cells in an artificial environment under conditions favoring growth, differentiation or continued viability, in an active or quiescent state, of the cells. Thus, "cultivation" may be used interchangeably with "cell culture" or any of its synonyms described above.

By "culture vessel" is meant a glass, plastic, or metal container that can provide an aseptic environment for culturing cells.

The phrases "cell culture medium," "culture medium" (plural "media" in each case) and "medium formulation" refer to a nutritive solution that supports the cultivation and/or growth of cells; these phrases may be used interchangeably.

By "extract" is meant a composition comprising a concentrated preparation of the subgroups of a substance, typically formed by treatment of the substance either mechanically (e.g., by pressure treatment) or chemically (e.g., by distillation, precipitation, enzymatic action or high salt treatment).

By "enzymatic digest" is meant a composition comprising a specialized type of extract, namely one prepared by treating the substance to be extracted (e.g., plant components or yeast cells) with at least one enzyme capable of breaking down the components of the substance into simpler forms (e.g., into a preparation comprising mono- or disaccharides and/or mono-, di- or tripeptides). In this context, and for the purposes of the present invention, the term "hydrolysate" may be used interchangeably with the term "enzymatic digest."

The term "contacting" refers to the placing of cells to be cultivated into a culture vessel with the medium in which the cells are to be cultivated. The term "contacting" encompasses mixing cells with medium, pipetting medium onto cells in a culture vessel, and submerging cells in culture medium.

The term "combining" refers to the mixing or admixing of ingredients in a cell culture medium formulation.

A cell culture medium is composed of a number of ingredients and these ingredients vary from one culture medium to another. A "1×formulation" is meant to refer to any aqueous solution that contains some or all ingredients found in a cell culture medium at working concentrations. The "1×formulation" can refer to, for example, the cell culture medium or to any subgroup of ingredients for that medium. The concentration of an ingredient in a 1×solution is about the same as the concentration of that ingredient found in a cell culture formulation used for maintaining or cultivating cells in vitro. A cell culture medium used for the in vitro cultivation of cells is a 1×formulation by definition. When a number of ingredients are present, each ingredient in a 1×formulation has a concentration about equal to the concentration of those ingredients in a cell culture medium. For example, RPMI-1640 culture medium contains, among other ingredients, 0.2 g/L L-arginine, 0.05 g/L L-asparagine, and 0.02 g/L L-aspartic acid. A "1×formulation" of these amino acids contains about the same concentrations of these ingredients in solution. Thus, when referring to a "1×formulation," it is intended that each ingredient in solution has the same or about the same concentration as that found in the cell culture medium being described. The concentrations of ingredients in a 1×formulation of cell culture medium are well known to those of ordinary skill in the art. See Methods For Preparation of Media, Supplements and Substrate For Serum-Free Animal Cell Culture Allen R. Liss, N.Y. (1984), which is incorporated by reference herein in its entirety. The osmolality and/or pH, however, may differ in a 1×formulation compared to the culture medium, particularly when fewer ingredients are contained in the 1×formulation.

A "10×formulation" is meant to refer to a solution wherein each ingredient in that solution is about 10 times more concentrated than the same ingredient in the cell culture medium. For example, a 10×formulation of RPMI-1640 culture medium may contain, among other ingredients, 2.0 g/L L-arginine, 0.5 g/L L-asparagine, and 0.2 g/L L-aspartic acid (compare 1×formulation, above). A "10× formulation" may contain a number of additional ingredients at a concentration about 10 times that found in the 1×culture medium. As will be readily apparent, "20×formulation," "25×formulation," "50×formulation" and "100× formulation" designate solutions that contain ingredients at about 20-, 25-, 50- or 100- fold concentrations, respectively, as compared to a 1×cell culture medium. Again, the osmolality and pH of the media formulation and concentrated solution may vary. See U.S. Pat. No. 5,474,931, which is directed to culture media concentrate technology.

Overview

The present invention is directed to methods of producing nutritive media, media supplements, media subgroups or buffers. Nutritive media, media supplements and media subgroups produced by the present methods are any media, media supplement or media subgroup (serum-free or serum-containing) which may be used to support the growth of a cell, which may be a bacterial cell, a fungal cell (particularly a yeast cell), a plant cell or an animal cell (particularly an insect cell, a nematode cell or a mammalian cell, most preferably a human cell), any of which may be a somatic cell, a germ cell, a normal cell, a diseased cell, a transformed cell, a mutant cell, a stem cell, a precursor cell or an embryonic cell. Preferred such nutritive media include, but are not limited to, cell culture media, most preferably a bacterial cell culture medium, plant cell culture medium or animal cell culture medium. Preferred media supplements include, but are not limited to, undefined supplements such as extracts of bacterial, animal or plant cells, glands, tissues or organs (particularly bovine pituitary extract, bovine brain extract and chick embryo extract); and biological fluids (particularly animal sera, and most preferably bovine serum (particularly fetal bovine, newborn calf or normal calf serum), horse serum, porcine serum, rat serum, murine serum, rabbit serum, monkey serum, ape serum or human serum, any of which may be fetal serum) and extracts thereof (more preferably serum albumin and most preferably bovine serum albumin or human serum albumin). Medium supplements may also include defined replacements such as LipoMAX®, OptiMAb®, Knock-Out™ SR (each available from Life Technologies, Inc., Rockville, Md.), and the like, which can be used as substitutes for the undefined media supplements described above. Such supplements may also comprise defined components, including but not limited to, hormones, cytokines, neurotransmitters, lipids, attachment factors, proteins and the like.

Nutritive media can also be divided into various subgroups (see U.S. Pat. No. 5,474,931) which can be prepared by, and used in accordance with, the methods of the invention. Such subgroups can be combined to produce the nutritive media of the present invention.

By the methods of the present invention, any nutritive media, media supplement, media subgroup or buffer may be produced and stored for an extended period of time without significant loss of biological and biochemical activity. By "without significant loss of biological and biochemical activity" is meant a decrease of less than about 30%, preferably less than about 25%, more preferably less than about 20%, still more preferably less than about 15%, and most preferably less than about 10%, of the biological or biochemical activity of the nutritive media, media supplement, media subgroup or buffer when compared to a freshly made nutritive media, media supplement, media subgroup or buffer of the same formulation. By an "extended period of time" is meant a period of time longer than that for which a nutritive medium, supplement, subgroup or buffer is stored when prepared by traditional methods such as ball-milling. As used herein, an "extended period of time" therefore means about 1–36 months, about 2–30 months, about 3–24 months, about 6–24 months, about 9–18 months, or about 4–12 months, under a given storage condition, which may include storage at temperatures of about −70° C. to about 25° C., about −20° C. to about 25° C., about 0° C. to about 25° C., about 4° C. to about 25° C., about 10° C. to about 25° C., or about 20° C. to about 25° C. Assays for determining the biological or biochemical activity of a nutritive media, media supplement, media subgroup or buffer are well-known in the art and are familiar to one of ordinary skill.

Formulation of Media, Media Supplements, Media Subgroups and Buffers

Any nutritive media, media supplement, media subgroup or buffer may be prepared by the methods of the present invention. Particularly preferred nutritive media, media supplements and media subgroups that may be prepared according to the invention include cell culture media, media supplements and media subgroups that support the growth of animal cells, plant cells, bacterial cells or yeast cells. Particularly preferred buffers that may be prepared according to the invention include balanced salt solutions which are isotonic for animal cells, plant cells, bacterial cells or yeast cells.

Examples of animal cell culture media that may be prepared according to the present invention include, but are not limited to, DMEM, RPMI-1640, MCDB 131, MCDB 153, MDEM, IMDM, MEM, M199, McCoy's 5A, Williams' Media E, Leibovitz's L-15 Medium, Grace's Insect Medium, IPL-41 Insect Medium, TC-100 Insect Medium, Schneider's Drosophila Medium, Wolf & Quimby's Amphibian Culture Medium, cell-specific serum-free media (SFM) such as those designed to support the culture of keratinocytes, endothelial cells, hepatocytes, melanocytes, etc., F10 Nutrient Mixture and F12 Nutrient Mixture. Other media, media supplements and media subgroups suitable for preparation by the invention are available commercially (e.g., from Life Technologies, Inc.; Rockville, Md., and Sigma; St. Louis, Mo.). Formulations for these media, media supplements and media subgroups, as well as many other commonly used animal cell culture media, media supplements and media subgroups are well-known in the art and may be found, for example in the GIBCO/BRL Catalogue and Reference Guide (Life Technologies, Inc.; Rockville, Md.) and in the Sigma Animal Cell Catalogue (Sigma; St. Louis, Mo.).

Examples of plant cell culture media that may be prepared according to the present invention include, but are not limited to, Anderson's Plant Culture Media, CLC Basal Media, Gamborg's Media, Guillard's Marine Plant Culture Media, Provasoli's Marine Media, Kao and Michayluk's Media, Murashige and Skoog Media, McCown's Woody Plant Media, Knudson Orchid Media, Lindemann Orchid Media, and Vacin and Went Media. Formulations for these media, which are commercially available, as well as for many other commonly used plant cell culture media, are well-known in the art and may be found for example in the Sigma Plant Cell Culture Catalogue (Sigma; St. Louis, Mo.).

Examples of bacterial cell culture media that may be prepared according to the present invention include, but are not limited to, Trypticase Soy Media, Brain Heart Infusion Media, Yeast Extract Media, Peptone-Yeast Extract Media, BeefInfusion Media, Thioglycollate Media, Indole-Nitrate Media, MR-VP Media, Simmons' Citrate Media, CTA Media, Bile Esculin Media, Bordet-Gengou Media, Charcoal Yeast Extract (CYE) Media, Mannitol-salt Media, MacConkey's Media, Eosin-methylene blue (EMB) media, Thayer-Martin Media, Salmonella-Shigella Media, and Urease Media. Formulations for these media, which are commercially available, as well as for many other commonly used bacterial cell culture media, are well-known in the art and may be found for example in the DIFCO Manual (DIFCO; Norwood, Mass.) and in the Manual of Clinical Microbiology (American Society for Microbiology, Washington, DC).

Examples of fungal cell culture media, particularly yeast cell culture media, that may be prepared according to the present invention include, but are not limited to, Sabouraud Media and Yeast Morphology Media (YMA). Formulations for these media, which are commercially available, as well as for many other commonly used yeast cell culture media, are well-known in the art and may be found for example in the DIFCO Manual (DIFCO; Norwood, Mass.) and in the Manual of Clinical Microbiology (American Society for Microbiology, Washington, DC).

As the skilled artisan will appreciate, any of the above media of the invention may also include one or more additional components, such as indicating or selection agents (e.g., dyes, antibiotics, amino acids, enzymes, substrates and the like), filters (e.g., charcoal), salts, polysaccharides, ions, detergents, stabilizers, and the like.

In a particularly preferred embodiment of the invention, the above-described culture media may comprise one or more buffer salts, preferably sodium bicarbonate, at concentrations sufficient to provide optimal buffering capacity for the culture medium. According to one aspect of the invention, a buffer salt, such as sodium bicarbonate, may be added in powdered form to the powdered medium prior to, during or following agglomeration of the medium. In one example of this aspect of the invention, the sodium bicarbonate may be added to the culture medium prior to, during or following agglomeration with an appropriate solvent (such as water, serum or a pH-adjusting agent such as an acid (e.g., HCl at a concentration of 1M to 5M, preferably at 1M) or a base (e.g., NaOH at a concentration of 1M to 5M, preferably at 1M) such that, upon reconstitution of the agglomerated medium the culture medium is at the optimal or substantially optimal pH for cultivation of a variety of cell types. For example, bacterial cell culture media prepared by the present methods will, upon reconstitution, preferably have a pH of about 4–10, more preferably about 5–9 or about 6–8.5. fungal (e.g., yeast) cell culture media prepared by the present methods will, upon reconstitution, preferably have a pH of about 3–8, more preferably about 4–8 or about 4–7.5; animal cell culture media prepared by the present methods will, upon reconstitution, preferably have a pH of about 6–8 or about 7–8, more preferably about 7–7.5 or about 7.2–7.4; and plant cell culture media prepared by the present methods will, upon reconstitution, preferably have a pH of about 4–8, preferably about 4.5–7, 5–6 or 5.5–6. Of course, optimal pH for a given culture medium to be used on a particular cell type may also be determined empirically by one of ordinary skill using art-known methods.

In another example, one or more buffer salts, e.g., sodium bicarbonate, may be added directly to a powdered nutritive medium by agglomerating the buffer(s) into the medium using a fluid bed apparatus, or by spray-drying the buffer(s) onto a dry or agglomerated powdered medium (using a spray-drying apparatus as described below). In a related aspect, a pH-adjusting agent such as an acid (e.g., HCl) or a base (e.g., NaOH) may be added to a powdered nutritive medium, which may contain one or more buffer salts (such as sodium bicarbonate), by agglomeration of the pH-adjusting agent into the powdered nutritive medium in a fluid bed apparatus, by spray-drying the pH-adjusting agent onto the powdered or agglomerated nutritive medium, or by a combination thereof; this approach obviates the subsequent addition of a pH-adjusting agent after reconstitution of the powdered medium. Thus, the invention provides a powdered nutritive culture medium useful in cultivation or growth of cells in vitro that, upon reconstitution with a solvent (e.g., water or serum), has a pH that is optimal for the support of cell cultivation or growth without a need for adjustment of the pH of the liquid medium. This type of medium, defined herein as "automatically pH-adjusting medium," therefore obviates the time-consuming and error-prone steps of adding buffer(s) to the medium after reconstitution and adjusting the pH of the medium after dissolution of the buffer(s). For example, a mammalian cell culture medium prepared according to these methods may, upon reconstitution, have a pH of between about 7.1 to about 7.5, more preferably between about 7.1 to about 7.4, and most preferably about 7.2 to about 7.4 or about 7.2 to about 7.3. The preparation of one example of such an automatically pH-adjusting culture medium is shown in more detail below in Examples 3 and 6.

Examples of media supplements that may be prepared as powders by the present methods include, without limitation, animal sera (such as bovine sera (e.g., fetal bovine, newborn calf and calf sera), human sera, equine sera, porcine sera, monkey sera, ape sera, rat sera, murine sera, rabbit sera, ovine sera and the like), defined replacements such as LipoMAX®, OptiMAb®, Knock-Out™ SR (each available from Life Technologies, Inc., Rockville, Md.), hormones (including steroid hormones such as corticosteroids, estrogens, androgens (e.g., testosterone) and peptide hormones such as insulin, cytokines (including growth factors (e.g., EGF, aFGF, bFGF, HGF, IGF-1, IGF-2, NGF and the like), interleukins, colony-stimulating factors, interferons and the like), neurotransmitters, lipids (including phospholipids, sphingolipids, fatty acids, cholesterol and the like), attachment factors (including extracellular matrix components such as fibronectin, vitronectin, laminins, collagens, proteoglycans, glycosaminoglycans and the like), and extracts of animal tissues, organs or glands (such as bovine pituitary extract, bovine brain extract, chick embryo extract, bovine embryo extract, chicken meat extract, achilles tendon and extracts thereof) and the like). Other media supplements that may be produced by the present methods include a variety of proteins (such as serum albumins, particularly bovine or human serum albumins; immunoglobulins and fragments or complexes thereof; aprotinin; hemoglobin; haemin or haematin; enzymes (such as trypsin, collagenases, pancreatinin or dispase); lipoproteins; fetuin; ferritin; etc.), which may be natural or recombinant; vitamins; amino acids and variants thereof (including, but not limited to, L-glutamine and cystine), enzyme co-factors; polysaccharides; salts or ions (including trace elements such as salts or ions of molybdenum, vanadium, cobalt, manganese, selenium, and the like); and other supplements and compositions that are useful in cultivating cells in vitro that will be familiar to one of ordinary skill. These sera and other media supplements are available commercially (for example, from Life Technologies, Inc., Rockville, Md., and Sigma Cell Culture, St. Louis, Mo.); alternatively, sera and other media supplements described above may be isolated from their natural sources or produced recombinantly by art-known methods that will be routine to one of ordinary skill (see Freshney, R. I., *Culture of Animal Cells,* New York: Alan R. Liss, Inc., pp. 74–78 (1983), and references cited therein; see also Harlow, E., and Lane, D., *Antibodies: A Laboratory Manual,* Cold Spring Harbor, N.Y.: Cold Spring Harbor Laboratory, pp. 116–120 (1988)).

Examples of buffers that may be prepared according to the present invention include, but are not limited to, phosphate-buffered saline (PBS) formulations, Tris-buffered saline (TBS) formulations, HEPES-buffered saline (HBS) formulations, Hanks' Balanced Salt Solutions (HBSS), Dulbecco's PBS (DPBS), Earle's Balanced Salt Solutions, Puck's Saline Solutions, Murashige and Skoog Plant Basal Salt Solutions, Keller's Marine Plant Basal Salt Solutions, Provasoli's Marine Plant Basal Salt Solutions, and Kao and Michayluk's Basal Salt Solutions. Formulations for these buffers, which are commercially available, as well as for many other commonly used buffers, are well-known in the art and may be found for example in the GIBCO/BRL Catalogue and Reference Guide (Life Technologies, Inc.; Rockville, Md), in the DIFCO Manual (DIFCO; Norwood, Mass.), and in the Sigma Cell Culture Catalogues for animal and plant cell culture (Sigma; St. Louis, Mo.).

Preparation of Powdered Media, Media Supplements, Media Subgroups and Buffers

The methods of the present invention provide for the preparation of the above-described powdered nutritive media, media supplements, media subgroups and buffers. These powdered media, supplements, subgroups and buffers are preferably prepared using fluid bed technology (i.e., "agglomeration") and/or via spray-drying.

In one aspect of the invention, the powdered nutritive media, media supplements, media subgroups and buffers are prepared using fluid bed technology to agglomerate the solutions of media, media supplements, media subgroups or buffers, thereby producing their dry powdered forms. Fluid bed technology is a process of producing agglomerated powders having altered characteristics (particularly, for example, solubility) from the starting materials. In general applications of the technology, powders are suspended in an upwardly moving column of air while at the same time a controlled and defined amount of liquid is injected into the powder stream to produce a moistened state of the powder; mild heat is then used to dry the material, producing an agglomerated powder.

Apparatuses for producing and/or processing particulate materials by fluid bed technology are available commercially (e.g., from Niro, Inc./Aeromatic-Fielder; Columbia, Md.), and are described, for example, in U.S. Pat. Nos. 3,771,237; 4,885,848; 5,133,137; 5,357,688; and 5,392,531; and in WO 95/13867; the disclosures of all of the foregoing patents and applications are incorporated by reference herein in their entireties. Such apparatuses have been used to prepare agglomerated powders of various materials, including milk whey (U.S. Pat. No. 5,006,204), acidulated meat emulsions (U.S. Pat. No. 4,511,592), proteases (U.S. Pat. No. 4,689,297) and other proteins (DK 167090 B1), and sodium bicarbonate (U.S. Pat. No. 5,325,606).

According to this aspect of the invention, fluid bed technology may be used to prepare bulk agglomerated nutritive media, media supplements, media subgroups and buffers. In the practice of this aspect of the invention, a dry powdered nutritive medium, medium supplement or buffer is placed into a fluid bed apparatus and is subjected to agglomeration therein. Powdered nutritive media (particularly powdered cell culture media), powdered media supplements (particularly powdered animal sera) and powdered buffers (particularly powdered buffered salines), may be obtained pre-made from commercial sources (e.g., Life Technologies, Inc.; Rockville, Md.). Alternatively, powdered nutritive media, media supplements, media subgroups or buffers may be made by admixing individual components or sets of components according to the formulations described above. Such formulations may include components which typically are not present in powdered nutritive media, media supplement, media subgroup and buffer formulations due to their instability, such as serum, L-glutamine, cystine, insulin, transferrin, lipids (particularly phospholipids, sphingolipids, fatty acids and cholesterol), cytokines (particularly growth factors, interleukins, colony-stimulating factors and interferons), neurotransmitters and buffers (particularly sodium bicarbonate). If L-glutamine is added to the formulation, it may be in the form of a complex with divalent cations such as calcium or magnesium (see U.S. Pat. No. 5,474,931). In another example, two or more powdered components may be admixed and then agglomerated to produce complex media, media supplements, media subgroups or buffers. For example, a powdered nutritive medium may be mixed with a powdered serum (produced, for example, by spray-drying as described below) such as FBS at a serum concentration of about 0.1%, 0.2%, 0.5%, 1%, 2%, 2.5%, 5%, 7.5%, 10%, 15%, 20%, 25%, 50% or higher (w/w as a percentage of the powdered medium); the resulting powdered medium-serum mixture may then be agglomerated to produce an agglomerated medium-serum complex that will readily dissolve in a reconstituting solvent and thus be ready for use without further supplementation.

Once the powdered nutritive media, media supplement, media subgroup or buffer (or mixture thereof) is placed into the fluid bed apparatus, it is subjected to suspension in an upwardly moving column of a gas, preferably atmospheric air or an inert gas such as nitrogen, and is passed through one or more particle filters. Since most dry powder, non-agglomerated nutritive media, media supplements, media subgroups and buffers are of a relatively small particle size, filters to be used in the invention should be mesh screens that allow air to flow through but that retain the powders, for example filters of about 1–100 mesh, preferably about 2–50 mesh, more preferably about 2.5–35 mesh, still more preferably about 3–20 mesh or about 3.5–15 mesh, and most preferably about 4–6 mesh.

After placement within the fluid bed chamber, the dry powder nutritive media, media supplement, media subgroup or buffer (or mixture thereof) is then subjected to agglomeration by injecting, preferably using a spray nozzle on the fluid bed apparatus, a defined and controlled amount of solvent into the powder, to produce a moistened powder. Preferred solvents for use in the present invention are any solvent that is compatible with the formulation of the nutritive media, media supplement, media subgroup or buffer. By "compatible" is meant that the solvent does not induce irreversible deleterious changes in the physical or performance characteristics of the nutritive media, media supplement, media subgroup or buffer, such as breakdown or aggregation of the nutrient components of the nutritive medium or changes in the ionic characteristics of the buffer. Particularly preferred solvents for use in the invention are water (most particularly distilled and/or deionized water), serum (particularly bovine or human serum and most particularly fetal bovine serum or calf serum), organic solvents (particularly dimethylsulfoxide, acetone, ethanol and the like), any of which may contain one or more additional components (e.g., salts, polysaccharides, ions, detergents, stabilizers, etc.).

In some aspects of the invention, it may be desirable or advantageous to include in the solvent one or more ingredients that, due to the concentrations of the components required in the final product, cannot be optimally incorporated into the product by other methods such as ball-milling. In one such aspect, the component may be dissolved, suspended, colloided or otherwise introduced into the solvent at the desired concentration, prior to use of the solvent in agglomeration of the powdered media, media supplement, media subgroup or buffer of the invention. Components that may be advantageously incorporated into the solvent in accordance with this aspect of the invention include, but are not limited to, one or more of the above-described sera, hormones, cytokines, neurotransmitters, lipids, attachment factors, proteins, amino acids, vitamins, enzyme cofactors, polysaccharides, salts, ions, buffers and the like.

The solvent should be introduced into the dry powder in a volume that is dependent upon the mass of powdered media, media supplement, media subgroup or buffer to be agglomerated. Preferred volumes of solvent per 500 grams of nutritive media, media supplement, media subgroup or buffer are about 5–100 ml, more preferably about 10–50 ml, still more preferably about 25–50 ml, and most preferably about 35 ml. Preferred solvent introduction rates per 500 grams of nutritive media, media supplement, media subgroup or buffer are a rate of about 1–10 ml/min, preferably about 2–8 ml/min, more preferably about 4–8 ml/min and most preferably about 6 ml/min. In some situations, it may be desirable to cycle between adding solvent for about one minute and then not adding solvent for about one minute (allowing drying of the powder within the apparatus chamber), so as to prevent clumping of the powder during agglomeration.

Once agglomeration of the powder is complete, as evidenced by a larger particle size than that of the original, unagglomerated powder and by the absence of fine dust particles in the agglomerated powder, the powder is thoroughly dried in the apparatus. Preferred apparatus temperatures for drying of the agglomerated powder are about 50–80° C., more preferably about 55–75° C., and most preferably about 60–65° C.; powder is preferably dried in the apparatus for about 3–10 minutes and most preferably for about 5–7 minutes, per 500 grams of powder.

In another aspect of the invention, powdered nutritive media, media supplements, media subgroups and buffers may be prepared by spray-drying. In this aspect of the invention, the nutritive media, media supplements, media subgroups and buffers in their liquid forms are placed into a spray-drying apparatus; these liquids are then converted into their corresponding powders by spraying the solution into a chamber in the apparatus under appropriate conditions to produce the powders, such as under controlled temperature and humidity, until the powders are formed. In some situations, it may be desirable or advantageous to spray-dry complex mixtures of two or more of the above-described media, media supplements, media subgroups and/or buffers. For example, liquid nutritive media containing animal sera at a desired concentration, or liquid animal sera containing nutritive media components at desired concentrations, may be mixed and then prepared as spray-dried powders according to the methods of the invention.

In a typical spray-drying approach, the liquid nutritive media, media supplements, media subgroups and buffers are aspirated into the apparatus and are atomized into a spray with a rotary- or nozzle-type atomizer. The resulting atomized liquid spray is then mixed with a gas (e.g., nitrogen or more preferably air) and sprayed into a drying chamber under conditions sufficient to promote production of a powdered product. In a preferred aspect of the invention, these conditions may comprise electronic control of the temperature and humidity within the chamber such that final drying of the product is promoted. Under these conditions, the solvent in the liquid evaporates in a controlled manner, thereby forming free-flowing particles (i.e., powder) of the nutritive media, media supplements, media subgroups or buffers of the invention. The powder is then discharged from the drying chamber, passed through one or more filters (such as the mesh screens described above for fluid bed preparation) and collected for further processing (e.g., packaging, sterilization, etc.). In some applications, particularly when producing powders from heat-sensitive formulations of nutritive media, media supplements, media subgroups and buffers, the spray-drying apparatus may be combined with a fluid bed apparatus integrated within the drying chamber, which allows the introduction of agglomerating solvents such as those described above into the spray-dried powder to produce agglomerated spray-dried powdered nutritive media, media supplements, media subgroups and buffers.

Apparatuses for producing particulate materials from liquid materials by spray-drying (with or without integrated fluid bed technology) are available commercially (e.g., from Niro, Inc./Aeromatic-Fielder; Columbia, Md.), and are described, for example, in the "Spray Drying," "Powdered Pharmaceuticals by Spray Drying" and "Fresh Options in Drying" technical brochures of Niro, Inc./Aeromatic-Fielder, the disclosures of which are incorporated by reference herein in their entireties. According to this manufacturer, such apparatuses have been used to prepare powders of various materials, including dairy products, analgesics, antibiotics, vaccines, vitamins, yeasts, vegetable protein, eggs, chemicals, food flavorings and the like. In the present invention, spray-drying has been found to be particularly useful for the preparation of powdered media supplements, such as sera and in particular those sera described above, most particularly human and bovine sera (such as fetal bovine serum and calf serum).

In the practice of this aspect of the invention, the liquid nutritive media, media supplements, media subgroups, buffers or pH-adjusting agents should be sprayed into the chamber through the atomizer at a spray rate of about 25–100 g/min, preferably at a spray rate of about 30–90 g/min, 35–85 g/min, 40–80 g/min, 45–75 g/min, 50–75 g/min, 55–70 g/min, or 60–65 g/min, and more preferably at about 65 g/min. The inlet air temperature in the atomizer is preferably set at about 100–300° C., more preferably at about 150–250° C., and most preferably at about 200° C., with an outlet temperature of about 50–100° C., more preferably about 60–80° C., and most preferably about 70° C. Air flow in the atomizer is preferably set at about 50–100 kg/hr, more preferably about 75–90 kg/hr, and most preferably about 80.0 kg/hr, at a nozzle pressure of about 1–5 bar, more preferably about 2–3 bar, and most preferably about 2.0 bar. These conditions and settings have been found in the present invention to be preferable for production of a variety of nutritive media, media supplements, media subgroups and buffer powders by spray-drying, particularly for the production of the above-described powdered sera. Following drying, the spray-dried powdered nutritive media, media supplements, media subgroups or buffers may be collected in the drying chamber through one or more filters, preferably such as those described above for fluid bed technology.

Following this preparation, the powders of the invention prepared by the above-described fluid bed or spray-drying methods have altered physical characteristics from the starting powders or from powdered media, supplements, subgroups and buffers prepared by lyophilizing the corresponding liquids. For example, non-processed or lyophilized powders often produce significant dust when used, and dissolve poorly or slowly in various solvents, while agglomerated or spray-dried powders are substantially dust-free and/or dissolve rapidly. Typically, the powdered media, media supplements, media subgroups and buffers of the invention will exhibit both reduced dusting and more rapid dissolution than their powdered counterparts prepared by standard techniques such as ball-milling. In some powders which are substantially dust-free but which may not demonstrate enhanced dissolution, the powders may be rapidly dissolved by rapid mechanical solvation of the powder, such as using a mechanical impeller, or by first providing a solvent mist over the powder such as by spray solvation.

In another aspect of the invention, the spray-drying and agglomeration approaches described above may be combined to produce agglomerated spray-dried nutritive media, media supplement, media subgroup and buffer powders. In this aspect, a powdered medium, supplement, subgroup or buffer that has been prepared by spray-drying may, after having been spray-dried, then be agglomerated with a solvent (such as those described above) to further improve the performance and physical characteristics of the resultant medium, supplement, subgroup or buffer. For example, an animal serum powder may be prepared by spray-drying liquid animal serum as described above, and this spray-dried serum powder may then be mixed into dry powder nutritive media (prepared by spray-drying or by standard techniques such as ball-milling); this mixed powder may then be agglomerated as described above. Alternatively, a spray-dried nutritive medium, medium supplement, medium subgroup or buffer powder may be agglomerated as above, to improve the dissolution properties of the powder. This approach may be particularly advantageous when spray-drying liquids with low (about 1–10%) solids content, such as liquid animal sera. As one of ordinary skill will appreciate, these approaches will facilitate preparation of a large batch of one or more components (e.g., sera or other media supplements) to be used as a stock for addition to a powdered medium, supplement, subgroup or buffer at a desired concentration, while also obtaining the above-described benefits of agglomeration. In addition, this approach may reduce inter-lot variability which may be a problem with certain media supplements (particularly animal sera).

The agglomerated or spray-dried powdered nutritive media, media supplements, media subgroups or buffers prepared as described above may then be packaged, for example into containers such as vials, tubes, bottles, bags, pouches, boxes, cartons, drums and the like, prior to or following sterilization as described below. In one such aspect of the invention, the powdered media, media supplements, media subgroups or buffers may be packaged into a compact, vacuum-packed form, such as that known in the art as a "brick-pack" wherein the powder is packaged into a flexible container (such as a bag or a pouch) that is sealed while being evacuated. Such packages may advantageously comprise one or more access ports (such as valves, luer-lock ports, etc.) allowing the introduction of a solvent (e.g., water, sera, media or other aqueous or organic solvents or solutions) directly into the package to facilitate rapid dissolution of the powder. In a related aspect, the package may comprise two or more adjacent compartments, one or more of which may contain one or more of the dry powder media, media supplements, media subgroups or buffers of the invention and one or more other of which may contain one or more aqueous or organic solvents which may be sterile. In this aspect, the dry powder may then be dissolved by simply removing or breaking the barrier between the compartments, ideally without loss of sterility, to allow admixture of the powder and the solvent such that the powder dissolves and produces a sterile nutritive medium, medium supplement, medium subgroup or buffer at a desired concentration.

Packaged media, media supplements, media subgroups and buffers of the invention are preferably stored for the extended times, and at the temperatures, noted above, typically for about 1–24 months at temperatures of less than about 30° C., more preferably at temperatures of less than about 20–25° C., until use. Unlike traditional powdered media, media supplements, media subgroups or buffers, storage at reduced temperatures (e.g., 0–4° C.) is not necessary for the maintenance of performance characteristics of the media, media supplements, media subgroups and buffers prepared by the present methods. Of course, other storage temperatures may be required for those aspects of the invention where the packages also comprise separate compartments containing one or more solvents; in these cases, the optimal storage conditions will be dictated by the storage requirements of the solvent(s) which will be known to the skilled artisan.

Sterilization and Packaging

The invention also provides methods for sterilizing the nutritive media, media supplements, media subgroups and buffers of the invention, as well as for sterilizing powdered nutritive media, media supplements, media subgroups and buffers prepared by standard methods such as ball-milling or lyophilization. Since nutritive media, media supplements, media subgroups and buffers are usually prepared in large volume solutions and frequently contain heat labile components, they are not amenable to sterilization by irradiation or by heating. Thus, nutritive media, media supplements, media subgroups and buffers are commonly sterilized by contaminant-removal methods such as filtration, which significantly increases the expense and time required to manufacture such media, media supplements, media subgroups and buffers.

Powdered nutritive media, media supplements, media subgroups and buffers prepared according to the methods of the invention (e.g., by spray-drying of liquid media, media supplements, media subgroups or buffers, or by agglomeration of powdered media, media supplements, media subgroups or buffers), or by standard methods such as ball-milling (of powdered components) or lyophilization (of liquid forms of the media, supplements, subgroups or buffers), however, can be sterilized by less expensive and more efficient methods. For example, powdered nutritive media, media supplements, media subgroups or buffers (prepared as described above by spray-drying or lyophilization of a liquid form, or by agglomeration of a powdered form, of the media, supplements, subgroups or buffers) may be irradiated under conditions favoring sterilization of these powders. Preferably, this irradiation is accomplished in bulk (i.e., following packaging of the nutritive media, media supplement, media subgroup or buffer), and most preferably this irradiation is accomplished by exposure of the bulk packaged media, media supplement, media subgroup or buffer of the invention to a source of gamma rays under conditions such that bacteria, fungi, spores or viruses that may be resident in the powdered media, media supplements, media subgroups or buffers are inactivated (i.e., prevented from replicating). Alternatively, irradiation may be accomplished by exposure of the powdered media, media supplement, media subgroup or buffer, prior to packaging, to a source of gamma rays or a source of ultraviolet light. The media, media supplements, media subgroups and buffers of the invention may alternatively be sterilized by heat treatment (if the subgroups of the nutritive media, media supplement, media subgroup or buffer are heat stable), for example by flash pasteurization or autoclaving. As will be understood by one of ordinary skill in the art, the dose of irradiation or heat, and the time of exposure, required for sterilization depend upon the bulk of the materials to be sterilized.

In a particularly preferred aspect of the invention, the bulk powdered nutritive media, media supplements, media subgroups or buffers are exposed to a source of $\gamma$ irradiation at a total dosage of about 10–100 kilograys (kGy), preferably a total dosage of about 15–75 kGy, 15–50 kGy, 15–40 kGy or 20–40 kGy, more preferably a total dosage of about 20–30 kGy, and most preferably a total dosage of about 25 kGy, for about 1 hour to about 7 days, more preferably about 1 hour to about 5 days, 1 hour to about 3 days, about 1–24 hours or about 1–5 hours, and most preferably about 1–3 hours ("normal dose rate"). Alternatively, the bulk powders of the invention may be sterilized at a "slow dose rate" of a total dosage of about 25–100 kGy over a period of about 1–5 days. During irradiation, the powdered nutritive media, media supplements, media subgroups or buffers are preferably stored at a temperature of about −70° C. to about room temperature (about 20–25° C.), most preferably at about −70° C. One of ordinary skill will appreciate, of course, that radiation dose and exposure times may be adjusted depending upon the bulk and/or mass of material to be irradiated; typical optimal irradiation dosages, exposure times and storage temperatures required for sterilization of bulk powdered materials by irradiation or heat treatment are well-known in the art.

Following sterilization, unpackaged nutritive media, media supplements, media subgroups and buffers may be packaged under aseptic conditions, for example by packaging the media, media supplements, media subgroups or buffers into containers such as sterile tubes, vials, bottles, bags, pouches, boxes, cartons, drums and the like, or in the vacuum packaging or integrated powder/solvent packaging described above. Sterile packaged media, media supplements, media subgroups and buffers may then be stored for extended periods of time as described above.

Use of the Nutritive Media, Media Supplements, Media Subgroups and Buffers

The present invention thus provides powdered nutritive media, media supplements, media subgroups and buffers that are readily soluble in a rehydrating solvent and that are substantially dust free. For use, the agglomerated or spray-dried media, media supplement, media subgroup or buffer may be hydrated (or "reconstituted") in a volume of a solvent sufficient to produce the desired nutrient, electrolyte, ionic and pH conditions required for the particular use of the solvated media, media supplement, media subgroup or buffer. This reconstitution is particularly facilitated in the present invention, since the present media, media supplements, media subgroups and buffers will rapidly go into solution and will produce little if any dust or insoluble material, unlike lyophilized or ball-milled nutritive media, media supplements, media subgroups or buffers.

Preferred solvents for use in reconstituting the powdered nutritive media, media supplements, media subgroups and buffers of the invention include, but are not limited to, water (most particularly distilled and/or deionized water), serum (particularly bovine or human serum and most particularly fetal bovine serum or calf serum), organic solvents (particularly dimethylsulfoxide, acetone, ethanol and the like), or any combination thereof, any of which may contain one or more additional components (e.g., salts, polysaccharides, ions, detergents, stabilizers, etc.). For example, powdered media supplements (such as animal sera) and buffers are preferably reconstituted in water to a 1×final concentration, or optionally to a higher concentration (e.g., 2×, 2.5×, 5×, 10×, 20×, 25×, 50×, 100×, 500×, 1000×, etc.) for the preparation of stock solutions or for storage. Alternatively, powdered culture media may be reconstituted in a solution of media supplements (e.g., sera such as FBS) in water, such as those solutions wherein the media supplement is present at a concentration, for example, of 0.5%, 1%, 2%, 2.5%, 5%, 7.5%, 10%, 15%, 20%, 25%, 50%, or higher, vol/vol in the water.

Reconstitution of the powdered nutritive media, media supplements, media subgroups or buffers is preferably accomplished under aseptic conditions to maintain the sterility of the reconstituted media, media supplement, media subgroup or buffer, although the reconstituted media, media supplement, media subgroup or buffer may alternatively be sterilized, preferably by filtration or other sterilization methods that are well-known in the art, following rehydration. Following their reconstitution, media, media supplements, media subgroups and buffers should be stored at temperatures below about 10° C., preferably at temperatures of about 0–4° C., until use.

The reconstituted nutritive media, media supplements, media subgroups and buffers may be used to culture cells according to standard cell culture techniques which are well-known to one of ordinary skill in the art. In such techniques, the cells to be cultured are contacted with the reconstituted media, media supplement, media subgroup or buffer of the invention under conditions favoring the cultivation of the cells (such as controlled temperature, humidity, lighting and atmospheric conditions). Cells which are particularly amenable to cultivation by such methods include, but are not limited to, bacterial cells, yeast cells, plant cells and animal cells. Such bacterial cells, yeast cells, plant cells and animal cells are available commercially from known culture depositories, e.g., American Type Culture Collection (Rockville, Md.), Invitrogen (La Jolla, Calif.) and others that will be familiar to one of ordinary skill in the art. Preferred animal cells for cultivation by these methods include, but are not limited to, insect cells (most preferably Drosophila cells, Spodoptera cells and Trichoplusa cells), nematode cells (most preferably C. elegans cells) and mammalian cells (including but not limited to CHO cells, COS cells, VERO cells, BHK cells, AE-1 cells, SP2/0 cells, L5.1 cells, hybridoma cells and most preferably human cells such as 293 cells, PER-C6 cells and HeLa cells), any of which may be a somatic cell, a germ cell, a normal cell, a diseased cell, a transformed cell, a mutant cell, a stem cell, a precursor cell or an embryonic cell, and any of which may be an anchorage-dependent or anchorage-independent (i.e., "suspension") cell.

Cells

In another aspect, the invention relates to methods for producing dry cell powder compositions comprising one or more cells, and to dry cell powders produced by these methods. These methods thus produce cell-containing compositions wherein the cells are preserved and may be stored for extended periods of time until use. In this way, the methods of the invention overcome some of the drawbacks of traditional methods of cell preservation (e.g., freezing) such as the need for cyropreservation equipment and the use of certain cryopreservatives that may be toxic to the cells.

Methods according to this aspect of the invention may comprise one or more steps. For example, one such method may comprise obtaining one or more cells to be dried, forming an aqueous cell suspension by suspending the one or more cells in an aqueous solution, and spray-drying the cell suspension under conditions favoring the production of a dried powder. These methods may further comprise contacting the one or more cells with one or more stabilizing or preserving compounds (e.g., a polysaccharide, including but not limited to trehalose). The aqueous solution used to form the cell suspension preferably comprises one or more components, such as one or more of the above-described nutritive media, media supplements, media subgroups, salts or buffers. Preferably, the aqueous solution used to form the cell suspension is adjusted to optimal or substantially optimal tonicity and osmolality for the cell type being dried. The aqueous solution may optionally comprise one or more additional components, such as one or more polysaccharides, ions, detergents, stabilizing or preserving compounds (including trehalose), and the like. In aspects of the invention wherein the one or more cells are contacted with one or more stabilizing or preserving compounds, the stabilizing or preserving compounds may be incorporated into the aqueous solution used to form the aqueous cell suspension. Alternatively, the stabilizing or preserving compounds may be sprayed or agglomerated onto the dry cell powder after formation of the powder.

Once the dry cell powder has been formed by the above-described methods, the powder may optionally be agglomerated with a solvent according to methods described above for agglomeration of dry powders. Any solvent that is compatible with the cell type being dried may be used to agglomerate the dry cell powder, including but not limited to water, a nutritive medium solution, a nutritive medium supplement solution (including sera, particularly bovine sera (most particularly fetal bovine and calf sera) and human sera), a buffer solution, a salt solution, and combinations thereof.

A variety of cells may be dried according to the methods of the invention, including prokaryotic (e.g., bacterial) and eukaryotic (e.g., fungal (especially yeast), animal (especially mammalian, including human) and plant) cells, particularly those cells, tissues, organs, organ systems, and organisms described above. Once the dried cells have been produced, they may be packaged aseptically and stored for extended periods of time (e.g., several months to several years), preferably at temperatures of about 0–30° C., 4–25° C., 10–25° C., or 20–25° C. (i.e., "room temperature") until use. For use in preparing cultures of viable cells, the dry cell powder may be aseptically reconstituted, into a cell suspension comprising one or more viable cells, with an aqueous solvent (e.g., sterile water, buffer solutions, media supplements, culture media, or combinations thereof) and cultured according to standard art-known protocols. Alternatively, the dry cell powder may be reconstituted into a cell suspension where cell viability is not essential, for example for preparation of an immunogen to be used for immunization of an animal. In such cases, the dry cell powder may be reconstituted with any solvent that is compatible with standard immunization protocols, such as aqueous or organic solvents that may comprise one or more detergents, adjuvants, etc.

Kits

The dry powder media, media supplements, media subgroups, buffers and cells provided by the invention are ideally suited for preparation of kits. Such a kit may comprise one or more containers such as vials, test tubes, bottles, packages, pouches, drums, and the like. Each of the containers may contain one or more of the above-described nutritive media, media supplements, media subgroups or buffers of the invention, or combinations thereof Such nutritive media, media supplements, media subgroups or buffers may be hydrated or dehydrated but are typically dehydrated preparations produced by the methods of the invention. Such preparations may, according to the invention, be sterile.

A first container may contain, for example, a nutritive media, media supplement, media subgroup or a buffer of the invention, or any component or subgroup thereof, such as any of those nutritive media, media supplements, media subgroups or buffers of the invention that are described above. Additional nutritive media, buffers, extracts, supplements, components or subgroups may be contained in additional containers in the present kits. The kits may also contain, in one or more additional containers, one or more cells such as the above-described bacterial cells, yeast cells, plant cells or animal cells. Such cells may be lyophilized, dried, frozen or otherwise preserved, or may be spray-dried according to the methods of the invention. In addition, the kits of the invention may further comprise one or more additional containers, containing, for example, L-glutamine, optionally complexed with one or more divalent cations (see U.S. Pat. No. 5,474,931). The kits may further comprise one or more additional containers containing a solvent to be used in reconstituting the dry powder nutritive media, media supplements, media subgroups and/or buffers; such solvents may be aqueous (including buffer solutions, saline solutions, nutritive medium solutions, nutritive medium supplement solutions (including sera such as bovine sera (particularly fetal bovine sera or calf sera) or human sera), or combinations thereof) or organic. Other ingredients that are not compatible for admixture with the nutritive media, buffers, extracts, supplements, components or subgroups of the invention may be contained in one or more additional containers to avoid mixing of incompatible components.

The number and types of containers contained in a given kit for making a nutritive media, media supplement, media subgroup or buffer may vary depending on the type of media, media supplement, media subgroup or buffer to be prepared. Typically, the kit will contain the respective containers containing the components or supplements necessary to make a particular media, media supplement, media subgroup or buffer. However, additional containers may be included in the kit of the invention so that different media, media supplements, media subgroups or buffers can be prepared by mixing different amounts of various components, supplements, subgroups, buffers, solvents, etc., to make different media, media supplement, media subgroup or buffer formulations.

Advantages

Unexpectedly, the present invention provides for the preparation of nutritive media, media supplements, media subgroups, buffers and cells at reduced cost. The cost reductions are due to the several factors. For example, the media, media supplement, media subgroup and buffer formulations of the present invention may be produced with much smaller production facilities since the large stir tanks required for 1×formulations are not required. In addition, the media, media supplement, media subgroup and buffer formulations of the present invention may be prepared on an as needed basis using "just in time" production techniques which reduce inventory, storage and labor costs. The time required for the preparation and shipping of the media, media supplement, media subgroup and buffer formulations may be reduced from 6–8 weeks to as little as one day. The automatically pH-adjusting media of the invention also provide significant cost and time savings, and reduce the tendency for introduction of contamination into reconstituted media that may occur during the pH adjustment process according to standard methods using traditional dry powder or bulk liquid media. The present invention also allows for the preparation of components of nutritive media, media supplements, media subgroups or buffers which may be used to prepare very large quantities of 1×media, media supplements, media subgroups or buffers (e.g., 100,000 liters or more) which would require only one quality control test compared to multiple quality control tests for multiple batches produced according to other commonly used techniques. Importantly, the media, media supplement, media subgroup and buffer formulations of the present invention are more consistent between batches since the individual components are more stable. The dried cell powders of the invention are also technologically and economically advantageous, since the cells may be stored, in low volume, for extended periods of time with little need for specialized equipment beyond that typically available in the laboratory. In addition, the cells prepared by the present methods are preserved without being exposed to cryopreservative reagents which may be toxic to the cells.

It will be readily apparent to one of ordinary skill in the relevant arts that other suitable modifications and adaptations to the methods and applications described herein are obvious and may be made without departing from the scope of the invention or any embodiment thereof Having now described the present invention in detail, the same will be more clearly understood by reference to the following examples, which are included herewith for purposes of illustration only and are not intended to be limiting of the invention.

Example 1

Agglomeration of Typical Dry Powder Media (DPM)

1. With a benchtop laboratory fluid bed apparatus (Stera-1; Niro, Inc./Aeromatic-Fielder; Columbia, Md.): Place 100–500 g of DPM within the chamber. Place onto apparatus and use the lever to seal the unit.
2. Start the airflow to fluidize (levitate) the DPM. Since traditional DPM is of relatively fine particle size, setting 4–6 will be needed. Turn on the vacuum device to catch fine DPM particles, passing through the upper filters. Make sure that the fluidized powder is approximately central within the chamber with respect to the lower mesh screen and the upper filters.
3. Start the injection device (spray unit) by first plugging in the compressed air line and then by starting the pump which is connected to a water source. The goal is to admit ~6 ml of water per minute (the flow rate for any given pump based upon RPM and tubing diameter must be known). In order to prevent clumping of DPM, alternatively add water for ~1 minute and then stop for ~1 minute, allowing drying to occur in the chamber.
4. If filters become coated with DPM during the run so that blowback does not dislodge powder, turn fan speed down to setting 2–3 until all filters have been blown clear. Then increase running fan speed to previous level.
5. Agglomeration will be complete when ~35 ml of water has been added for each 500 g of DPM. This volume will vary depending upon the DPM formulation. A downward flow of relatively large agglomerated granules will be seen in the chamber (bottom) toward the end of the run. Visibly larger particles and absence of fine dust indicates that the process is complete.
6. Allow agglomerated DPM to dry thoroughly for 5–7 minutes.
7. At end of run, blow off filters 4 times.
8. Turn unit off, disconnect water tube and collect agglomerated DPM into an airtight container.

These approaches should be adjusted when using a process-scale or production-scale fluid bed apparatus. For example, when the MP-1 (Niro, Inc./Aeromatic-Fielder; Columbia, Md.) apparatus is used, the following protocol has yielded satisfactory results:

1. Seal unit (inflate gaskets).
2. Start fan for pre-heat.
3. Stop fan when inlet air temperature equals set point.
4. Deflate gaskets, load material, inflate gaskets.

Steps 5–8 should all be accomplished within one minute:

5. Start batch.
6. Start fan, and turn on filter cleaning.
7. Set nozzle atomizing air pressure % output (check nozzle for vacuum).
8. Connect liquid feed line.
9. Start pump on screen and at pump.
10. Reset batch time.
11. Spray all liquid at set rate (26 g/min). Use ~250 ml water for 2 kg powder.

12. Stop pump-at pump and on screen when all liquid is added.
13. Reduce airflow to drying value (for example from 100 to 60).
14. When product reaches desired temperature (~40° C.), go to "initial set up" screen and set "batch duration" for a value of 2–3 minutes greater than the present "batch time".
15. Stop batch.
16. Deflate gaskets.

Typical instrument settings (for bench-, process- and production-scale apparatuses):

Drying temperature: 60–65° C.
Outlet air temperature: ~33° C.
Blow out pressure: 5 bar
Atomizing pressure: 1.5–2.0 bar
Blow back dwell: 1 after spraying, 2 while spraying
Capacity of fan: 5 at start of run, 6 after agglomeration is evident
Magnahelics: Filter resistance 150–250, Resistance of perforated control plate ~50, Air volume: less than 50.

Example 2

Addition of Sodium Bicarbonate as an Integral Part of DPM

As noted above, sodium bicarbonate is not typically added to DPM during manufacturing by ball-milling or lyophilization, due to potential off-gassing and buffering capacity complications encountered upon storage of the powdered media. This standard production process thus necessitates the addition of sodium bicarbonate, and pH adjustment, upon reconstitution of the media. With the present methods, however, these additional steps may be obviated by adding the sodium bicarbonate (or any buffering salt) directly to the powdered medium during manufacturing.

There are two ways of including sodium bicarbonate (or any buffering salt) within the DPM: (a) via the injection device and (b) as part of the DPM.

(a) Injection Device

Because of the solubility of sodium bicarbonate and the amounts that generally need to be added to a typical mammalian cell culture medium, fairly large volumes of liquid would need to be injected into the powder (significantly greater than the 35 ml of water mentioned above). This is still possible and in fact may be preferable if adding another component that similarly requires a relatively large volume of liquid in order to be added to the DPM, as is the case with serum for example. In this case, care must be taken to sequentially add liquid, let dry etc. a number of times to insure that the DPM does not become clumped within the device. Using the 6 ml per minute for ~1 minute and then allowing drying for another 2 minutes is about right.

The amount of liquid to add is determined as follows: Prepare sodium bicarbonate at 75 g/L in water. Example: 250 g of DPM in the chamber to be agglomerated. Assume 10.0 g of DPM is required for 1 L of 1×liquid medium. Therefore, 250 g represents 25 L of 1×liquid medium. For each L of liquid, assume (for example) a requirement of 2 g of sodium bicarbonate. This means that 50 g of bicarbonate is needed. Now, since the bicarbonate solution is at 75 g/L, then 0.67 L of bicarbonate solution must be added to the 250 g of DPM.

The sodium bicarbonate solution would be added similarly to the process for "agglomeration of a typical DPM" above except that a longer drying time between cycles is needed since the pH of the sodium bicarbonate solution is ~8.00 which can degrade media components. It is important that the powder never become "soaked" by addition of bicarbonate solution too rapidly without allowing sufficient time for thorough drying of the bicarbonate powder between cycles. Also, longer fluid drying times are required since it is important to have as low a final moisture content as possible since moisture would result in liberation of carbon dioxide gas resulting in loss of buffering capacity and "pillow" formation if powder is in a foil packet.

(b) As part of the DPM

Sodium bicarbonate can be milled into the DPM in a similar fashion as for other media components prior to fluid bed treatment. However, in the milling process, the bicarbonate should be added as the final component. All of the other media components should be milled as usual and then the mill stopped and the bicarbonate added last, with further milling to reach proper sized particles. It is important that all post-milling processing (placement into containers, etc.) be done in a humidity-controlled environment set as low as operationally possible (~20–40%. Fluid bed processing should then be performed as soon as possible after milling. (If not processed the same day, DPM must be double wrapped and placed within a sealed container with moisture absorbents.)

The fluid bed process itself is done similarly to the example given above (with use of 35 ml per 500 g of DPM) except that drying times after water injection (~6 ml/min) should again be extended: 1 min of injection of water and 2 minutes drying cycles. It will be noted that the color of the DPM will be deep red-light purple due to presence of phenol red. Since the DPM has essentially no moisture content, this does not represent a degradative situation, and is why fluid bed processing is essential.

Example 3

DPM that Includes Buffering Salts (e.g., Sodium Bicarbonate) and is Formulated so that pH of Reconstituted (1×) Medium is Automatically of Desired pH with No User Efforts As noted above, all commercially available mammalian cell culture powdered media require addition of one or more buffer salts (e.g., sodium bicarbonate) when preparing 1×liquid, and then adjustment of pH, so that the solution will be at proper pH. The present methods, however, can be used to obviate both the addition of sodium bicarbonate (as described above in Example 2) and the need for pH adjustment. In this aspect of the invention, fluid bed technology is used to introduce acid or base (depending on the need) to a dry powder medium comprising one or more buffering salts. In accordance with this aspect of the invention, any buffering salts or combinations thereof, and any acid or base, may be used depending upon the desired pH and buffering capacity in the ultimately reconstituted cell culture medium.

If sodium bicarbonate is added directly to the DPM as a powder, it is possible for the end user to simply add water and mix to yield a solution already containing bicarbonate (see above) and of proper pH. It is necessary first to determine how much of a pH adjustment is required. (1) Place 1 L of water in a beaker. Add DPM to the liquid and mix. (Amount to add/L is given by the specifications for that powder, e.g., 10 g/L, 13 g/L). In this case, the weight of the sodium bicarbonate must also be considered in determining how much to add per liter. (2) After the powder has dissolved, add 5N HCl to adjust the solution to the desired pH. Record the amount. (3) Convert this number to amount of 1N HCl. Calculate how much 1N HCl is needed for adjustment of the total powder to be agglomerated. (Example: 5 ml of 1N HCl is needed to adjust 1 L of 1×medium A to pH 7.2 from the unadjusted pH of 7.9. That 1 L of 1×medium represents, for example, 13.0 g of DPM. Therefore, for each 13.0 g of DPM, 5 ml of 1N HCl is needed. If we want to adjust pH of 250 g of DPM, then 250 divided by 13.0=19.2×5 ml or 96 ml of 1N HCl is needed to be added to the powder to make it automatically pH-adjusted.

This 1N HCl must now be added to the DPM. The best way for that is to use the injection device, adding 1N HCl instead of water. In general, the protocol is similar to the above with the following exceptions: (1) the 1N HCl must be added slowly to the media which contains sodium bicarbonate. If it is added too quickly, carbon dioxide may be driven off, resulting in suboptimal buffering capacity. Because of the volume of 1N HCl generally required, several 1 minute on, 2 minute off cycles are needed. A dry powder state must be obtained at the end of each cycle so that a dynamic system exists where DPM has characteristics of a fluid process but in reality is a dried powder. (Amazingly, as HCl is added to the powder, the bulk color changes from dark reddish purple to light yellow-orange color even though the powder remains essentially dry at all times due to the continual evaporation within the system). Since the total amount of HCl has been calculated to yield an essentially neutral pH, the powder is never really exposed to "acid" conditions as long as the fluid bed is properly adjusted (see above; position of the powder particles within the chamber during operation). It is important to make sure that all of the powder is moving through the system (i.e., being lifted, agglomerated and settled continuously) and having no "dead" zones within the chamber.

Once the powder is collected after the run, it can be added to water and reconstituted at any time as long as it has been kept in proper "dry" packaging and location. No adjustment of pH is needed. Thus, the invention provides an automatic pH-adjusting dry powdered medium, where the pH of the liquid medium made by reconstituting the dry powdered medium requires no adjustment of pH.

Example 4

Inclusion of Large Molecular Weight Supplements Such as Serum, Albumin, Hy-Soy, etc., within the DPM Itself Heretofore, dried powder media containing serum have not been commercially available. Using the present methods (via fluid bed and spray-drying technologies), we have succeeded in adding serum to a powder in a manner where functionality (cell culture) is maintained.

The injection device of the fluid bed apparatus is able to form a mist with serum, and concentrated albumin. We attempted to see if serum added to the DPM and dried in this manner would be functional.

Procedure for addition of serum: (1) Determine the weight of standard DPM to be agglomerated. (2) From this, based upon the g/L for the particular powder, calculate the volume of 1×medium that the g of powder will make. (3) Calculate the volume of serum that would be needed at a given percentage level of supplementation (e.g., 100 g of powder to be used in 10 g/L yields 10 L-equivalents of powder). At 5% serum supplementation, 500 ml of serum would be required to be added by the injection device.

Protocol for addition of the serum: Serum and albumin are very viscous. The nozzle spray pattern must be checked for droplet size and pattern. With the sample tube in the solution to be added to the powder, test spray against a cardboard or other backdrop. Check for uniformity and small droplet size. If not a "mist," increase atomizing pressure by 0.5 bar and test again. Do this until sufficient pressure results in a fine mist pattern.

For use in cell culture applications, it is necessary to know the weight/ml of serum-DPM to be used per L of 1×medium. To do this, accurately weigh vials or test tubes that will hold the serum during drying. Place a constant (known) quantity of serum into each of the vials. Then place vials into a Speed Vac or lyophilizer. Remove water until dryness. Then weigh the vials again, this time containing lyophilized serum. Calculate the weight of serum and express as per ml of original volume. The weight of agglomerated DPM with serum to use per L will then be the standard DPM "use" weight plus the weight of the serum at a given level.

For example, assume that Medium A (DPM) is to be used at 10 g/l. Serum supplementation is to be at 5% v/v. This means that in addition to the weight of the standard DPM, the weight of the serum would equal 5%=50 ml to add per L of medium. Assume that serum powder weighs 0.06 g/ml. Then the weight of the powdered serum=50×0.06 g/L=3 g. Therefore, the weight of serum-containing DPM that would be added to 1 L of water is the weight of serum powder (3 g) plus the weight of the standard DPM (10 g) per liter=13 g/L.

Example 5

Reducing or Eliminating Milling Techniques (High Energy Input System That Break Components down to Micron-sized Particles) When Manufacturing a DPM As noted above, dry powdered medium typically is manufactured via the milling process, which is laborious and has a number of problems. The methods of the present invention provide for the production of a dry powdered medium using fluid bed technology, which overcomes these labor and technical constraints.

A. Blending first in external device, then fluid bed treatment

Normally milled DPM is blended with sodium bicarbonate (directly as received from the supplier, additional ball milling not needed). [RPM 1640 with sodium bicarbonate at 2 g/L-equivalents]. This mixture is blended for 20 minutes. The powder is then placed within the fluid bed chamber and fluidized as above for bicarbonate-containing media or bicarbonate-containing media with automatic pH control.

B. Blending directly in fluid bed chamber, then agglomeration

Sodium bicarbonate is placed into the chamber directly with the milled DPM and blended (mixed) for a brief period of time, to be followed with agglomeration. This eliminates blending in a separate unit.

C. Total elimination of the ball-milling process

Either all of the DPM chemicals are added directly to the fluid bed chamber and mixed preliminarily followed by agglomeration or, more likely, some of the coarser, "stickier", etc. chemicals are given a brief grinding treatment in a rotary grinder and then placed within the fluid bed for blending and final agglomeration.

Example 6

A Method for Having All of the above Characteristics Within this Same DPM

We have combined addition of "off the shelf" sodium bicarbonate with milled DPM and automatic pH control. We have also combined serum with DPM.

To combine serum with DPM containing sodium bicarbonate with automatic pH control, one protocol is to:

1. Add sodium bicarbonate (powder, from supplier) to DPM (milled or ground).
2. Blend ingredients (mix, either external unit or fluid bed).
3. In a separate vessel, reconstitute 1 L of the DPM (containing bicarbonate) with water (1×) and determine the amount of 1N HCl, or 1N NaOH that is required to adjust the pH of the solution to 7.5. On a liter basis, knowing the mass of powder to be agglomerated (and thus the L-equivalents), calculate the amount of 1N HCl or 1N NaOH for the total powder to be agglomerated at the above-calculated amount. Add this amount via fluid bed device (injection nozzle). (Although DPM is not "liquid," it is important to have a powder as close to neutrality as possible but not of such an acid pH that bicarbonate would be liberated when adding serum, since moisture is involved in the process. At pH 7.6 or higher, a concentrated solution of sodium bicarbonate will not evolve $CO_2$ gas, but at lower pH gas will be given off.)
4. Addition of serum (extended agglomeration), based upon percentage supplementation and g to be agglomerated.
5. Using the same 1 L of 1×liquid from (3) above, determine the amount of 1N HCl or 1N NaOH needed to adjust the pH to the desired pH (e.g., 7.2). Using this information, calculate the amount to be used for the weight of powder that has been agglomerated with serum (knowing g/L specifications). Add this amount via fluid device (injection nozzle).
6. Gamma irradiation is used to sterilize the powdered media.

In a similar method, a serum-containing DPM may be produced by combining a particular amount of DPM with a particular amount of powdered serum (prepared, e.g., by spray-drying as described in Example 8 below) and then agglomerating the mixture. For example, for preparation of medium containing 10% powdered FBS, 55.5 g powdered FBS may be added to 500 g of powdered culture medium and the powders mixed well by agitation. This mixture may then be water-agglomerated as described above, and will yield, upon reconstitution, a culture medium containing 10% FBS which may be auto-pH-adjusting.

Example 7

Production of 100% Serum Powder by Fluid Bed Processing (To Simulate Spray-Drying).

Methodology

1) We used the benchtop laboratory fluid bed apparatus (Strea-1). For production of powdered serum, nothing is placed within the chamber. The lever is used to seal the unit.
2) Serum was added by way of the injection device (spray unit). As the serum was added into the chamber, the air flow was increased enough and the flow of serum slowed enough that evaporation of water occurred and the serum was dried sufficiently so that powder formed instantly within the chamber. No moist or fluid coating existed anywhere within the chamber.
3) Pump speed was set to allow for ~1 ml/minute into the chamber.
4) Airflow speed was set to a setting of ~8–9.
5) To clean filters intermittently, fan speed was reduced to ~2–3. This was done routinely every 5–10 minutes. (The 8–9 airflow setting is so high that the filters will not blow off the powder and clean themselves).
6) After one round of filter blow-off, fan speed was increased to previous levels and the pump turned on. (Once these parameters were set, the pump was run continuously except when cleaning the filters as indicated).
7) After all of the serum liquid had been added into the agglomerator, final drying was performed over five minutes.
8) The filters were then blown off to collect as much powder as possible, and the machine shut off and product removed. Powdered serum was placed into an air-tight container and protected from light.

Typical instrument settings

Drying temperature: 60–65° C.

Outlet air temperature: ~33° C.

Blow out pressure: 5 bar

Atomizing pressure: 2.0–2.5 bar

Blow back dwell: 2, in between spraying

Capacity of fan: 8–9 throughout run

Magnahelics: Filter resistance—150–250, Resistance of perforated control plate—~50, Air volume—less than 50.

Figure 1A:
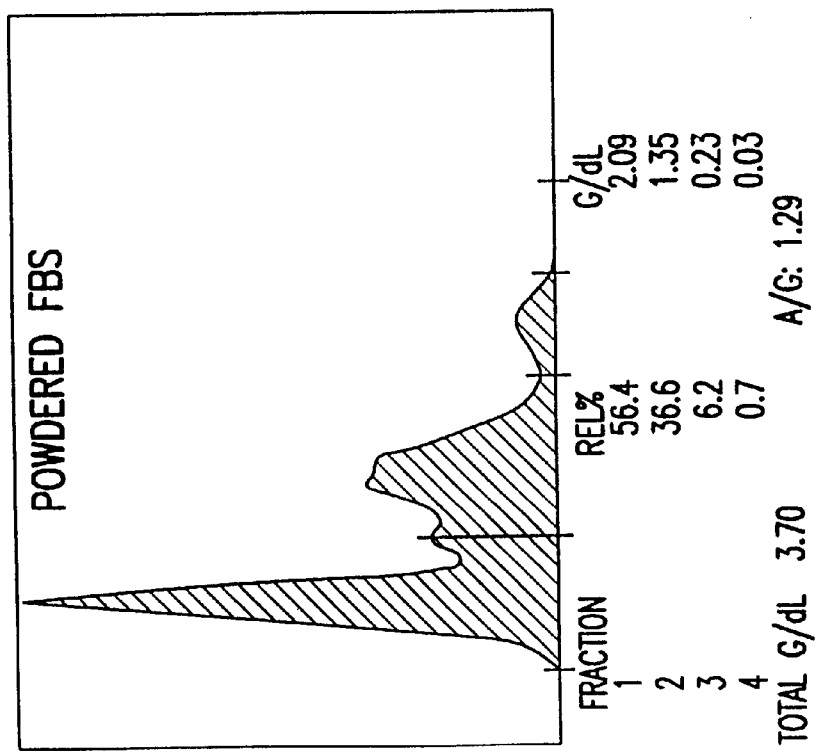

To determine if agglomeration of the FBS affected the protein structure or distribution, samples of agglomerated FBS and liquid FBS were run on SDS-PAGE, stained for protein and scanned densitometrically. As shown in FIG. 1, agglomerated FBS prepared according to the present methods (FIG. 1A) demonstrated a nearly identical protein profile to that observed with liquid FBS (FIG. 1B). These results indicate that the controlled production of dry powdered FBS by the present methods does not substantially affect the structure or distribution of the major components of the serum.

Figure 2A:
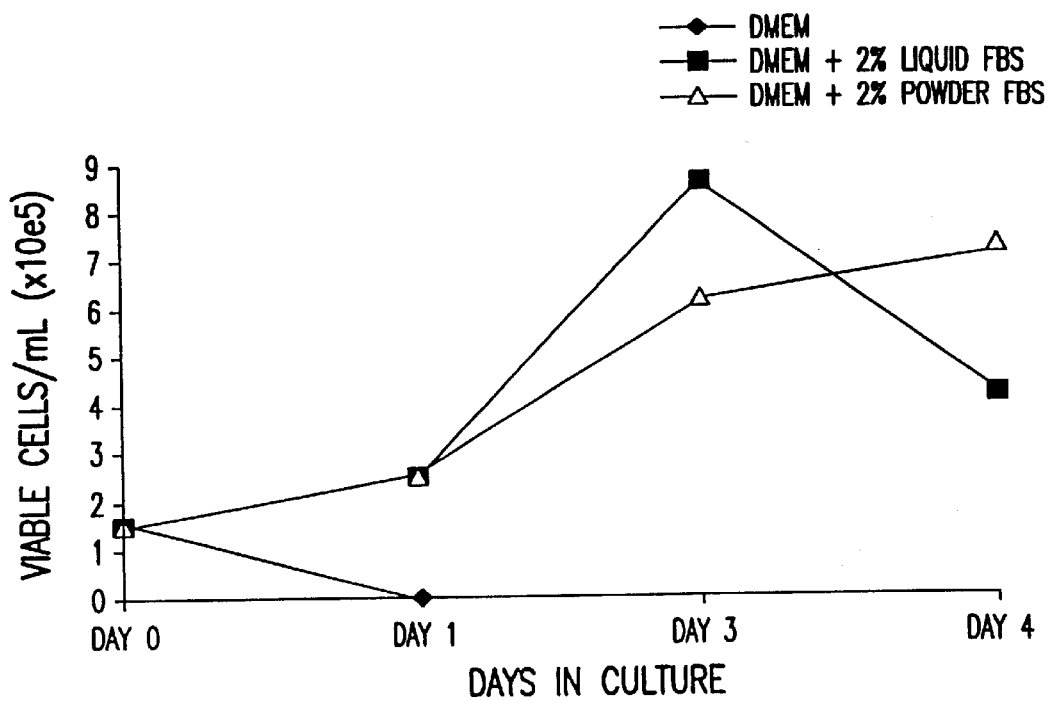
FIG. 2 is a composite of line graphs of growth (FIG. 2A) and passage success (FIG. 2B) of SP2/0 cells in Dulbecco's Modified Eagle's Medium (DMEM) supplemented with 2% (w/v) FBS prepared in powdered form by the agglomeration methods of the invention.
Figure 2B:
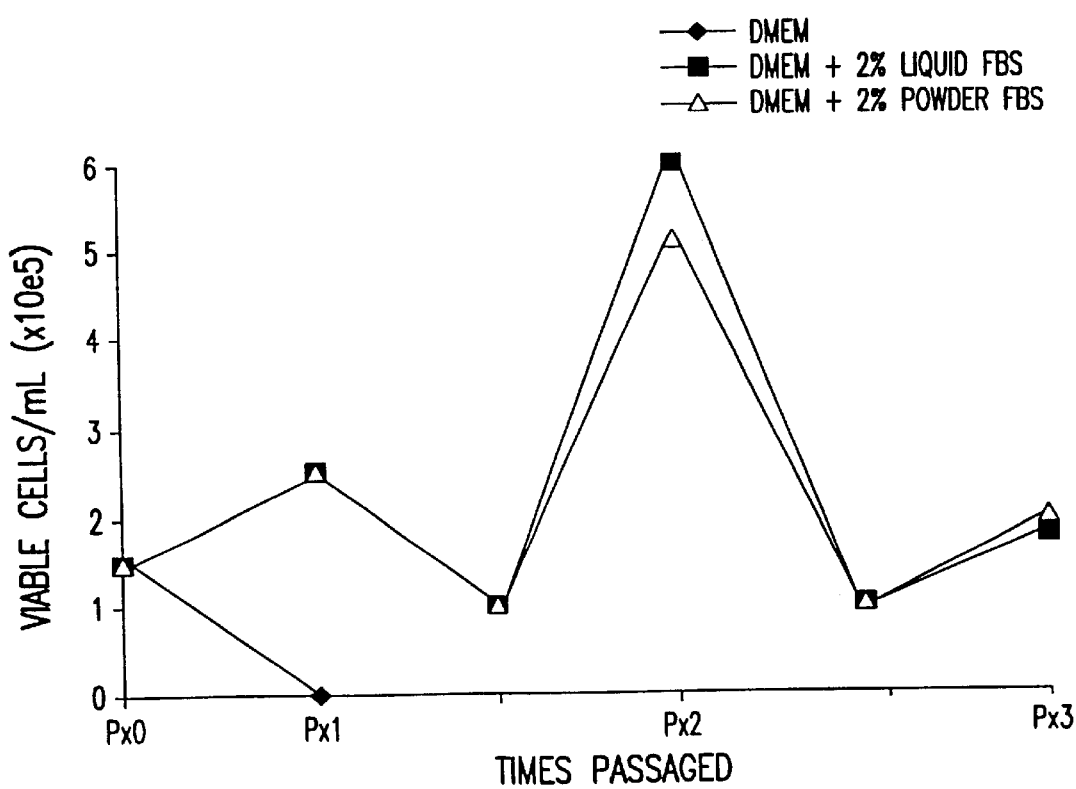

To determine if agglomeration of the FBS affected its ability to support cell growth and passage, SP2/0 cells were plated into DMEM containing either 2% agglomerated ("dry") FBS or 2% liquid FBS and growth rates and passage recovery examined. As shown in FIG. 2A, cells plated into media containing agglomerated FBS demonstrated similar growth kinetics as did cells plated into media containing liquid FBS. Similarly, cells in media containing agglomerated FBS recovered from passage with practically identical growth rates as cells in media containing liquid FBS (FIG. 2B). Together, these results indicate that the agglomerated FBS of the present invention performs approximately equivalently to liquid FBS in supporting growth and passage of cultured cells.

Example 8

Production of 100% Serum Powder by Spray-Drying

As an alternative to fluid bed processing, the feasibility of producing dry powdered serum by spray-drying technology was examined. A three foot diameter laboratory spray drier (Mobile Minor Spray Drier; NIRO, Columbia, Md.) was used to prepare the powdered serum. Liquid FBS was aspirated into the spray-dryer and atomized through a Schlick 940 nozzle located in the middle of the air dispenser, and the drying air was introduced into the atomizer through the top air dispenser of the apparatus. Spray drying was conducted under the following conditions: inlet air temperature=200° C.; outlet air temperature=70° C., atomizing air pressure for the nozzle=2.0 bar; air flow=80.0 kg/hour; spray rate=65 g/minute. During development of these methods, an initial outlet air temperature of 60° C. was used; however, this temperature was found to be too low, and the spray rate was adjusted back to a level to achieve an outlet temperature of about 70° C. which was found to be optimal. Following spray-drying, powdered serum was collected at the cyclone of the apparatus, and process air was filtered through an exhaust filter prior to recirculation within the apparatus.

Figure 3A:
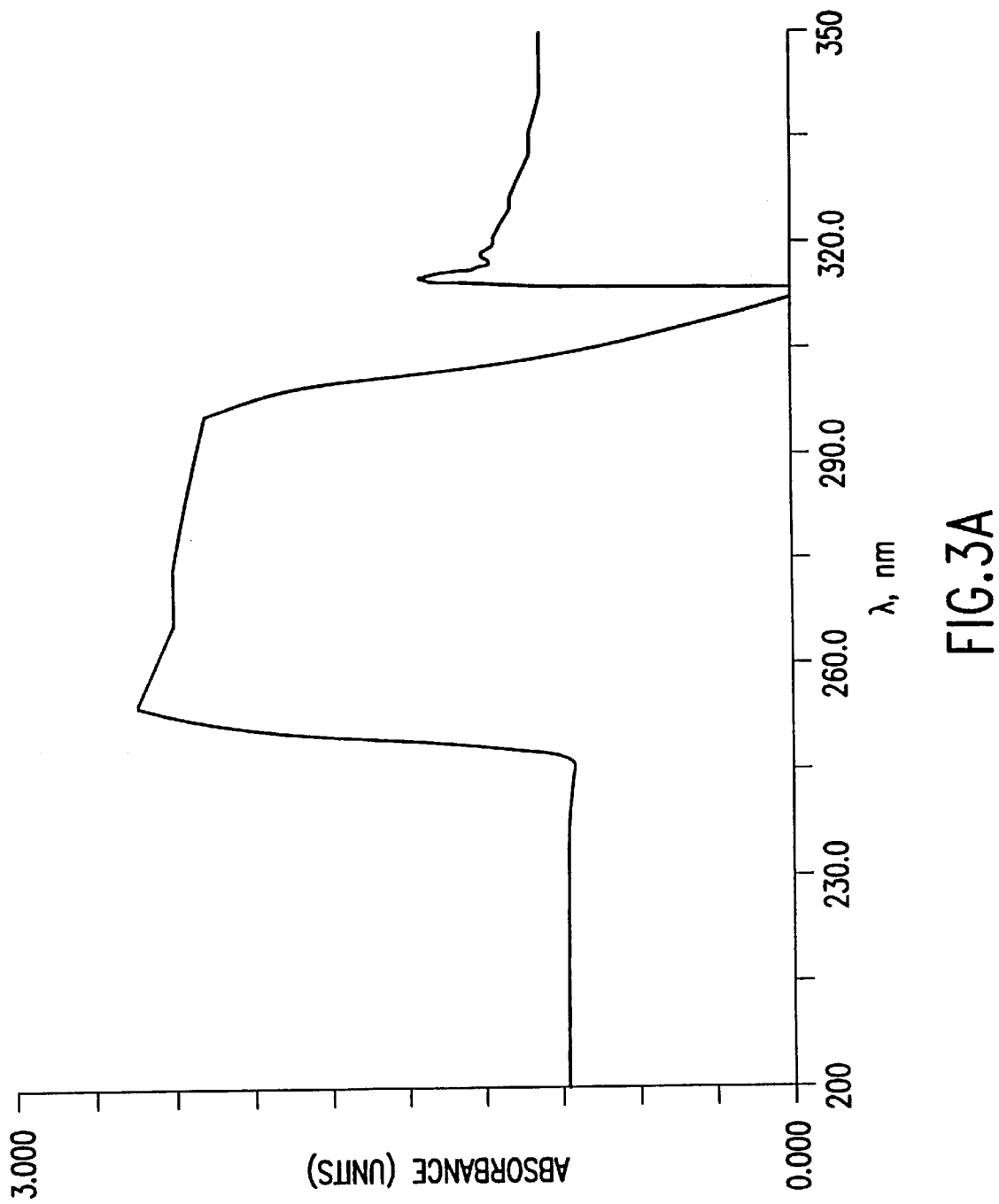
FIG. 3 is composite of histograms of spectrophotometric scans ($\lambda$=200–350 nm) of powdered fetal bovine serum (FBS) prepared by spray-drying according to the methods of the invention (FIG. 3A) or of standard liquid FBS FIG. 3B).

Following production, the powdered serum was characterized with respect to its physical properties, compared to liquid FBS from the same source lot. Samples taken from different stages of the production lot (samples "A" and "B") were reconstituted at a concentration of 60.44 g/L in endotoxin-free distilled water (Life Technologies, Inc.), and were examined for endotoxin levels using a Limulus Amoebocyte Lysate test (Life Technologies, Inc.), for hemoglobin levels (by spectrophotometrically measuring absorbance at 525 nm), and by UV/Vis spectrophotometry. Results are shown in Table 1, and in FIGS. 3A and 3B.

TABLE 1

Physical Characterization of Powdered Serum.

| Material Tested | Endotoxin Level (EU/ml) | Hemoglobin (mg/100 ml) |
|---|---|---|
| Powdered FBS, Sample "A" | 0.6 | 7.7 |
| Powdered FBS, Sample "B" | <0.3 | 7.7 |
| Liquid FBS (control) | <0.3 | 7.2 |

Figure 3B:
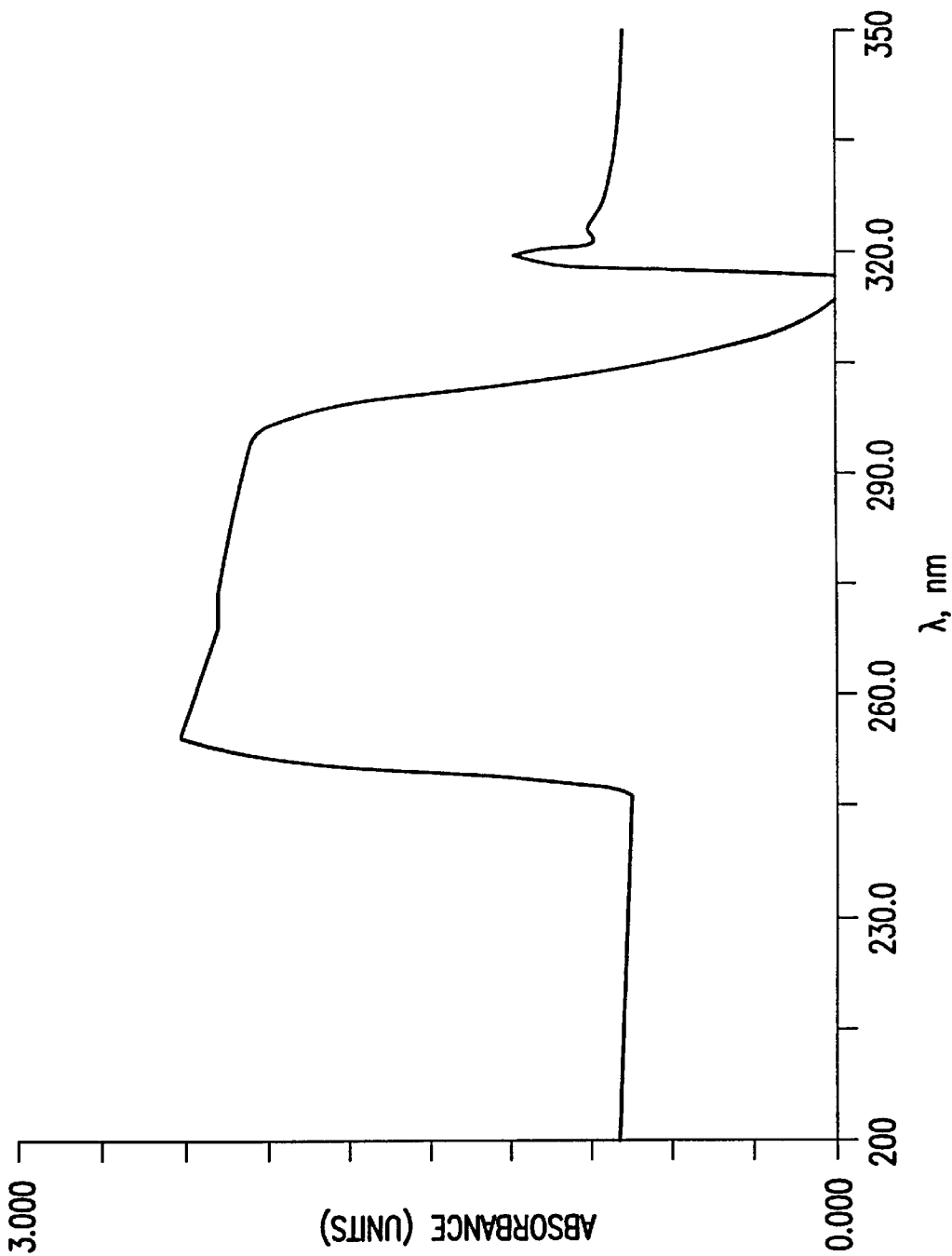

As seen in Table 1, powdered FBS demonstrated endotoxin and hemoglobin levels similar to those of the liquid FBS that served as the source material for production of the powdered FBS. Moreover, samples taken from different stages of the production process demonstrated nearly identical endotoxin and hemoglobin levels, indicating that the present methods result in the production of material with approximately uniform physical consistency across the production lot. When samples of powdered and liquid FBS were examined by UV/visible spectrophotometry (FIG. 3), the trace observed for powdered FBS (FIG. 3A) was indistinguishable from that obtained for the source liquid FBS (FIG. 3B). Together, these results indicate that serum powder prepared by the present spray-drying methods have nearly identical physical characteristics as those of liquid sera from which the powders are prepared. Taken together with those of Example 7 above (see, e.g., FIG. 1), these results demonstrate that the methods provided by the present invention result in the production of powdered sera with physical characteristics that are unaltered from those of the source liquid sera.

Example 9

Production of Automatically pH-Adjusted Powdered Culture Media

One reason that sodium bicarbonate is never included in powdered media is that any moisture, even that in the air, may result in an acidic condition within the pouch that will result in the liberation of $CO_2$ gas. The pouches will become swollen and produce what have been called "pillows." With fluid bed processing, the humidity within the apparatus is reduced essentially to negligible levels prior to the end of the process. We have made RPMI-1640 powdered media containing sodium bicarbonate and have not seen evidence of "pillow" formation.

Figure 4A:
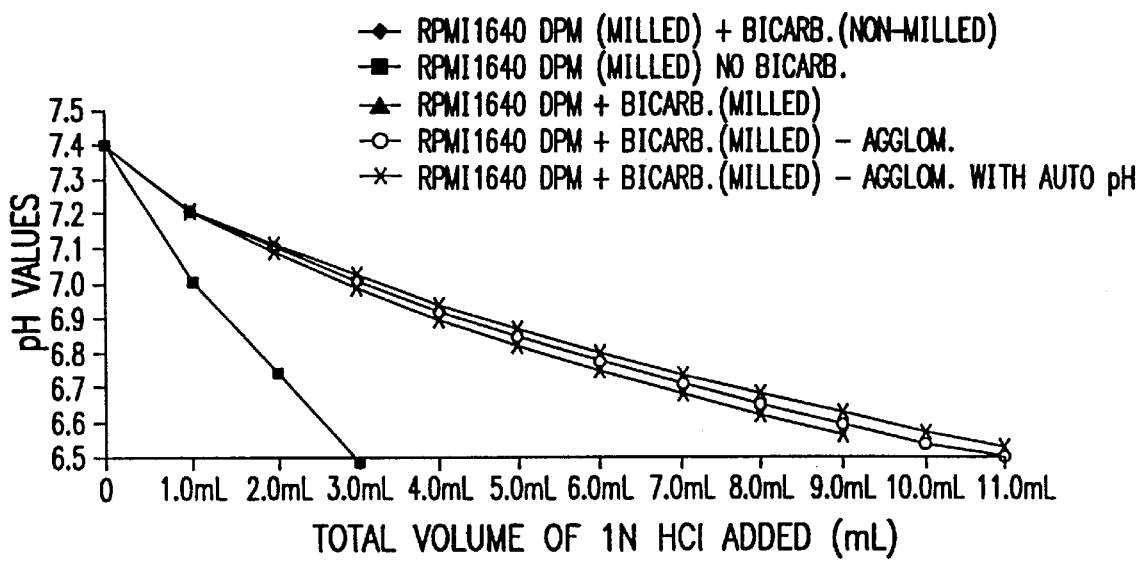
FIG. 4 is a composite of line graphs showing the pH titration (buffer capacity), on two different dates FIGS. 4A and 4B), of various dry powdered media (DPM) prepared by the methods of the invention or by ball-milling, with or without the addition of sodium bicarbonate.
Figure 4B:
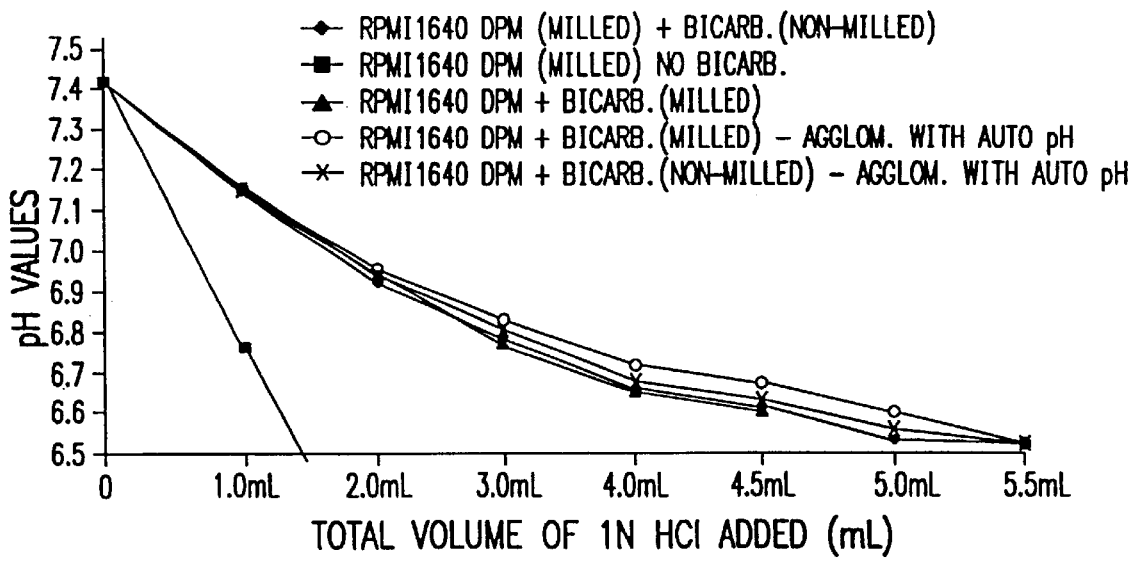

In order to make a pH-adjusted powdered media, it is necessary to add the pH-adjusting chemical (usually HCl or NaOH) to the powder to bring the pH to about 7.0–7.4 upon addition to water. Once sodium bicarbonate is added to the powder, many powdered media reconstitute in water on the basic side of neutrality and need HCl addition. Adding HCl to a powder containing sodium bicarbonate would be expected to be problematic. However, since the added liquid (5N HCl in this case) never results in a moistened or "liquid" state inside the fluid bed apparatus, the sodium bicarbonate does not give off $CO_2$ gas and fully retains its buffering capacity. This has been examined in the present studies by pH-titering experiments: equal amounts of acid, in two separate experiments (FIGS. 4A and 4B) were found to reduce the pH of agglomerated media and automatic pH-adjusted agglomerated media by an identical amount as that for a standard medium with sodium bicarbonate added to the liquid at the time of reconstitution. These results indicate that both agglomeration with subsequent adjustment of pH, and agglomeration with adjustment of pH during the agglomeration process, function equally well to produce powdered culture media with significant buffering capacity.

Example 10

Effect of Agglomeration on Dissolution Rates of Culture Media

Figure 5A:
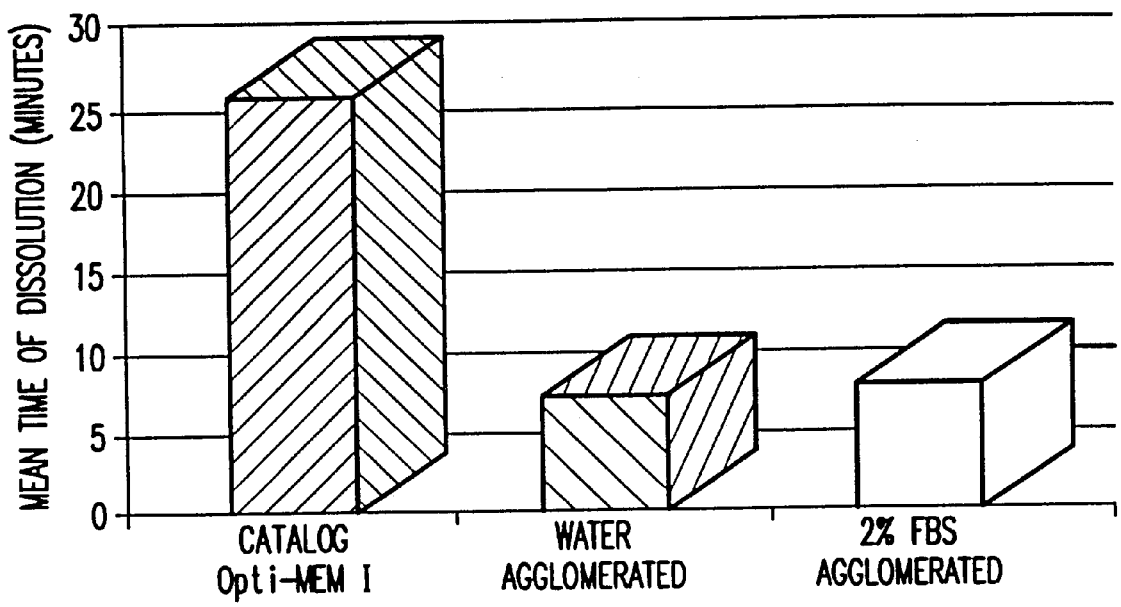
FIG. 5 is a composite of bar graphs showing the effect of agglomeration on dissolution rates (in water) of Opti-MEM I™ (FIG. 5A) or DMEM (FIG. 5B). Media were agglomerated with water or FBS as indicated.
Figure 5B:
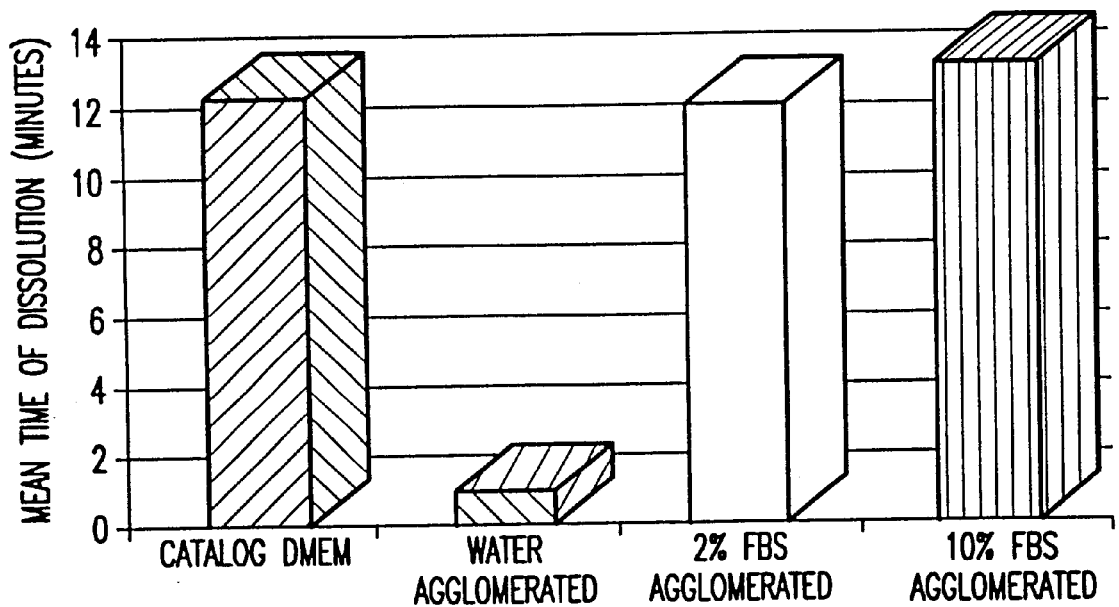

To examine the effect of agglomeration of culture media on the rate of dissolution of the media, samples of Opti-MEM I™ or DMEM were agglomerated with water or with FBS (2% only for Opti-MEM I; 2% or 10% for DMEM). Upon reconstitution of the agglomerated media in water, the time dissolution of the agglomerated Opti-MEM I occurred much more quickly than did dissolution of standard powdered Opti-MEM I (FIG. 5A); results were identical for water- and FBS-agglomerated Opti-MEM I. Interestingly, however, while water-agglomerated DMEM dissolved in water much more quickly than did standard powdered DNEM, the FBS-agglomerated DMEM did not (FIG. 5B).

Due to the open structure of the agglomerated powdered media (as opposed to traditional powdered media), capillary action brings water into close proximity with all of the powder particles. This prevents the appearance of powder "balls," a complication observed upon reconstitution of most standard powdered media that leads to longer dissolution times. In addition to more rapid dissolution, agglomerated media demonstrated reduced dusting as well. These results indicate that water-agglomerated culture media, and some FBS-agglomerated culture media, are much more rapidly dissolving and generate less dust than traditional powdered culture media.

Example 11

Cell Growth and Subculturing in Reconstituted Agglomerated Culture Media

Many uses of culture media require additions of large molecular weight proteins such as serum or albumin. These molecules may be in the form of solutions or even powder in the case of albumin. However, in order to insure uniformity of powdered media, these proteins are usually added not as a powder but as liquid after reconstitution of the bulk powdered media to a liquid medium. This presents some inconvenience since, for example, serum must be stored in the freezer to maintain performance over time. This adds expense and inconvenience since the serum must be added aseptically to the media, increasing chances of contamination. If filtration is done after addition of serum, another processing step is needed. There would therefore be advantages to being able to provide serum as an integral part of the powdered media.

Therefore, culture media were agglomerated with water or with various concentrations of FBS. FBS was added to the powdered media by injecting it into the air-suspended dry powdered media at high evaporation rates, as generally outlined above. The level of serum supplementation was 2% in Opti-MEM I media, and 2% or 10% in DMEM. The growth and passage success of various cell lines in these media were then assessed.

Figure 6A:
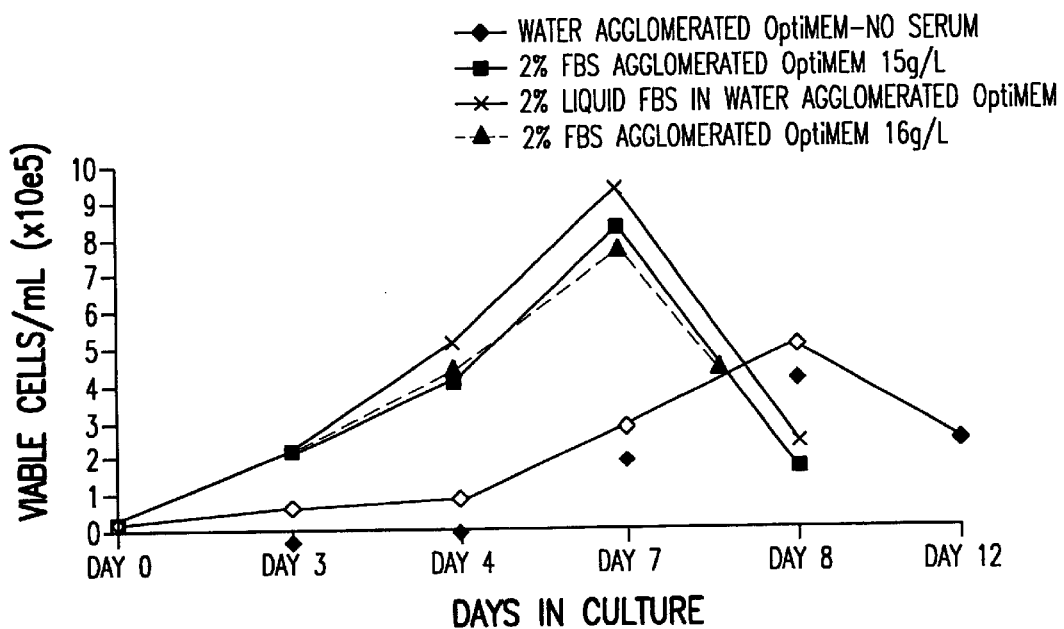
FIG. 6 is a composite of line graphs showing growth over seven days of SP2/0 cells in agglomerated Opti-MEM I™ (FIG. 6A) or DMEM (FIG. 6B), both containing 2% FBS.
Figure 6B:
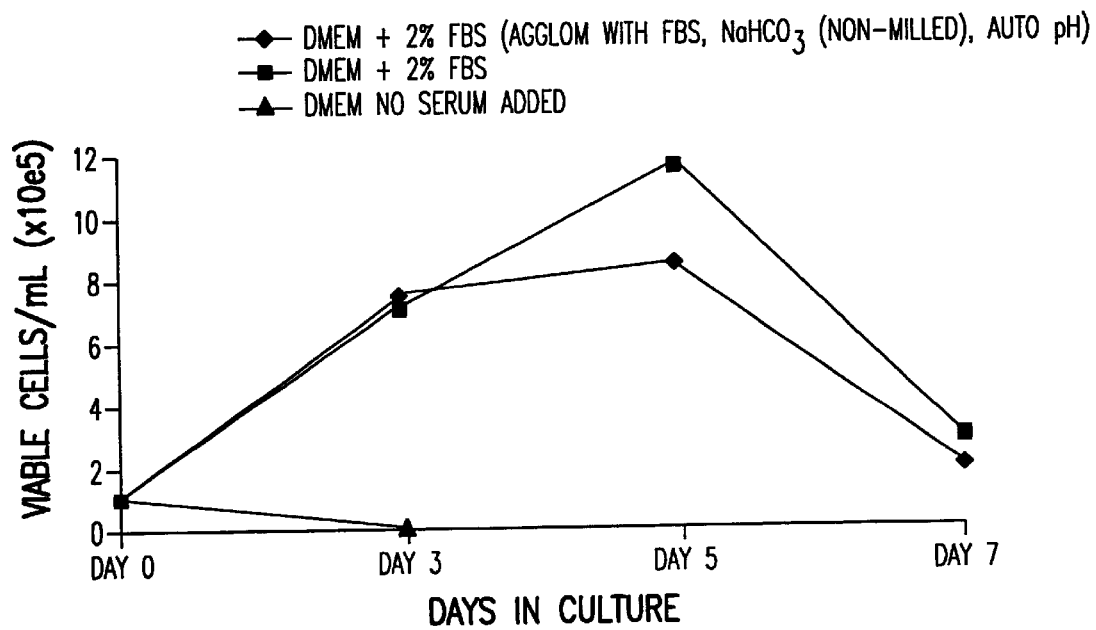
Figure 7A:
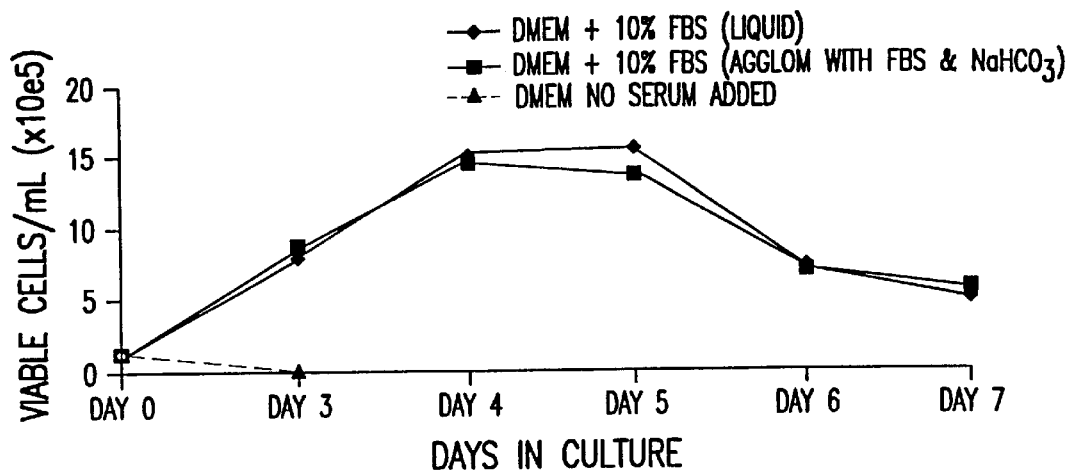
FIG. 7 is a composite of line graphs showing growth over seven days of SP2/0 cells (FIG. 7A), AE-1 cells (FIG. 7B) and L5.1 cells (FIG. 7C) in agglomerated DMEM containing 10% FBS.
Figure 7B:
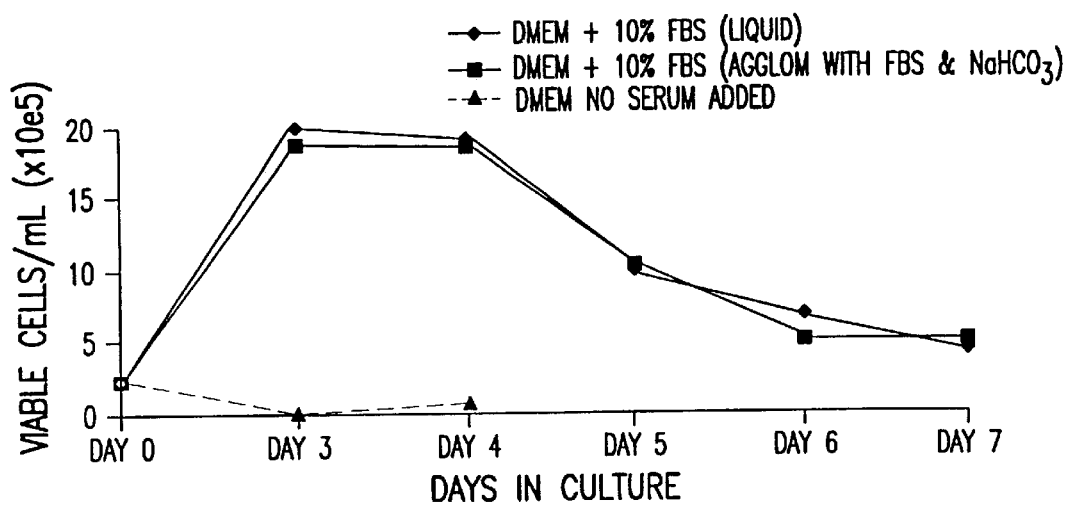
Figure 7C:
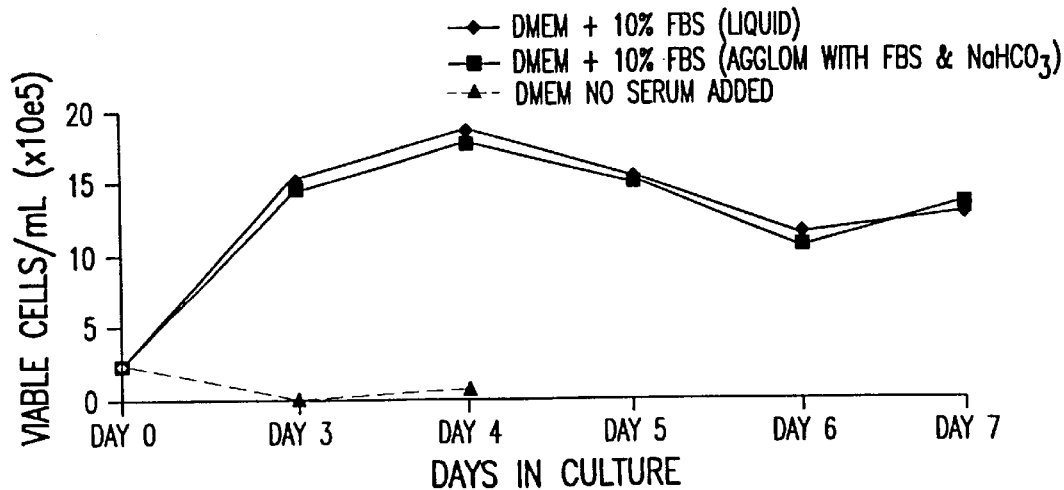
Figure 8A:
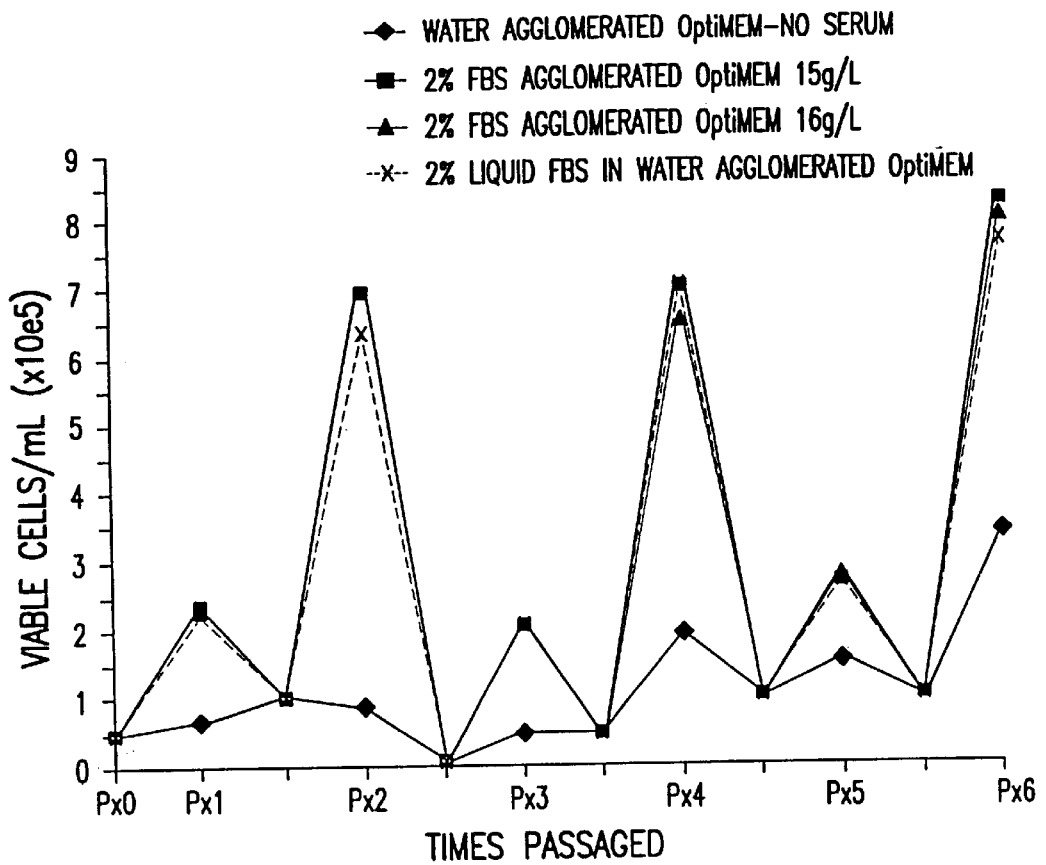
FIG. 8 is a composite of line graphs showing passage success of SP2/0 cells in Opti-MEM I™ (FIG. 8A) or DMEM (FIG. 8B), agglomerated with either water or FBS, supplemented with 2% FBS.
Figure 8B:
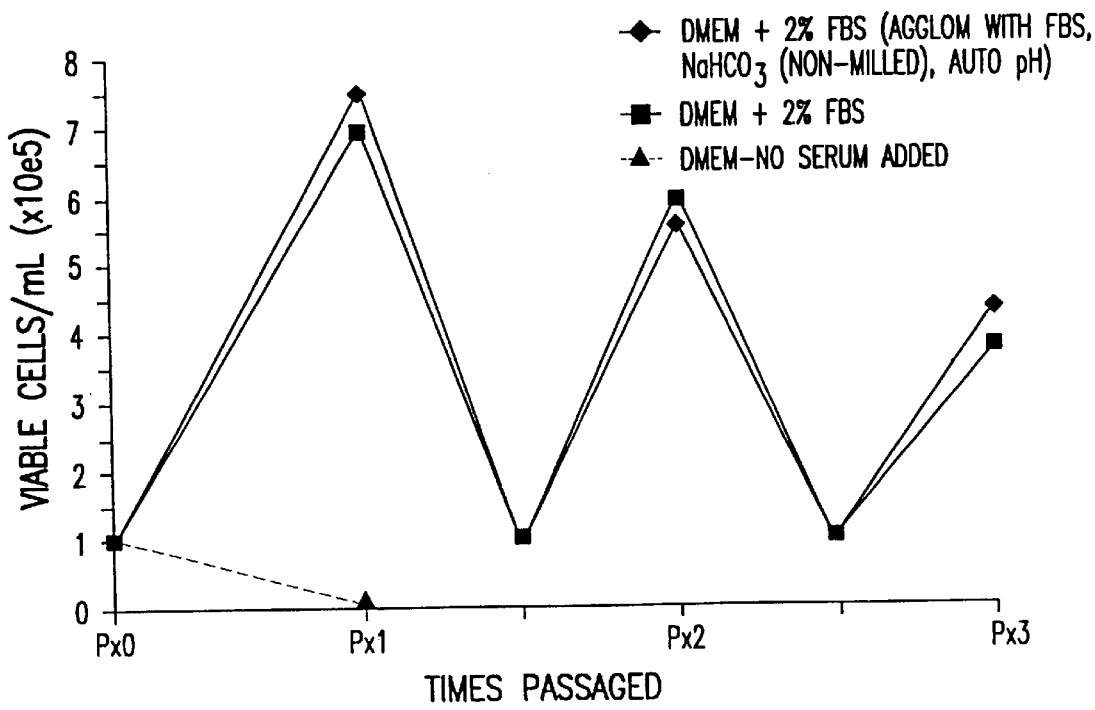
Figure 9A:
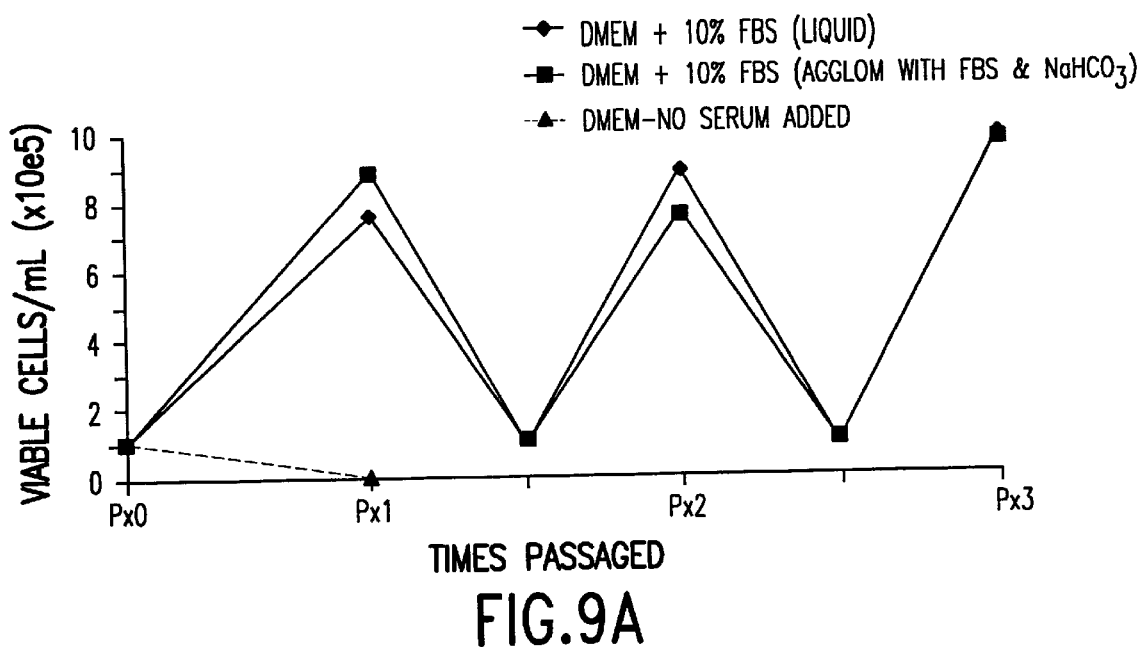
FIG. 9 is a composite of line graphs showing passage success of SP2/0 cells (FIG. 9A), AE-1 cells (FIG. 9B) and L5.1 cells (FIG. 9C) in DMEM agglomerated with FBS and sodium bicarbonate and supplemented with 10% FBS.
Figure 9B:
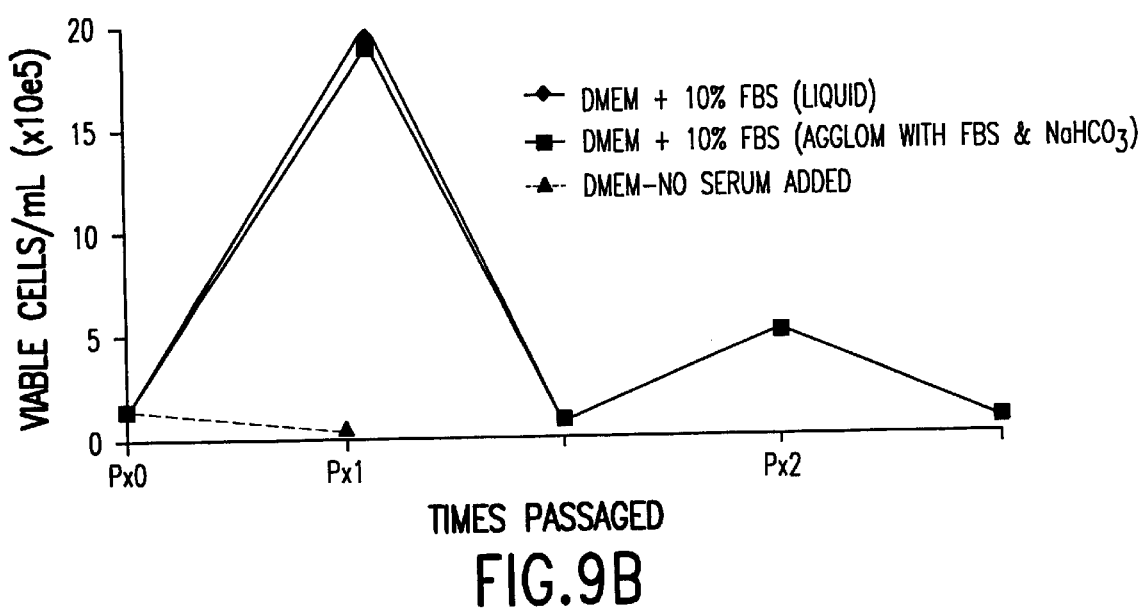
Figure 9C:
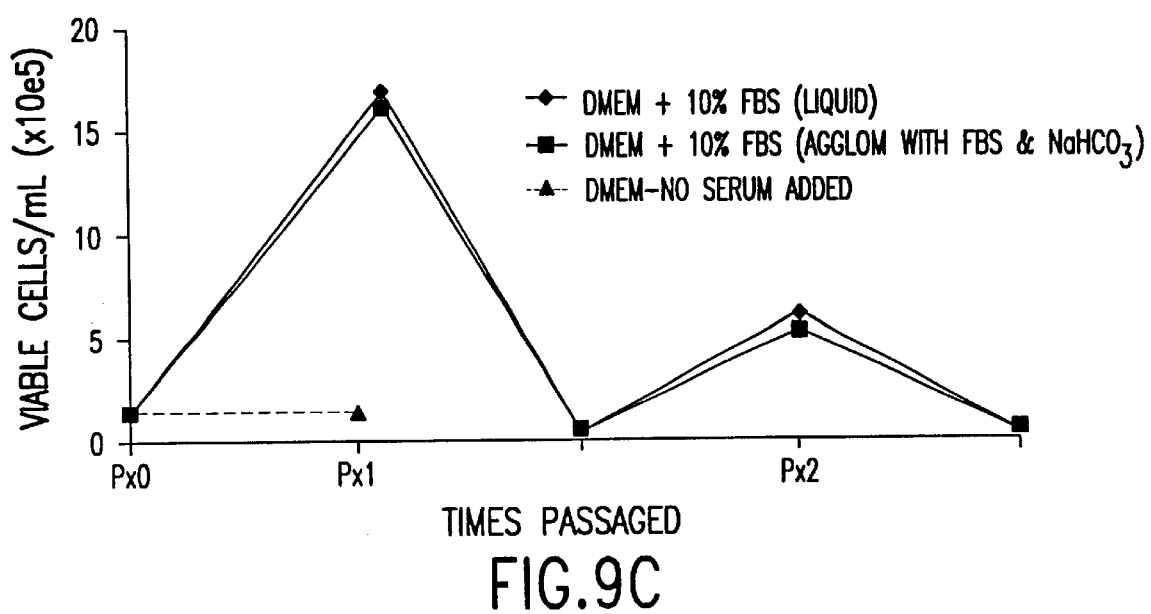
Figure 10:
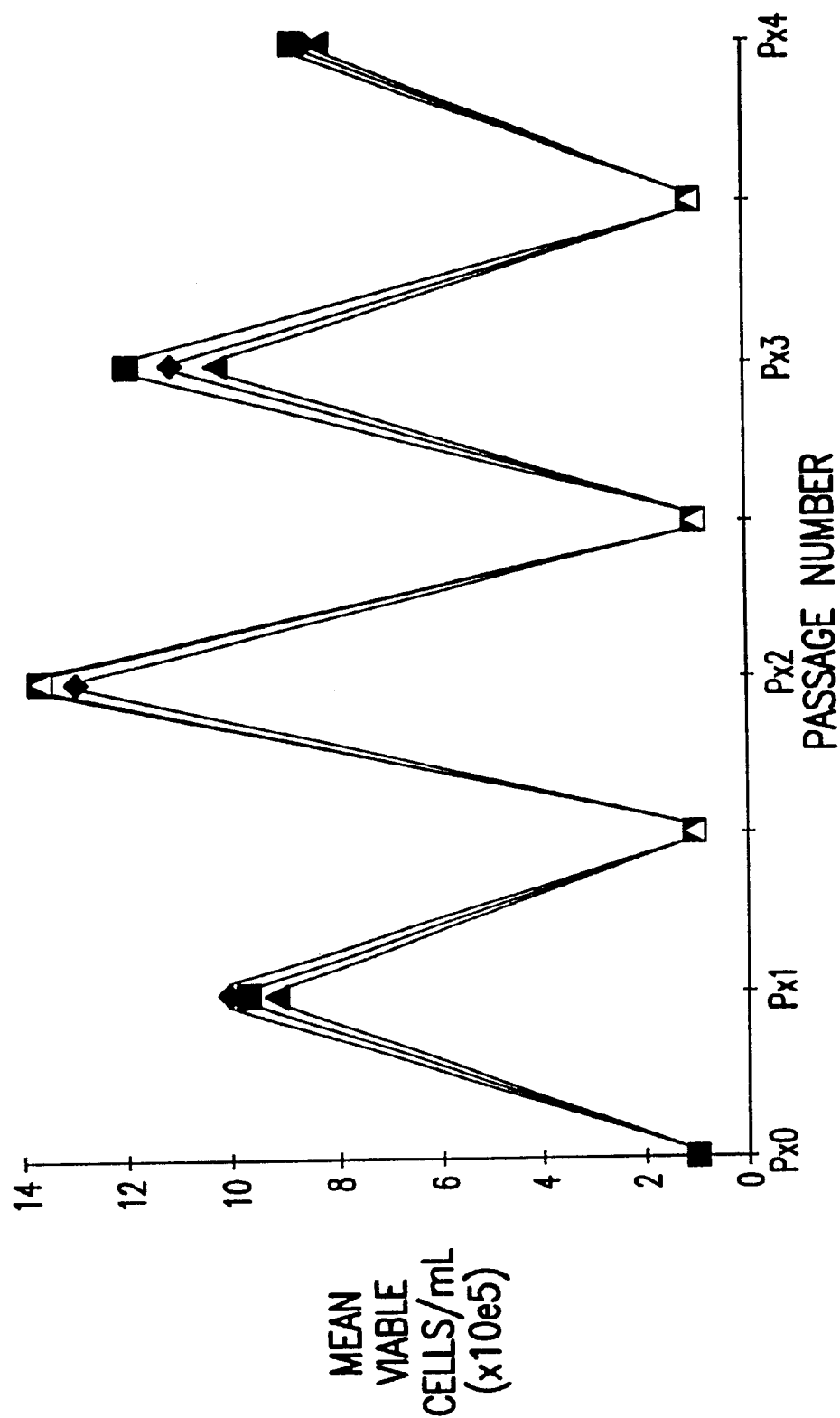
FIG. 10 is a line graph showing the growth of SP2/0 cells over four passages in standard water-reconstituted powdered culture media (control media), or in agglomerated powdered culture media prepared in large-scale amounts according to the methods of the invention. Results are shown for control media (□), water-agglomerated powdered culture media of the invention (♦) and water-agglomerated auto-pH powdered culture media (containing sodium bicarbonate) of the invention (■).

As shown in FIG. 6, SP2/0 cells demonstrated similar growth rates when grown in Opti-MEM I agglomerated with either water or with FBS (FIG. 6A), compared to cells grown under conventional culture conditions (liquid serum added to water-reconstituted powdered media). Similar results were observed with SP2/0 cells cultured in water- and FBS-agglomerated DMEM supplemented with 2% FBS (FIG. 6B), and with SP2/0 cells (FIG. 7A), AE-1 cells (FIG. 7B) and L5.1 cells (FIG. 7C) cultured in water- and FBS-agglomerated DMEM supplemented with 10% FBS. In addition, SP2/0 cells showed approximately similar recovery rates from passage when cultured in water- or agglomerated Opti-MEM I and DMEM supplemented with 2% FBS (FIGS. 8A and 8B, respectively), as did SP2/0 cells, AE-1 cells and L5.1 cells cultured in water- and FBS-agglomerated DMEM supplemented with 10% FBS (FIGS. 9A, 9B and 9C, respectively) and SP2/0 cells cultured in water-agglomerated DMEM supplemented with 5% FBS (FIG. 10). Furthermore, SP2/0 cells demonstrated identical passage characteristics in water-agglomerated media produced in large batches and in automatically pH-adjusting powdered DMEM containing sodium bicarbonate as they did in standard liquid DMEM supplemented with 5% FBS (FIG. 10).

Together, these results indicate that culture media supplements such as animal sera (e.g., FBS) may be agglomerated directly into culture media, and that supplementation of culture media during the agglomeration process in this way produces a culture medium that provides optimal support of growth and passage of a variety of cultured cells. Furthermore, these results indicate that the present culture media powders may be successfully produced in large batches, including the automatically pH-adjusting media of the invention that contain sodium bicarbonate.

Example 12

Cell Growth in Culture Media Supplemented with Spray-Dried Serum Powder

Figure 12A:
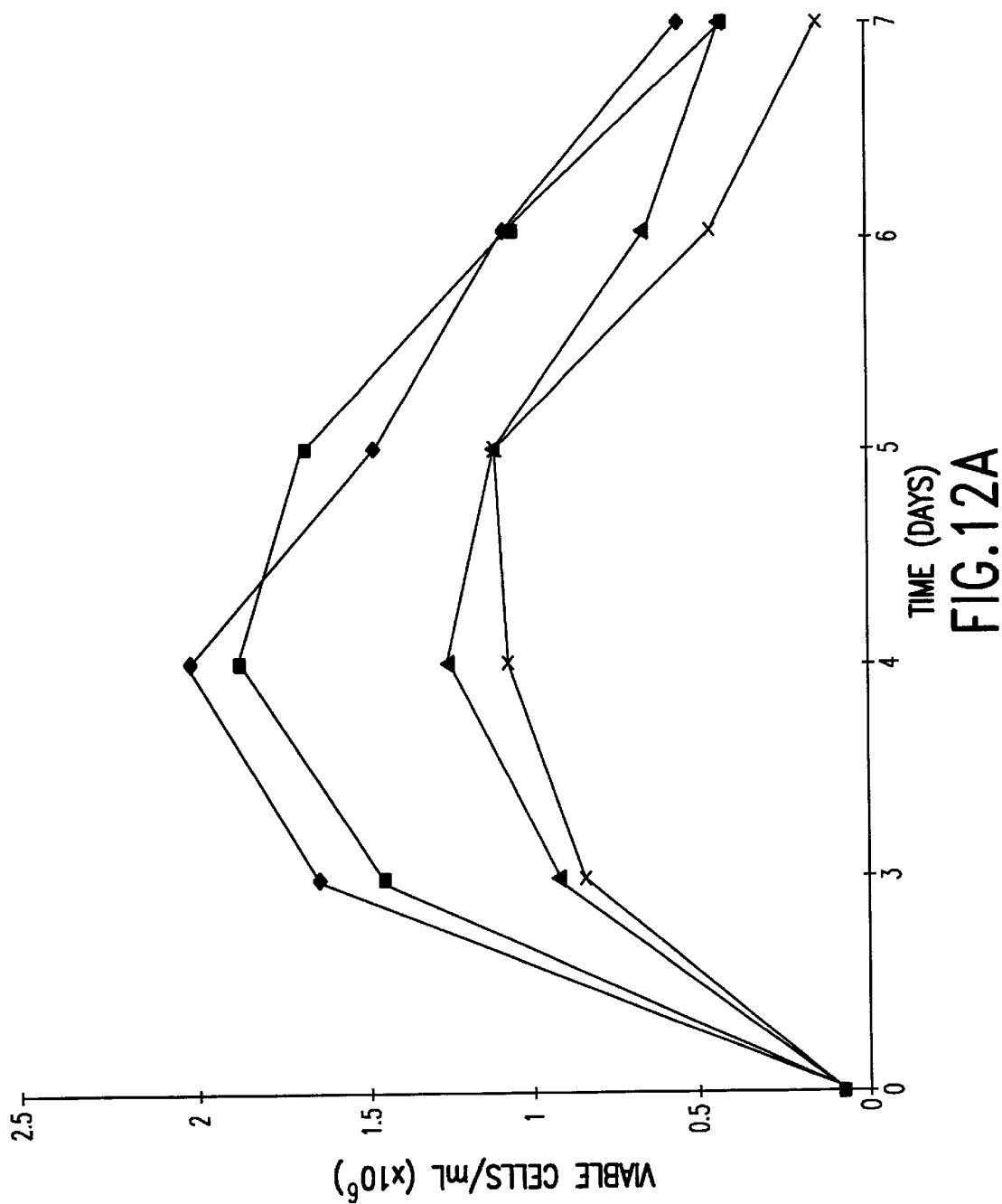
FIG. 12 is a line graph of SP2/0 cells cultured over seven days in medium containing 2% (▲) or 10% (♦) liquid FBS, or 2% (✻) or 10% (■) powdered FBS prepared by the spray-drying methods of the invention. Duplicate experiments are shown in FIGS. 12A and 12B.
Figure 12B:
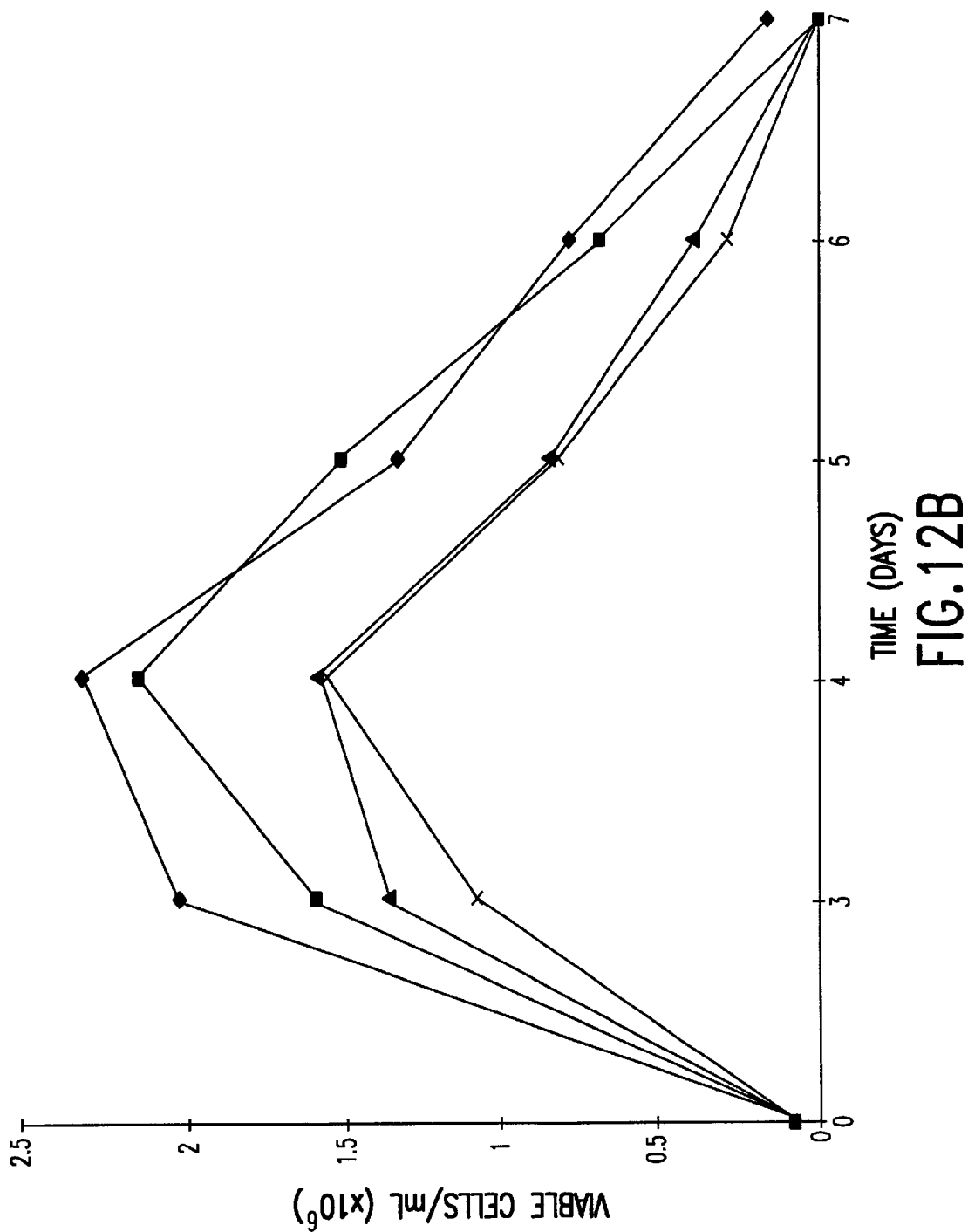
Figure 13:
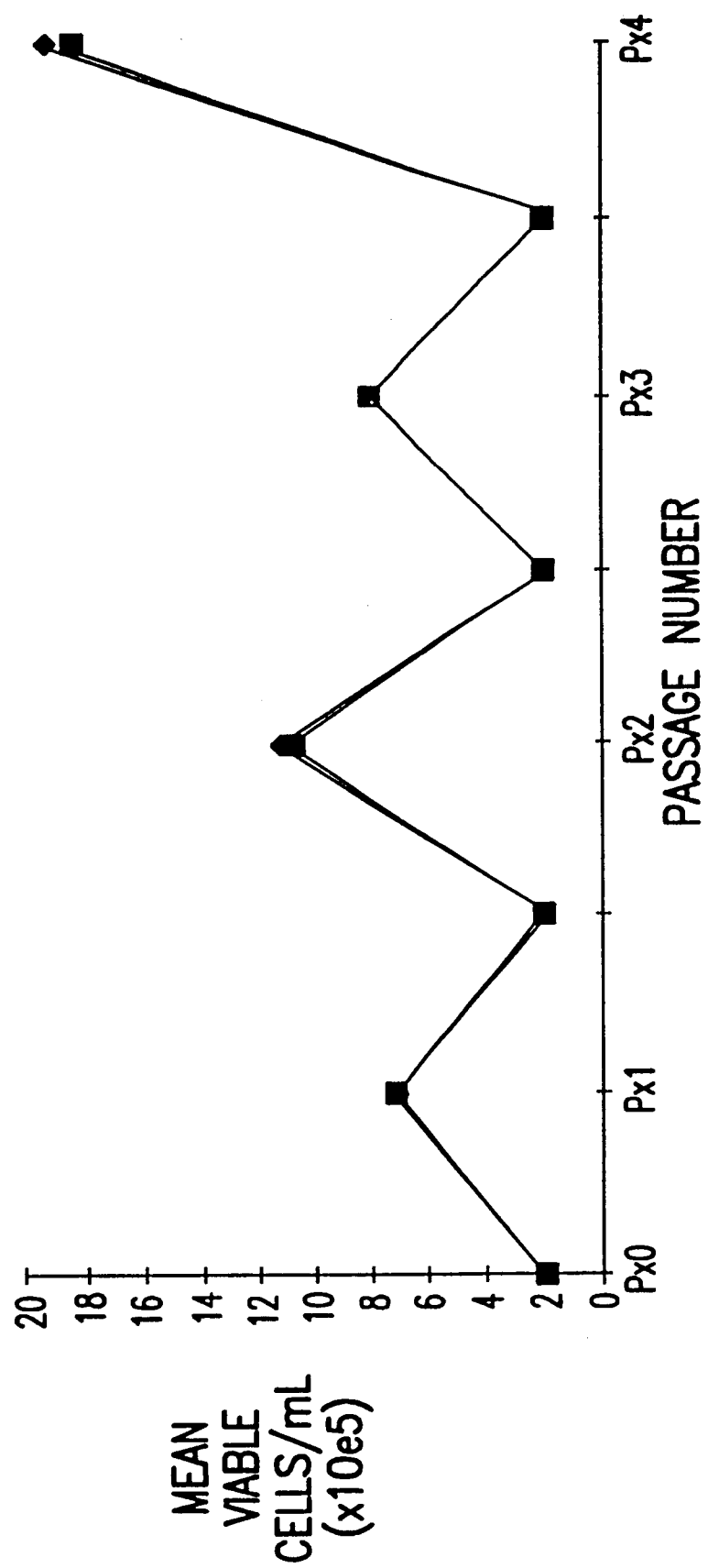
FIG. 13 is a line graph of AE-1 cell growth over four passages in media containing 5% liquid FBS (♦) or 5% powdered FBS prepared by the spray-drying methods of the invention (■).

As a corollary to the experiments shown in Example 7, AE-1 cells and SP2/0 cells were plated into DMEM containing either 2% or 10% spray-dried FBS prepared as described in Example 8, or containing 2% or 10% liquid FBS, and growth rates and passage recovery of the cells were examined. Cells were inoculated into triplicate 25 cm² flasks at a density of $1 \times 10^5$ cells/ml in 10 ml of media. Viable cell density was determined on days 3–7, and each cell line was tested twice. Results are shown in FIGS. 11–13.

Figure 11A:
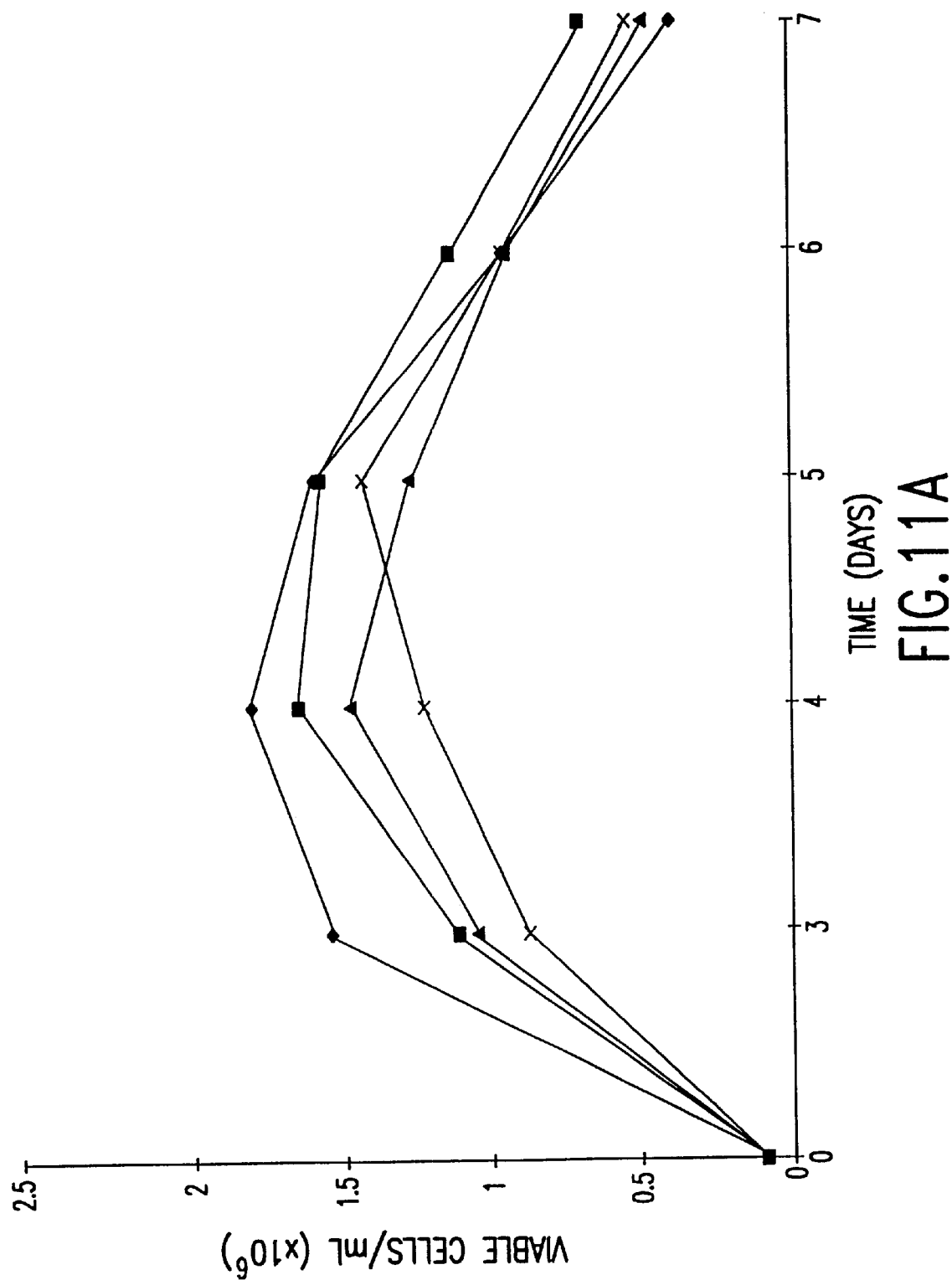
FIG. 11 is a line graph of AE-1 cells cultured over six or seven days in medium containing 2% (▲) or 10% (♦) liquid fetal bovine serum (FBS), or 2% (✻) or 10% (■) powdered FBS prepared by the spray-drying methods of the invention. Duplicate experiments are shown in FIGS. 11A and 11B.
Figure 11B:
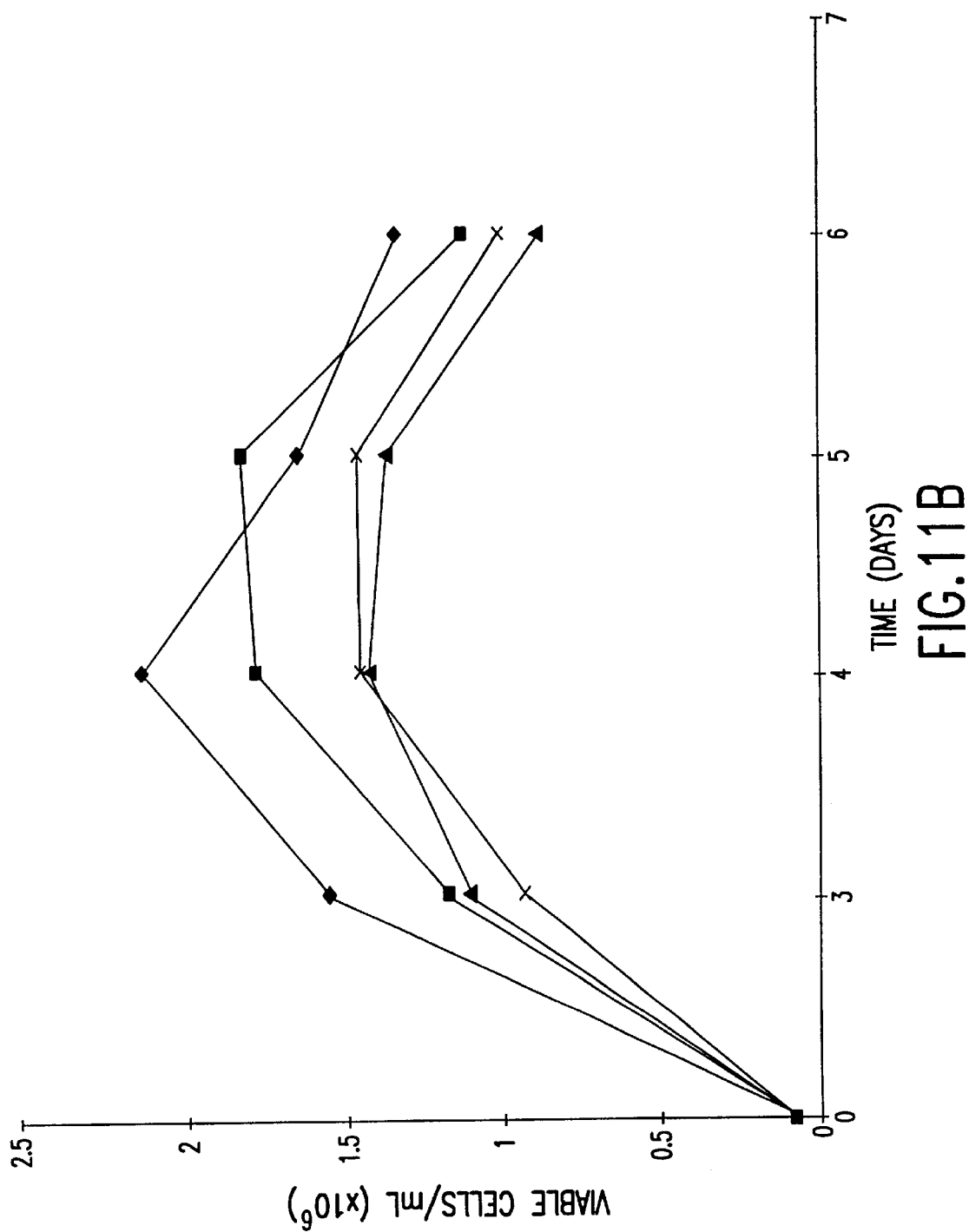

As shown in FIG. 11, AE-1 cells cultured in media containing powdered FBS demonstrated similar growth kinetics to those cells cultured in media containing standard liquid FBS. As expected, the cells demonstrated more rapid growth to a higher density in culture media containing 10% FBS than in media containing 2% FBS, and demonstrated peak growth by about day four. Similar kinetics were observed for two separate experiments (FIGS. 11A and 11B), indicating that these results were reproducible. Analogous results were obtained in two experiments in which the growth rates of SP2/0 cells were measured in media containing powdered or liquid FBS (FIGS. 12A and 12B). In addition, AE-1 cells cultured in media containing 5% powdered FBS recovered from passage with identical growth rates as cells in media containing liquid FBS (FIG. 13).

These results indicate that the powdered FBS prepared by the spray-drying methods of the present invention performs approximately equivalently to liquid FBS in supporting growth and passage of cultured cells. Together with those from Examples 7 and 8, these results indicate that the methods of the present invention may be used to produce powdered FBS, by fluid bed or spray-drying technologies, that demonstrates nearly identical physical and performance characteristics as those of liquid FBS.

Example 13

Effect of Irradiation on Performance of Agglomerated Media

Recently, concerns have been raised about the biological purity of media and media components (including supplements) used for bioproduction, particularly in the biotechnology industry. Gamma irradiation is a sterilization process that is known to work well with certain liquids and powders that are not typically amenable to sterilization by heat or toxic gas exposure. Therefore, samples of water- or FBS-agglomerated culture media were γ irradiated with a cobalt source at 25 kGy for up to several days, and the growth rates of various cell types examined.

In one set of experiments, SP2/0 cells were inoculated into various media at $1 \times 10^5$ cells/ml and cultured at 37° C. At various intervals, samples were obtained aseptically and cell counts determined by Coulter counting and viability determined by trypan blue exclusion. Media were prepared by dissolving sufficient powdered media to make a 1×solution in 1L of water, stirring and filtering through a 0.22 μm filter. Results are shown in the graph in FIG. 14. Those conditions on the graph that state "pwdr FBS" on the graph refer to the addition of powdered FBS (prepared as in Examples 7 or 8 above) to the reconstituted 1×medium prepared from either standard powdered media or from agglomerated media (irradiated or non-irradiated). Those conditions on the graph that state "Irradia. agglom. DMEM+ FBS" refer to use of the fluid bed to make the agglomerated media by spraying FBS into the powdered media (standard or agglomerated) to make an FBS-agglomerated media.

Figure 14:
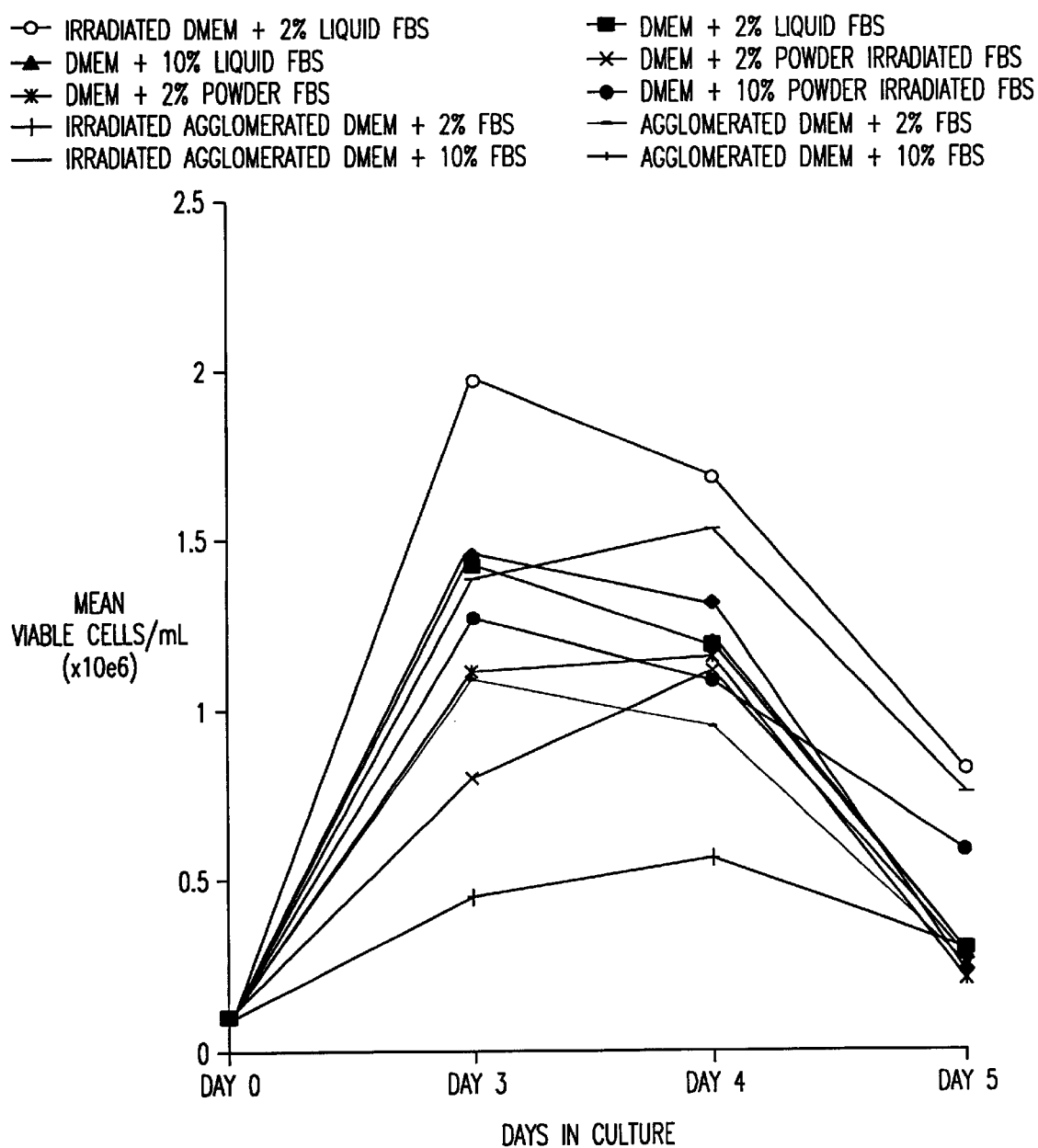
FIG. 14 is a line graph indicating the effect of γ irradiation and agglomeration on the growth of SP2/0 cells over five days.

As shown in FIG. 14, γ irradiation of standard powdered basal media and agglomerated basal media did not deleteriously affect the ability of these media to support SP2/0 cell growth. In addition, while irradiation did negatively impact powdered media containing powdered FBS, and powdered FBS itself, this effect diminished with increasing serum concentration.

To more broadly examine these γ irradiation effects, samples of VERO cells were inoculated into VP-SFM™ that had been conventionally reconstituted or agglomerated as above. To the powdered media in the agglomeration chamber, however, epidermal growth factor (EGF) and ferric citrate chelate, traditional supplements for this media, were added via the spray nozzle during agglomeration. Media were then used directly or were γ irradiated as described above. Cells were inoculated at 3×10⁵ cells/flask into T-25 flasks and incubated at 37° C. Cell counts and viability were performed as described above, with results shown in FIG. 15.

Figure 15:
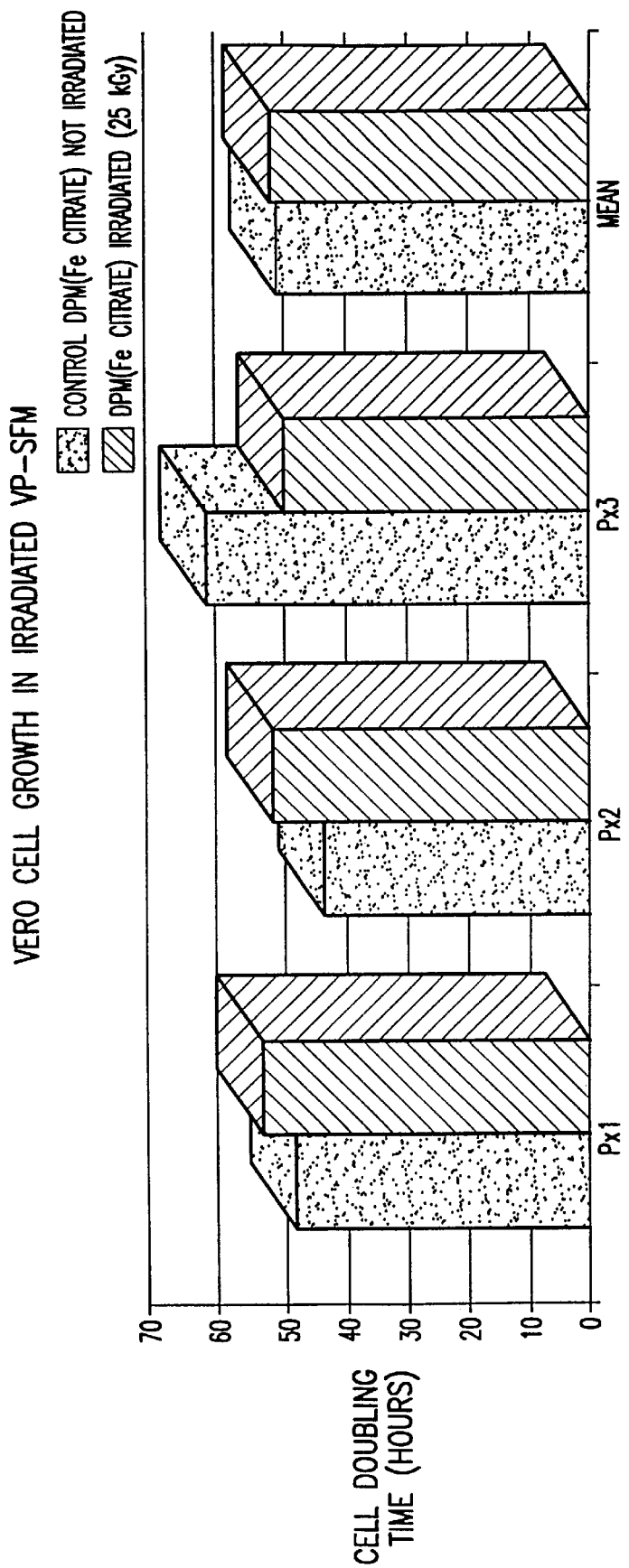
FIG. 15 is a bar graph indicating the effect of γ irradiation on the growth of VERO cells in agglomerated culture media.

As seen in FIG. 15, VERO cells demonstrated approximately equivalent growth and passage success when cultured in agglomerated media that had been γ-irradiated as in agglomerated media that had not been γ-irradiated. Furthermore, irradiation of the media had no effect on the low-level culture supplements EGF and ferric citrate chelate that were present in the media.

These results indicate that γ irradiation may be used as a sterilization technique in the preparation of many bulk agglomerated culture media, including those containing serum, EGF or other supplements, by the present methods.

Example 14

Effect of Irradiation on Performance of Powdered Media Supplements

To demonstrate the efficacy of the present methods in producing sterile media supplements, lyophilized human holo-transferrin was irradiated by exposure to a cobalt γ source at 25 kGy for about 3 days at −70° C. or at room temperature. 293 cells were then cultured in media that were supplemented with irradiated transferrin or with control transferrin that had not been irradiated (stored at −70° C. or at room temperature), and cell growth compared to that of standard transferrin-containing culture media or media that contained no transferrin.

Mid-log phase 293 cells that were growing in serum-free 293 medium (293 SFM) were harvested, washed once at 200×g for 5 minutes and resuspended in transferrin-free 293 SFM for counting and viability determination. Cells were plated into triplicate 125 ml Ehrlenmeyer flasks at a density of 3×10⁵ cells/ml in a volume of 20 ml in 293 SFM (positive control), transferrin-free 293 SFM (negative control), in 293 SFM containing non-irradiated transferrin stored at −70° C. or at room temperature, or in 293 SFM containing irradiated transferrin prepared as described above. Flasks were placed into a rotary shaker set at about 125 rpm, in a 37° C. incubator equilibrated with an atmosphere of 8% $CO_2$/92% air. Daily cell counts were determined using a Coulter particle counter and viabilities were determined by trypan blue exclusion according to standard procedures. When the cells reached a density of about 1.2 to 1.7×10⁶ per flask, the contents of one of the flasks of each sample were harvested, centrifuged, resuspended into fresh medium and passaged into three new flasks. Cell counts and viabilities of the previous and next passages were then performed as described above. Four consecutive passages of cells incubated under the above conditions were tested.

Figure 16A:
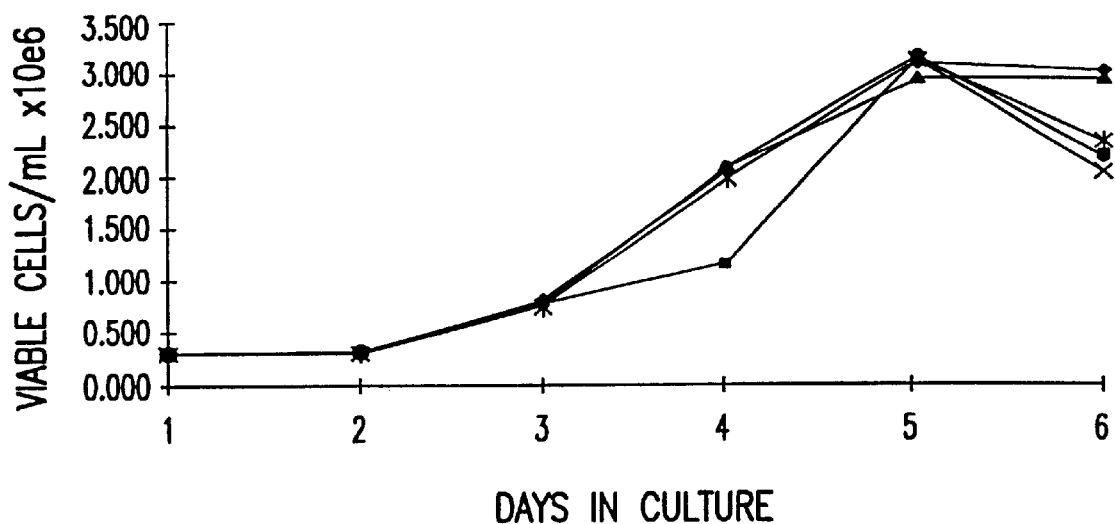
FIG. 16A: passage 1 cells.
Figure 16B:
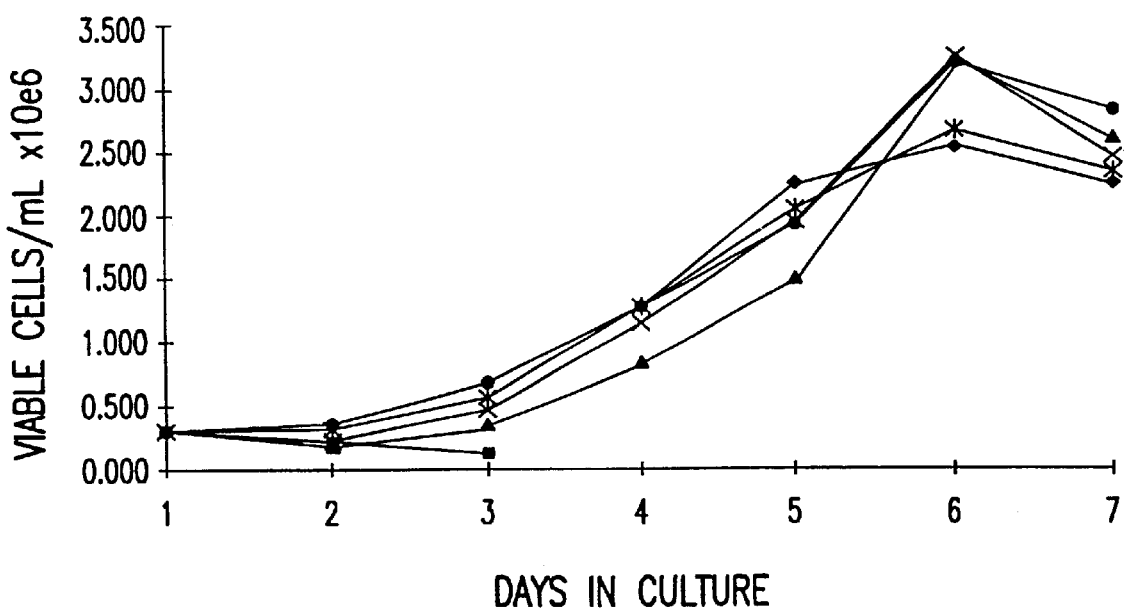
FIG. 16B: passage 2 cells.
Figure 16C:
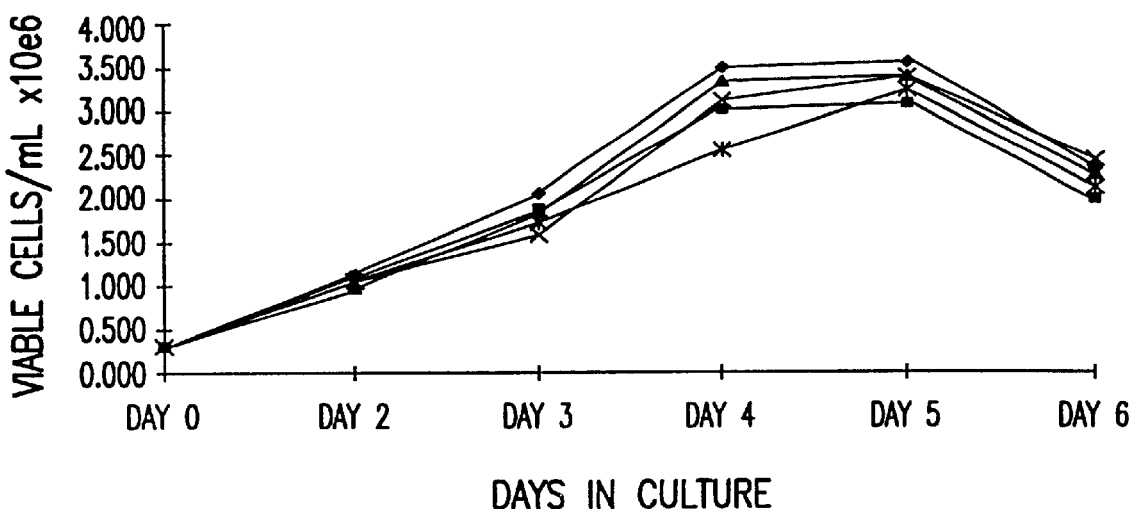
FIG. 16C: passage 3 cells.
Figure 16D:
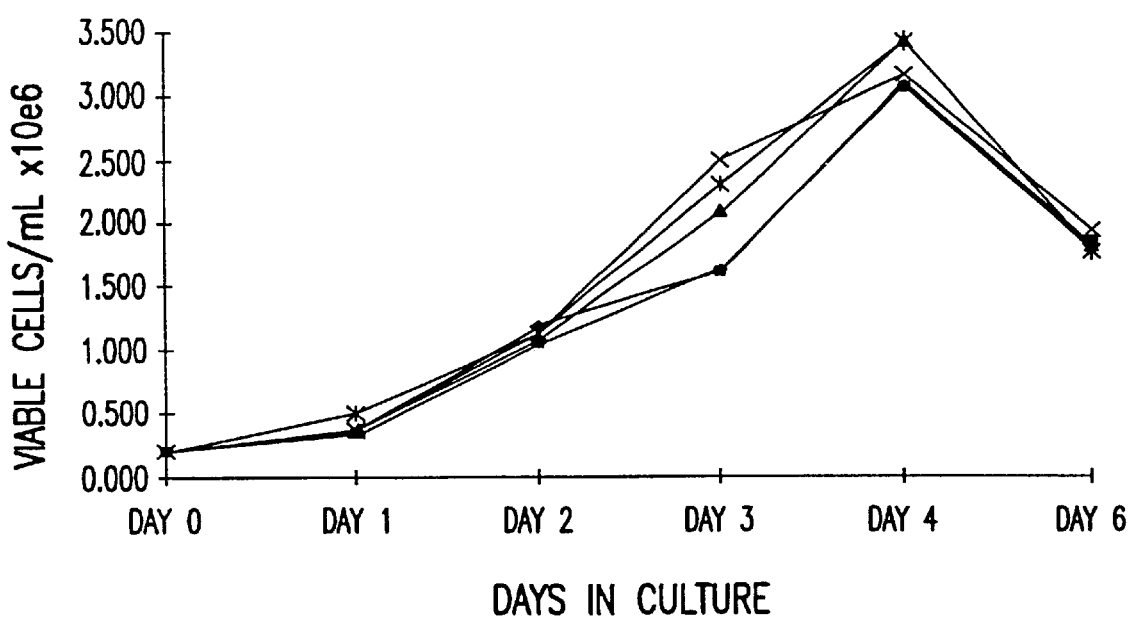
FIG. 16D: passage 4 cells.

As shown in FIGS. 16A–16D, cells cultured in media containing transferrin that was γ irradiated at either −70° C. or at room temperature demonstrated nearly identical growth kinetics and survival in the first passage (FIG. 16A), second passage (FIG. 16B), third passage (FIG. 16C) and fourth passage (FIG. 16D) as did cells cultured in standard 293 SFM or in 293 SFM containing transferrin that had not been γ irradiated. Cells cultured in transferrin-free media, however, survived well during the first passage (FIG. 16A) but stopped growing and demonstrated a significant loss in viability upon subculturing (FIG. 16B).

These results demonstrate that γ irradiation may be used as a sterilization technique in the preparation of bulk powdered culture media supplements, such as transferrin, in the methods of the present invention. Furthermore, these data indicate that culture media supplements such as transferrin may be γ irradiated at room temperature without significant loss of activity.

Example 15

Effect of Irradiation on Biochemical Characteristics of Powdered Sera

To further determine the impact of γ irradiation on sera, samples of spray-dried powder FBS were irradiated at 25 kGy at −70° C. or at room temperature (RT), and were analyzed commercially for the concentrations of various biochemical constitutents in the sera. As controls, samples of non-irradiated spray-dried FBS and liquid FBS were also analyzed. Results are shown in Table 2.

TABLE 2

Chemical Analysis of Spray-Dried FBS

| Constituent | Dried FBS, Irr. @ −70° C. | Dried FBS, Irr. @RT | Non-irradiated Dried FBS | Liquid FBS | Units | Reference Range |
|---|---|---|---|---|---|---|
| Sodium | 139 | 137 | 139 | 140 | mM | 136–144 |
| Potassium | 13.2 | 13.2 | 13.0 | 13.2 | mM | 3.6–5.2 |
| Chloride | 98 | 97 | 98 | 100 | mM | 98–108 |
| Uric Acid | 1.6 | 1.3 | 1.7 | 1.9 | mg/dL | 2.2–8.3 |
| Phosphorus | 10.1 | 10.1 | 9.6 | 10.2 | mg/dL | 2.2–4.6 |
| Calcium | 14.9 | 14.8 | 14.8 | 14.5 | mg/dL | 8.6–10.2 |
| Ionizable Calcium | >5.5 | >5.5 | >5.5 | >5.5 | mg/dL | 3.8–4.5 |
| Magnesium | 2.77 | 2.76 | 2.75 | 2.76 | meg/L | 1.4–2.0 |
| Alkaline Phosphatase | 57 | 47 | 68 | 269 | U/L | 31–142 |
| Gamma GT (GGTP) | 3 | 5 | <5 | 5 | U/L | 1–60 |
| AST (SGOT) | 7 | 5 | 5 | 33 | U/L | 1–47 |
| ALT (SGPT) | 5 | <5 | <5 | 7 | U/L | 1–54 |
| LD | 56 | <50 | 50 | 510 | U/L | 110–250 |
| Total Bilirubin | 0.19 | 0.24 | 0.22 | 0.13 | mg/dL | 0.2–1.4 |
| Direct Bilirubin | 0.04 | 0.07 | 0.07 | 0.04 | mg/dL | 0.0–0.3 |
| Glucose | 67 | 38 | 39 | 88 | mg/dL | 65–125 |
| BUN | 15 | 15 | 15 | 15 | mg/dL | 6–23 |
| Creatinine | 2.98 | 3.08 | 3.1 | 2.77 | mg/dL | 0.1–1.7 |
| BUN/Creatine Ratio | 5.0 | 4.9 | 4.8 | 5.4 | — | 7.0–20.0 |
| Total Protein | 3.6 | 3.6 | 3.5 | 3.7 | gm/dL | 6.4–8.1 |
| Albumin | 2.7 | 2.7 | 2.8 | 2.8 | gm/dL | 3.7–5.1 |
| Globulin | 0.9 | 0.9 | 0.7 | 0.9 | gm/dL | 2.1–3.6 |
| Albumin/Globulin Ratio | 3.0 | 3.0 | 4.0 | 3.1 | — | 1.1–2.3 |
| Cholesterol | 30 | 30 | 32 | 30 | mg/dL | <200 |
| HDL Cholesterol | 28 | 30 | 30 | 27 | mg/dL | 39–90 |
| Chol/HDL Ratio | 1.07 | 1.00 | 1.07 | 1.11 | — | <4.5 |
| Triglycerides | 72 | 74 | 72 | 73 | mg/dL | 30–200 |
| Iron | 213 | 217 | 214 | 186 | meg/dL | 40–175 |
| Plasma Hb | 13.3 | 11.5 | 13.7 | 22.6 | mg/dL | 3.4–20.5 |

These results indicate that the γ irradiation process did not significantly affect the concentrations of most of the biochemical constituents of FBS. These results also indicate that upon spray-drying, several of the components of FBS (alkaline phosphatase, AST, and LD, and possibly glucose) undergo a significant reduction in concentration compared to their concentrations in the starting liquid FBS.

Example 16

Effects of Irradiation on Performance of Powdered Sera

To examine the impact of γ irradiation on the ability of dried powder sera to support cell growth, samples of spray-dried FBS irradiated under various conditions were used to supplement culture media, and adherent and suspension cells were grown for up to three passages in these media. As model suspension cells, the hybridoma lines SP2/0 and AE-1 were used, while VERO and BHK cultures were used as typical adherent cells. Cells were cultured in media containing test sera or control sera (spray-dried but not irradiated) for up to three passages according to the general procedures outlined in Example 14 above. At each passage point, cells were harvested and subcultured, while an aliquot was counted as above for viable cells/ml. Results at each point were expressed as a percentage of the viable cell count obtained in media supplemented with liquid FBS, and are shown in FIGS. 17A, 17B, 17C and 17D.

Figure 17A:
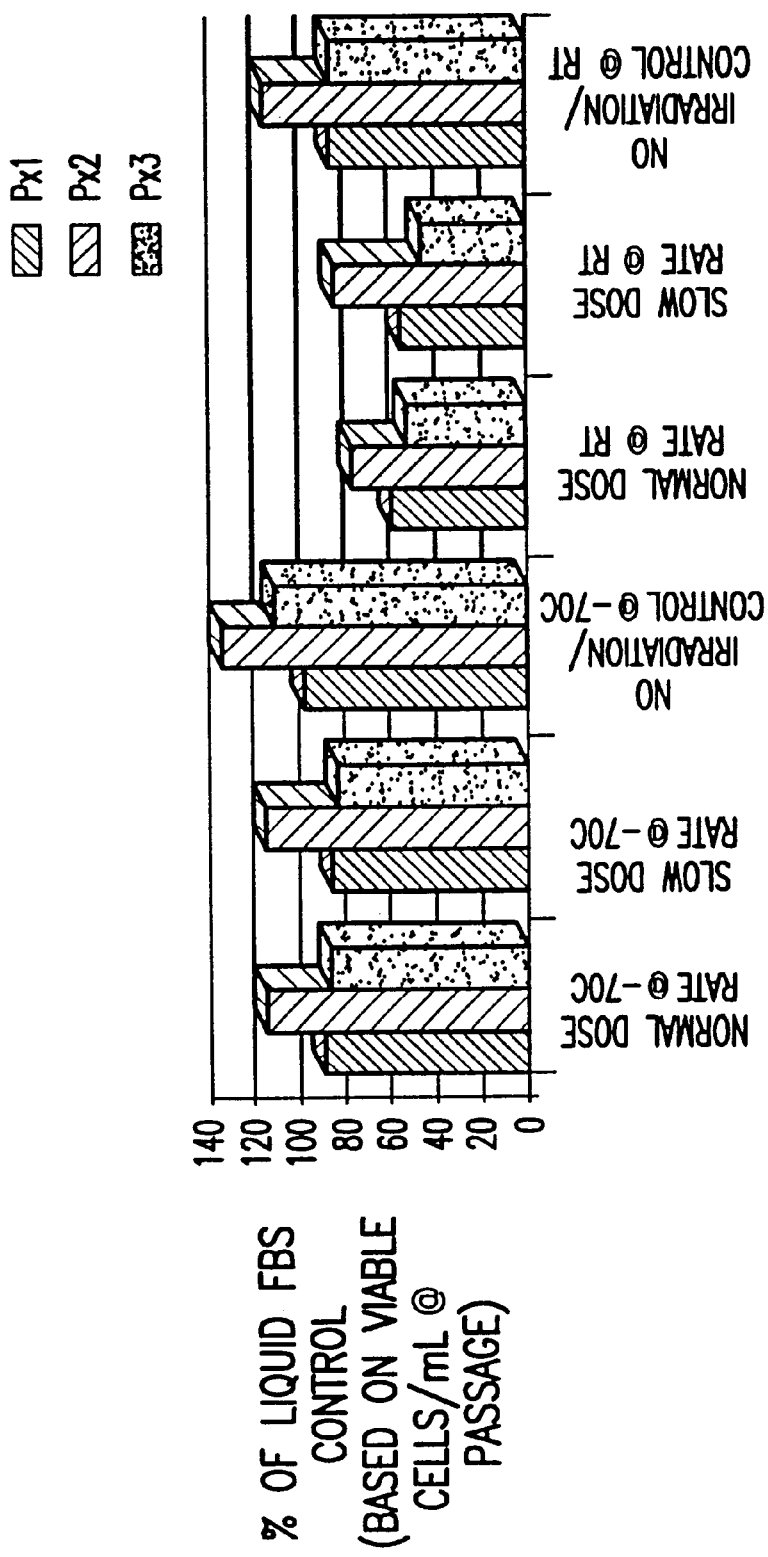
FIG. 17A: SP2/0 cells.
Figure 17C:
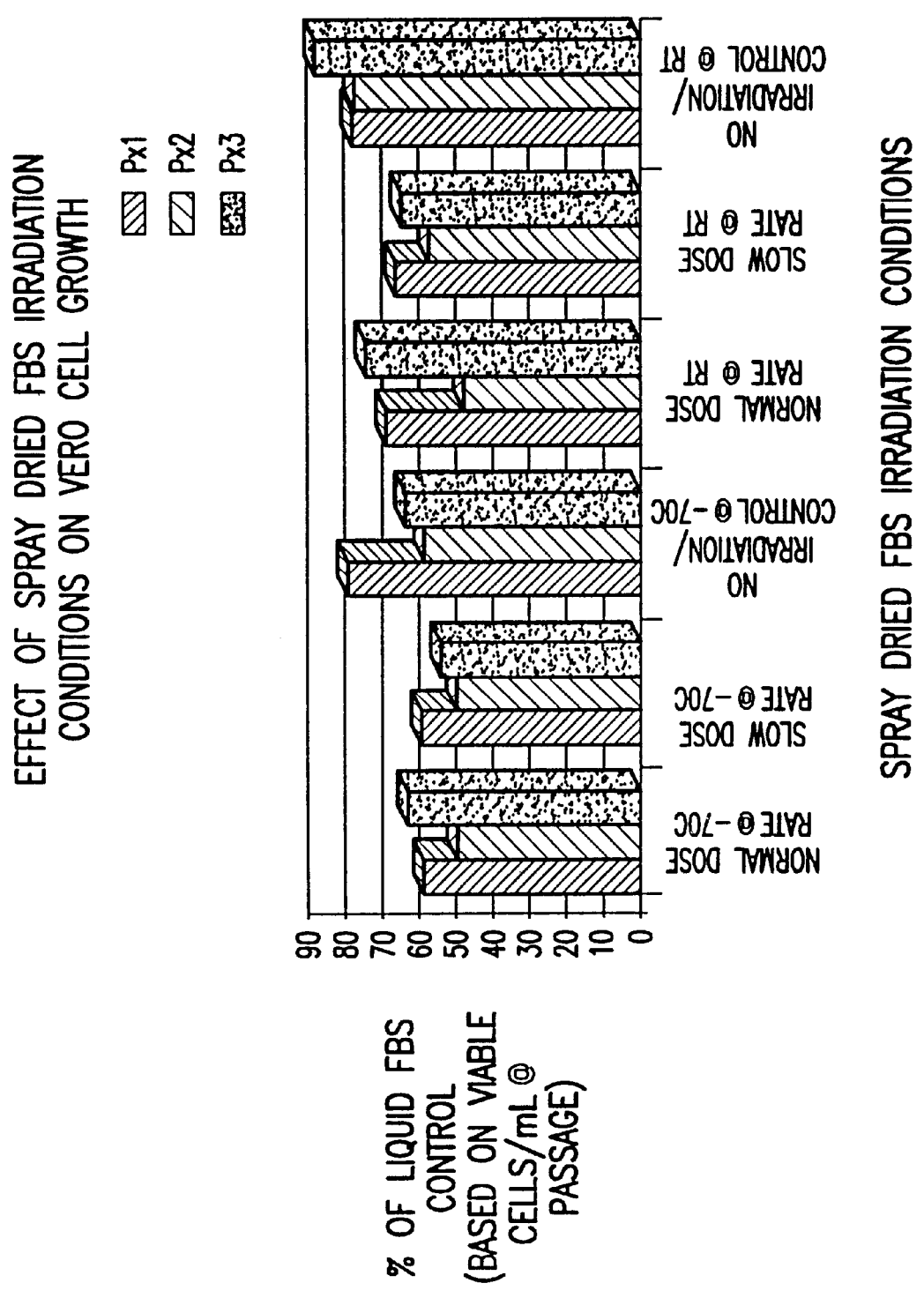
Figure 17D:
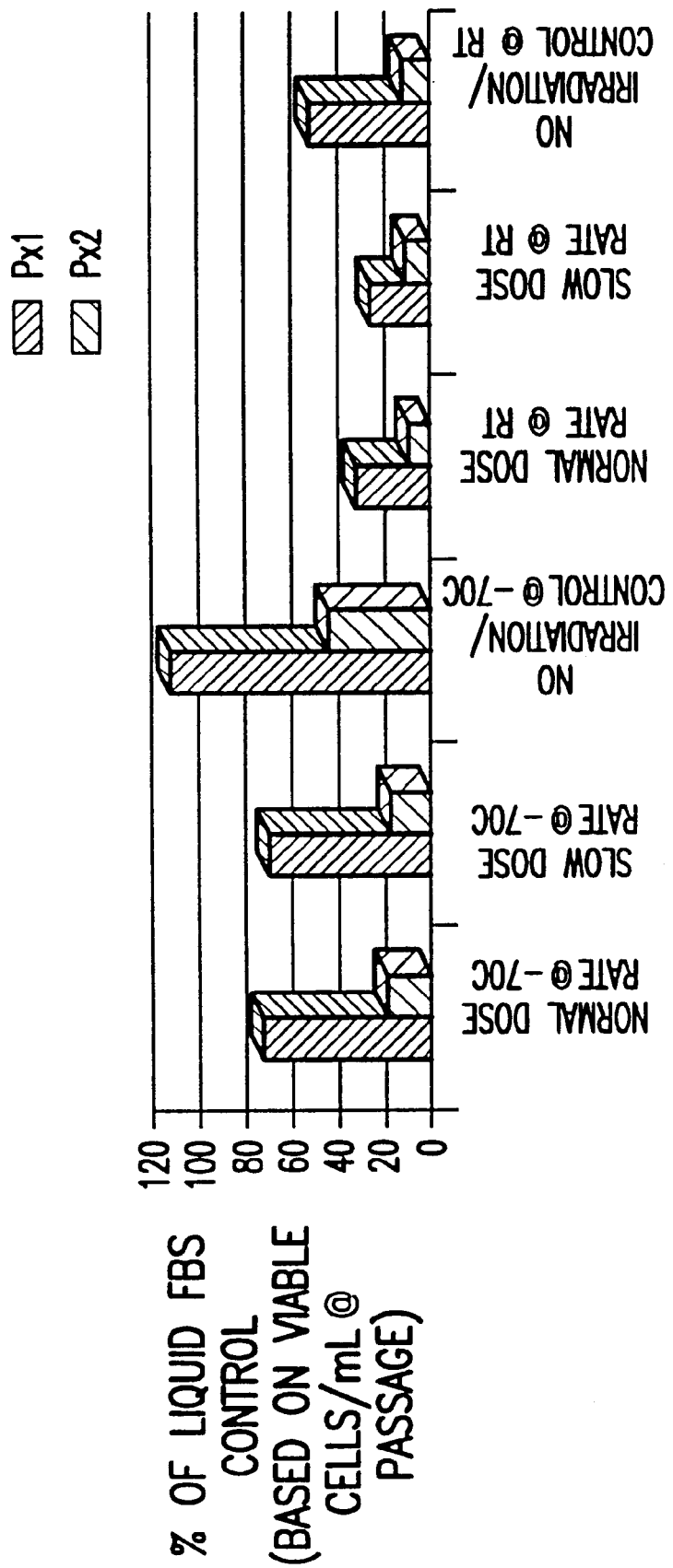
FIG. 17D: BHK cells.

Several conclusions may be drawn from the results of these studies. First, γ irradiation of FBS does not appear to reduce the ability of spray-dried FBS to support the growth of suspension and adherent cells (compare the irradiated data sets to the non-irradiated data set in each figure). In fact, BHK cells (FIG. 17D) actually grew better in media containing powdered FBS that had been irradiated at −70° C. than they did in non-irradiated sera. Second, sera irradiated at −70° C. appear to perform better than those irradiated at room temperature in their ability to support cell growth, except perhaps for VERO cells (FIG. 17C). Finally, the results of these studies were very cell type-specific: suspension cells (FIGS. 17A and 17B) grew better in spray-dried FBS, irradiated and non-irradiated, than did adherent cells (FIGS. 17C and 17D); and among adherent cells, BHK cells (FIG. 17D) grew better in spray-dried FBS than did VERO cells (FIG. 17C).

These results demonstrate that γ irradiation may be used as a sterilization technique in the preparation of bulk powdered sera, such as FBS, in the methods of the present invention. Furthermore, unlike those reported for transferrin in Example 14 above, these data suggest that the optimal temperature for irradiation of sera, in order to maintain the ability of the sera to support cell growth, is likely to be below room temperature.

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A method of producing an agglomerated eukaryotic cell culture medium powder, said method comprising agglomerating a dry powder eukaryotic cell culture medium with a solvent by:
    (a) placing said dry powder eukaryotic cell culture medium into a fluid bed apparatus;
    (b) introducing said solvent into said dry powder under conditions whereby said powder is moistened; and
    (c) drying said moistened powder, thereby producing an agglomerated eukaryotic cell culture medium powder,
wherein said agglomerated eukaryotic cell culture medium powder exhibits reduced dusting and a larger particle size than does said dry powder eukaryotic cell culture medium.

2. A method of producing an agglomerated eukaryotic cell culture medium supplement powder, said method comprising agglomerating a dry powder eukaryotic cell culture medium supplement with a solvent by:
    (a) placing said dry powder eukaryotic cell culture medium supplement into a fluid bed apparatus;
    (b) introducing said solvent into said dry powder under conditions whereby said powder is moistened; and
    (c) drying said moistened powder, thereby producing an agglomerated eukaryotic cell culture medium supplement powder,
wherein said agglomerated eukaryotic cell culture medium supplement powder exhibits reduced dusting and a larger particle size than does said dry powder cell eukaryotic culture medium supplement.

3. A method of producing an agglomerated eukaryotic cell culture medium subgroup powder, said method comprising agglomerating a dry powder eukaryotic cell culture medium subgroup with a solvent by:
    (a) placing said dry powder eukaryotic cell culture medium subgroup into a fluid bed apparatus;
    (b) introducing said solvent into said dry powder under conditions whereby said powder is moistened; and
    (c) drying said moistened powder, thereby producing an agglomerated eukaryotic cell culture medium subgroup powder,
wherein said agglomerated eukaryotic cell culture medium subgroup powder exhibits reduced dusting and a larger particle size than does said dry eukaryotic powder cell culture medium subgroup.

4. A method of producing an agglomerated eukaryotic cell culture medium buffer powder, said method comprising agglomerating a dry powder eukaryotic cell culture medium buffer with a solvent by:
    (a) placing said dry powder eukaryotic cell culture medium buffer into a fluid bed apparatus;
    (b) introducing said solvent into said dry powder under conditions whereby said powder is moistened; and
    (c) drying said moistened powder, thereby producing an agglomerated eukaryotic cell culture medium buffer powder,
wherein said agglomerated buffer powder exhibits reduced dusting and a larger particle size than does said dry powder buffer.

5. The method of any one of claims 1–4, further comprising packaging said agglomerated powder.

6. The method of any one of claims 1–4, further comprising sterilizing said agglomerated powder.

7. The method of claim 6, wherein said sterilization is performed after packaging said agglomerated powder.

8. The method of claim 6, wherein said sterilization is accomplished by irradiation of said powder with gamma rays until said powder is rendered sterile.

9. The method of claim 1, further comprising adding at least one medium supplement to said agglomerated eukaryotic cell culture medium powder by spray-drying at least one liquid medium supplement onto said agglomerated eukaryotic cell culture medium powder.

10. The method of claim 1, further comprising adding an acid or base to said eukaryotic cell culture medium powder by agglomerating said dry powder eukaryotic cell culture medium with at least one liquid acid or base.

11. The method of claim 1, wherein said agglomerated eukaryotic cell culture medium powder is selected from the group consisting of a yeast cell culture medium powder, a plant cell culture medium powder and an animal cell culture medium powder.

12. The method of claim 1, wherein said agglomerated eukaryotic cell culture medium powder comprises one or more ingredients selected from the group consisting of serum, L-glutamine, insulin, transferrin, a lipid, a cytokine, a neurotransmitter and a buffer.

13. The method of claim 2, wherein said cell culture medium supplement is serum.

14. The method of claim 3, wherein said cell culture medium supplement is serum.

15. The method of claim 9, wherein said medium supplement is serum.

16. The method of any one of claims 13–15, wherein said serum is bovine serum or human serum.

17. The method of claim 16, wherein said bovine serum is fetal bovine serum or calf serum.

18. The method of claim 12, wherein said buffer is sodium bicarbonate.

19. The method of claim 4, wherein said powder buffer eukaroytic cell culture medium buffer is a buffered saline powder.

20. The method of claim 19, wherein said buffered saline powder is a phosphate-buffered saline powder or a Tris-buffered saline powder.

21. The method of claim 1, wherein said agglomerated cell culture medium powder is an animal cell culture medium powder.

22. The method of claim 21, wherein said animal cell culture medium powder is suitable for culturing an animal cell selected from the group consisting of an insect cell, a nematode cell and a mammalian cell.

23. The method of claim 1, wherein said agglomerated cell culture medium powder is a plant cell culture medium powder.

24. The method of any one of claims 1–4, wherein said agglomerated powder exhibits more rapid dissolution upon reconstitution with a solvent.

\* \* \* \* \*